(12) United States Patent
Jiang et al.

(10) Patent No.: US 11,441,049 B2
(45) Date of Patent: Sep. 13, 2022

(54) ZWITTERIONIC COPOLYMER COATINGS AND RELATED METHODS

(71) Applicant: University of Washington, Seattle, WA (US)

(72) Inventors: Shaoyi Jiang, Seattle, WA (US); Xiaojie Lin, Seattle, WA (US); Jonathan Himmelfarb, Seattle, WA (US); Buddy D. Ratner, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 17/435,654

(22) PCT Filed: Mar. 13, 2020

(86) PCT No.: PCT/US2020/022543
§ 371 (c)(1),
(2) Date: Sep. 1, 2021

(87) PCT Pub. No.: WO2020/186134
PCT Pub. Date: Sep. 17, 2020

(65) Prior Publication Data
US 2022/0041886 A1    Feb. 10, 2022

Related U.S. Application Data

(60) Provisional application No. 62/818,299, filed on Mar. 14, 2019, provisional application No. 62/818,283, filed on Mar. 14, 2019, provisional application No. 62/818,265, filed on Mar. 14, 2019.

(51) Int. Cl.
C09D 133/26 (2006.01)
C08J 3/28 (2006.01)
A61L 29/06 (2006.01)
A61L 29/04 (2006.01)
(Continued)

(52) U.S. Cl.
CPC .......... *C09D 133/26* (2013.01); *A61L 29/041* (2013.01); *A61L 29/06* (2013.01); *A61L 29/085* (2013.01); *A61L 29/141* (2013.01); *C08J 3/28* (2013.01); *C08J 2333/26* (2013.01)

(58) Field of Classification Search
None
See application file for complete search history.

(56) References Cited

U.S. PATENT DOCUMENTS

2015/0148444 A1    5/2015  Prenzel
2020/0138708 A1*   5/2020  Labib ................ A61F 2/02
(Continued)

OTHER PUBLICATIONS

Nagahashi, K.; Teramura, Y.; Takai, M. Stable surface coating of silicone elastomer with phosphorylcholine and organosilane copolymer with cross-linking for repelling proteins. Colloids Surf., B 2015, 134, 384-391.
(Continued)

*Primary Examiner* — Tae H Yoon
(74) *Attorney, Agent, or Firm* — Christensen O'Connor Johnson Kindness PLLC

(57) ABSTRACT

Zwitterionic carboxybetaine copolymers and their use in coatings to impart non-fouling and functionality to surfaces, particularly surfaces of blood-contacting medical devices.

15 Claims, 35 Drawing Sheets

(51) Int. Cl.
*A61L 29/08* (2006.01)
*A61L 29/14* (2006.01)

(56) References Cited

U.S. PATENT DOCUMENTS

2021/0145445 A9* 5/2021 Goldsmith ......... A61B 17/3468
2021/0198516 A1* 7/2021 Locklin .................. A61L 29/16

OTHER PUBLICATIONS

Nilsson, B.; Ekdahl, K. N.; Molines, T. E.; Lambris, J. D., The role of complement in biomaterial-induced inflammation. Mol. Immunol. 2007,44 (1), 82-94.
Ratner, B. D.; Bryant, S. J. Biomaterials: where we have been and where we are going. Annu. Rev. Biomed. Eng. 2004, 6, 41-75.
Roach, P.; Farrar, D.; Perry, C. C., Interpretation of Protein Adsorption: Surface-Induced Conformational Changes. J Am Chem Soc 2005, 127 (22), 8168-8173.
Rowdhwal, S. S. S.; Chen, J., Toxic Effects of Di-2-ethylhexyl Phthalate: An Overview. BioMed Research International 2018, 2018, 10.
Ryu, G. H.; Kim, J.; Ruggeri, Z. M.; Han, S. H.; Kim, J. H.; Min, B. G., Effect of Shear Stress on Fibrinogen Adsorption and Its Conformational Change. ASAIO J 1995, 41 (3), M384-M388.
Serrano, Á.; Sterner, O.; Mieszkin, S.; Zürcher, S.; Tosatti, S.; Callow, M. E.; Callow, J. A.; Spencer, N. D. Nonfouling response of hydrophilic uncharged polymers. Adv. Funct. Mater. 2013, 23, 5706-5718.
Shao, Q.; Jiang, S. Molecular understanding and design of zwitterionic materials. Adv. Mater. 2015, 27, 15-26.
Sinclair, A.; O'Kelly, M. B.; Bai, T.; Hung, H.-C.; Jain, P.; Jiang, S., Self-Healing Zwitterionic Microgels as a Versatile Platform for Malleable Cell Constructs and Injectable Therapies. Adv Mater 2018, 30 (39), 1803087.
Sun, F.; Wu, K.; Hung, H.-C.; Zhang, P.; Che, X.; Smith, J.; Lin, X.; Li, B.; Jain, P.; Yu, Q.; Jiang, S. Paper sensor coated with a poly(carboxybetaine)-multiple DOPA conjugate via dip-coating for biosensing in complex media. Anal. Chem. 2017, 89, 10999-11004.
Tanaka, M.; Motomura, T.; Kawada, M.; Anzai, T.; Yuu, K.; Shiroya, T.; Shimura, K.; Onishi, M.; Akira, M. Blood compatible aspects of poly(2-methoxyethylacrylate) (PMEA)-relationship between protein adsorption and platelet adhesion on PMEA surface. Biomaterials 2000, 21, 1471-1481.
Tanaka, M.; Sato, K.; Kitakami, E.; Kobayashi, S.; Hoshiba, T.; Fukushima, K. Design of biocompatible and biodegradable polymers based on intermediate water concept. Polym. J. 2015, 47, 114.
Tang, L.; Thevenot, P.; Hu, W. Surface chemistry influence implant biocompatibility. Curr. Top. Med. Chem. 2008, 8, 270-280.
Tomokiyo, K.; Kamikubo, Y.; Hanada, T.; Araki, T.; Nakatomi, Y.; Ogata, Y.; Jung, S. M.; Nakagaki, T.; Moroi, M., Von Willebrand factor accelerates platelet adhesion and thrombus formation on a collagen surface in platelet-reduced blood under flow conditions. Blood 2005, 105 (3), 1078-1084.
Trel'ová, D.; Salgarella, A. R.; Ricotti, L.; Giudetti, G.; Cutrone, A.; Š rámková, P.; Zahoranová, A.; Chorvát, D.; Haško, D.; Canale, C.; Micera, S.; Kronek, J.; Menciassi, A.; Lacik, I. Soft hydrogel zwitterionic coatings minimize fibroblast and macrophage adhesion on polyimide substrates. Langmuir 2018, DOI: 10.1021/acs.langmuir.8b00765.
Vaisocherová, H.; Yang, W.; Zhang, Z.; Cao, Z.; Cheng, G.; Piliarik, M.; Homola, J.; Jiang, S. Ultralow fouling and functionalizable surface chemistry based on a zwitterionic polymer enabling sensitive and specific protein detection in undiluted blood plasma. Anal. Chem. 2008, 80, 7894-7901.
Wei, H.; Malcor, J.-D. M.; Harper, M. T., Lipid rafts are essential for release of phosphatidylserine-exposing extracellular vesicles from platelets. Scientific Reports 2018, 8 (1), 9987.
Williams, D. F. On the mechanisms of biocompatibility. Biomaterials 2008, 29, 2941-2953.
Yang, W.; Xue, H.; Li, W.; Zhang, J.; Jiang, S., Pursuing "Zero" Protein Adsorption of Poly(carboxybetaine) from Undiluted Blood Serum and Plasma. Langmuir 2009, 25 (19), 11911-11916.
Yin, H. Q.; Zhao, X. B.; Courtney, J. M.; Blass, C. R.; West, R. H.; Lowe, G. D. O., Blood interactions with plasticized poly(vinyl chloride): relevance of plasticizer selection. J. Mater. Sci. Mater. Med. 1999, 10 (9), 527-531.
Yuan, J.; Cheng, B., A Strategy for Nonmigrating Highly Plasticized PVC. Scientific Reports 2017, 7 (1), 9277.
Zhang, L.; Cao, Z.; Bai, T.; Carr, L.; Ella-Menye, J.-R.; Irvin, C.; Ratner, B. D.; Jiang, S. Zwitterionic hydrogels implanted in mice resist the foreign-body reaction. Nat. Biotechnol. 2013, 31, 553-556.
Zhang, P.; Jain, P.; Tsao, C.; Yuan, Z.; Li, W.; Li, B.; Wu, K.; Hung, H.-C.; Lin, X.; Jiang, S. Polypeptide with high zwitterion density for safe and effective therapeutics. Angew. Chem., Int. Ed. 2018, 57, 7743.
Zhang, Y.; Yuan, Z.-P.; Qin, Y.; Dai, J.; Zhang, T., Comparative Studies on Hydrophilic and Hydrophobic Segments Grafted Poly(vinyl chloride). Chinese J Polym Sci 2018, 36 (5), 604 611.
Zhang, Z.; Vaisocherová, H.; Cheng, G.; Yang, W.; Xue, H.; Jiang, S., Nonfouling Behavior of Polycarboxybetaine-Grafted Surfaces: Structural and Environmental Effects Biomacromolecules 2008, 9 (10), 2686-2692.
International Search Report dated Jul. 6, 2020, issued in corresponding International Application No. PCT/US2020/022543, filed Mar. 13, 2020, 6 pages.
Written Opinion of the International Searching Authority dated Jul. 6, 2020, issued in corresponding International Application No. PCT/US2020/022543, filed Mar. 13, 2020, 7 pages.
Arima, Y.; Toda, M.; Iwata, H., Complement activation on surfaces modified with ethylene glycol units. Biomaterials 2008, 29 (5), 551-560.
Asif, S.; Asawa, K.; Inoue, Y.; Ishihara, K.; Lindell, B.; Holmgren, R.; Nilsson, B.; Ryden, A.; Jensen-Waern, M.; Teramura, Y.; Ekdahl, K. N., Validation of an MPC Polymer Coating to Attenuate Surface-Induced Crosstalk between the Complement and Coagulation Systems in Whole Blood in In Vitro and In Vivo Models Macromol Biosci 2019, 19 (5), 1800485.
Babukutty, Y.; Prat, R.; Endo, K.; Kogoma, M.; Okazaki, S.; Kodama, M., Poly(vinyl chloride) Surface Modification Using Tetrafluoroethylene in Atmospheric Pressure Glow Discharge. Langmuir 1999, 15 (20), 7055-7062.
Bernard, L.; Décaudin, B.; Lecoeur, M.; Richard, D.; Bourdeaux, D.; Cueff, R.; Sautou, V., Analytical methods for the determination of DEHP plasticizer alternatives present in medical devices: A review. Taianta 2014, 129, 39-54.
Brault, N. D.; White, A. D.; Taylor, A. D.; Yu, Q.; Jiang, S. Directly functionalizable surface platform for protein arrays in undiluted human blood plasma. Anal. Chem. 2013, 85, 1447-1453.
Cabezudo, N.; Sun, J.; Andi, B.; Ding, F.; Wang, D.; Chang, W.; Luo, X.; Xu, B. B., Enhancement of surface wettability via micro- and nanostructures by single point diamond turning. Nanotechnology and Precision Engineering 2019, 2 (1), 8-14.
Castner, D. G.; Ratner, B. D. Biomedical surface science: Foundations to frontiers. Surf. Sci. 2002, 500, 28-60.
Chen, G.; Hu, H.; Wu, T.; Tong, P.; Liu, B.; Zhu, B.; Du, Y., Rapid and sensitive determination of plasticizer diethylhexyl phthalate in drink by diffuse reflectance UV spectroscopy coupled with membrane filtration. Food Control 2014, 35 (1), 218-222.
Chen, H.; Yuan, L.; Song, W.; Wu, Z.; Li, D. Biocompatible polymer materials: Role of protein-surface interactions. Prog. Polym. Sci. 2008, 33, 1059-1087.
Chen, H.; Zou, H.; Paholak, H. J.; Ito, M.; Qian, W.; Che, Y.; Sun, D. Thiol-reactive amphiphilic block copolymer for coating gold nanoparticles with neutral and functionable surfaces. Polym. Chem. 2014, 5, 2768-2773.
Chen, S.; Li, L.; Zhao, C.; Zheng, J. Surface hydration: Principles and applications toward low-fouling/nonfouling biomaterials. Polymer 2010, 51, 5283-5293.

(56) References Cited

OTHER PUBLICATIONS

Chiellini, F.; Ferri, M.; Morelli, A.; Dipaola, L.; Latini, G., Perspectives on alternatives to phthalate plasticized poly(vinyl chloride) in medical devices applications. Prog Polym Sci 2013, 38 (7), 1067-1088.

Cuenca, L. et al., Environmentally-relevant exposure to diethylhexyl phthalate (DEHP) alters regulation of double-strand break formation and crossover designation leading to germline dysfunction in Caenorhabditis elegans, PLOS Genetics, 2020, 1-30.

Dalsin, J. L.; Messersmith, P. B. Bioinspired antifouling polymers. Mater. Today 2005, 8, 38-46.

Demirci, N.; Demirel, M.; Dilsiz, N., Surface Modification of PVC Film with Allylamine Plasma Polymers. Adv Polym Tech 2014, 33 (4).

Eilenberger, C.; Rothbauer, M.; Ertl, P.; Küpcü, S. A selfassembled antifouling nano-biointerface for the generation of spheroids. Methods Mol. Biol. 2018, 1771, 251-258.

Ekdahl, K. N.; Lambris, J. D.; Elwing, H.; Ricklin, D.; Nilsson, P. H.; Teramura, Y.; Nicholls, I. A.; Nilsson, B., Innate Immunity activation on biomaterial surfaces: A mechanistic model and coping strategies. Adv Drug Deliver Rev 2011, 63 (12), 1042-1050.

Ekdahl, K. N.; Nilsson, B.; Pekna, M.; Nilsson, U. R., Generation of iC3 at the Interface between Blood and Gas. Scand J Immunol 1992, 35 (1), 85-91.

Geilich, B. M.; Webster, T. J., Reduced adhesion of *Staphylococcus aureus* to ZnO/PVC nanocomposites. International journal of nanomedicine 2013, 8, 1177-1184.

Hadjesfandiari, N.; Weinhart, M.; Kizhakkedathu, J. N.; Haag, R.; Brooks, D. E., Development of Antifouling and Bactericidal Coatings for Platelet Storage Bags Using Dopamine Chemistry. Advanced Healthcare Materials 2018, 7 (5), 1700839.

Hoffman, A. S. Blood-biomaterial interactions: An overview. Biomaterials: Interfacial Phenomena and Applications; American Chemical Society: Washington, D.C., 1982; vol. 199, pp. 3-8.

Hong, D.; Hung, H.-C.; Wu, K.; Lin, X.; Sun, F.; Zhang, P.; Liu, S.; Cook, K. E.; Jiang, S., Achieving Ultralow Fouling under Ambient Conditions via Surface-Initiated ARGET ATRP of Carboxybetaine. ACS Applied Materials & Interfaces 2017, 9 (11), 9255-9259.

Horbett, T. A., Fibrinogen adsorption to biomaterials. J Biomed Mater Res A 2018, 106 (10), 2777-2788.

Hung, H.-C.; Jain, P.; Zhang, P.; Sun, F.; Sinclair, A.; Bai, T.; Li, B.; Wu, K.; Tsao, C.; Liu, E. J.; Sundaram, H. S.; Lin, X.; Farahani, P.; Fujihara, T.; Jiang, S. A coating-free nonfouling polymeric elastomer. Adv. Mater. 2017, 29, 1700617.

Ishihara, K.; Ishikawa, E.; Iwasaki, Y.; Nakabayashi, N. Inhibition of fibroblast cell adhesion on substrate by coating with 2-methacryloyloxyethyl phosphorylcholine polymers. J. Biomater. Sci., Polym. Ed. 1999, 10, 1047-1061.

Ishihara, K.; Oshida, H.; Endo, Y.; Ueda, T.; Watanabe, A.; Nakabayashi, N. Hemocompatibility of human whole blood on polymers with a phospholipid polar group and its mechanism. J Biomed. Mater. Res. 1992, 26, 1543-1552.

Iwasaki, Y.; Ishihara, K. Cell membrane-inspired phospholipid polymers for developing medical devices with excellent biointerfaces. Sci. Technol. Adv. Mater. 2012, 13, 064101.

Jain, P.; Hung, H.-C.; Li, B.; Ma, J.; Dong, D.; Lin, X.; Sinclair, A.; Zhang, P.; O'Kelly, M. B.; Niu, L.; Jiang, S. Zwitterionic hydrogels based on a degradable disulfide carboxybetaine cross-linker. Langmuir 2018, DOI: 10.1021/acs.langmuir.8b02100.

Jain, P.; Hung, H.-C.; Lin, X.; Ma, J.; Zhang, P.; Sun, F.; Wu, K.; Jiang, S. Poly(ectoine) hydrogels resist nonspecific protein adsorption. Langmuir 2017, 33, 11264-11269.

Jayakrishnan, A. et al., Phase transfer catalysed surface modification of plasticized poly(vinyl chloride) in aqueous media to retard plasticizer migration, Polymer, 1996, 37, 23, 5213-5218.

Jiang, S.; Cao, Z. Ultralow-fouling, functionalizable, and hydrolyzable zwitterionic materials and their derivatives for biological applications. Adv. Mater. 2010, 22, 920-932.

Keefe, A. J.; Jiang, S. Poly(zwitterionic)protein conjugates offer increased stability without sacrificing binding affinity or bioactivity. Nat. Chem. 2012, 4, 59-63.

Ladd, J.; Zhang, Z.; Chen, S.; Hower, J. C.; Jiang, S. Zwitterionic polymers exhibiting high resistance to nonspecific protein adsorption from human serum and plasma. Biomacromolecules 2008, 9, 1357-1361.

Lamba, N. M. K.; Courtney, J. M.; Gaylor, J. D. S.; Lowe, G. D. O., In vitro investigation of the blood response to medical-grade PVC and the effect of heparin on the blood response Biomaterials 2000, 21 (1), 89-96.

Li, B.; Xie, J.; Yuan, Z.; Jain, P.; Lin, X.; Wu, K.; Jiang, S. Mitigation of inflammatory immune responses with hydrophilic nanoparticles. Angew. Chem., Int. Ed. 2018, 57, 4527-4531.

Li, B.; Yuan, Z.; Hung, H.-C.; Ma, J.; Jain, P.; Tsao, C.; Xie, J.; Zhang, P.; Lin, X.; Wu, K.; Jiang, S. Revealing the immunogenic risk of polymers. Angew. Chem., Int. Ed. 2018 (57) 13873-13876.

Li, B.; Yuan, Z.; Zhang, P.; Sinclair, A.; Jain, P.; Wu, K.; Tsao, C.; Xie, J.; Hung, H. C.; Lin, X.; Bai, T.; Jiang, S., Zwitterionic Nanocages Overcome the Efficacy Loss of Biologic Drugs. Adv Mater 2018, 30 (14), 1705728.

Lin, X. et al., Ultralow Fouling and Functionalizable Surface Chemistry Based on Zwitterionic Carboxybetaine Random Copolymers, Langmuir, 2019, 35 (5), 1544-1551.

Lin, X. et al., Photoreactive Carboxybetaine Copolymers Impart Biocompatibility and Inhibit Plasticizer Leaching on Polyvinyl Chloride, ACS Applied Materials & Interfaces, 2020, 12, 41026-41037.

Lin, X.; Fukazawa, K.; Ishihara, K. Photoinduced inhibition of DNA unwinding in vitro with water-soluble polymers containing both phosphorylcholine and photoreactive groups. Acta Biomater. 2016, 40, 226-234.

Lin, X.; Fukazawa, K.; Ishihara, K., Photoreactive Polymers Bearing a Zwitterionic Phosphorylcholine Group for Surface Modification of Biomaterials. ACS Applied Materials & Interfaces 2015, 7 (31), 17489-17498.

Lin, X.; Ishihara, K. Water-soluble polymers bearing phosphorylcholine group and other zwitterionic groups for carrying DNA derivatives. J. Biomater. Sci., Polym. Ed. 2014, 25, 1461-1478.

Lin, X.; Konno, T.; Ishihara, K., Cell-Membrane-Permeable and Cytocompatible Phospholipid Polymer Nanoprobes Conjugated with Molecular Beacons. Biomacromolecules 2014, 15 (1), 150-157.

Lin, X.; Konno, T.; Takai, M.; Ishihara, K. Enzyme oxidaseimmobilized phospholipid polymer microparticles for biofuel cell application. Trans. Mater. Res. Soc. Jpn. 2011, 36, 531-534.

Lin, X.; Konno, T.; Takai, M.; Ishihara, K. Redox phospholipid polymer microparticles as doubly functional polymer support for immobilization of enzyme oxidase. Colloids Surf., B 2013, 102, 857-863.

Lin, X.; Nishio, K.; Konno, T.; Ishihara, K. The effect of the encapsulation of bacteria in redox phospholipid polymer hydrogels on electron transfer efficiency in living cell-based devices. Biomaterials 2012, 33, 8221-8227.

Liu, Q. et al., Transparent Grafted Zwitterionic Copolymer Coatings That Exhibit Both Antifogging and Self-Cleaning Properties, ACS Omega, 2018, 3, 12, 17743-17750.

Lowe, S.; O'Brien-Simpson, N. M.; Connal, L. A., Antibiofouling polymer interfaces: poly(ethylene glycol) and other promising candidates. Polymer Chemistry 2015, 6 (2), 198-212.

Malarvannan, G.; Onghena, M.; Verstraete, S.; van Puffelen, E.; Jacobs, A.; Vanhorebeek, I.; Verbruggen, S. C. A. T.; Joosten, K. F. M.; Van den Berghe, G.; Jorens, P. G.; Covaci, A., Phthalate and alternative plasticizers in indwelling medical devices in pediatric intensive care units. J Hazard Mater 2019, 363, 64-72.

Marck, R. E.; van der Bijl, I.; Korsten, H.; Lorinser, J.; de Korte, D.; Middelkoop, E., Activation, function and content of platelets in bum patients. Platelets 2019, 30 (3), 396-402.

International Preliminary Report on Patentability dated Sep. 23, 2021, issued in corresponding International Application No. PCT/US2020/022543, filed Mar. 13, 2020, 9 pages.

\* cited by examiner

| | monomer unit composition (mol %) | | initiator (mmol/L) | polymerization time (h) | yield (%) | molecular weight [c] | | solubility [d] | |
|---|---|---|---|---|---|---|---|---|---|
| | in feed CB / BMA | in copolymer [b] CB / BMA | | | | $M_w \times 10^4$ | $M_w/M_n$ | ethanol | water |
| PCB1-28 | 20 / 80 | 17 / 83 | 5 | 16 | 80 | 7.4 | 2.6 | + + | − − |
| PCB1-37 | 30 / 70 | 31 / 69 | 5 | 16 | 87 | 8.3 | 2.4 | + + | − − |
| PCB1-46 | 40 / 60 | 38 / 62 | 5 | 16 | 88 | 6.7 | 2.8 | + + | + + |
| PCB1-55 | 50 / 50 | 50 / 50 | 5 | 16 | 78 | 7.1 | 2.3 | + + | + + |
| PCB1-64 | 60 / 40 | 57 / 43 | 5 | 16 | 80 | 7.5 | 2.7 | + + | + + |
| PCB1-82 | 80 / 20 | 82 / 18 | 5 | 16 | 85 | 6.9 | 2.5 | + + | + + |
| PCB2-37 | 30 / 70 | 27 / 73 | 5 | 16 | 86 | 7.9 | 2.8 | + + | − − |

*FIG. 3* uncoated

PCB-coated

| Sample | Atomic Concentration (%) | | | | |
|---|---|---|---|---|---|
| | C 1s | O 1s | N 1s | Cl 2p | Si 2p |
| 1) PCB polymer | 73.4 | 17.5 | 9.1 | / | / |
| 2) Uncoated before rinse | 69.3 | 12.8 | / | 8.6 | 9.3 |
| 3) Uncoated after rinse | 69.3 | 13.5 | / | 12.5 | 4.7 |
| 4) PCB-coated before soaking | 69.4 | 18.2 | 6.9 | 1.4 | 4.2 |
| 5) PCB-coated after soaking | 70.5 | 18.4 | 5.3 | 1.4 | 4.4 |

Protein fouling under static condition

ZWITTERIONIC COPOLYMER COATINGS AND RELATED METHODS

CROSS-REFERENCES TO RELATED APPLICATIONS

This application claims the benefit of U.S. Application No. 62/818,265, filed Mar. 14, 2019, U.S. Application No. 62/818,283, filed Mar. 14, 2019, and U.S. Application No. 62/818,299, filed Mar. 14, 2019, each expressly incorporated herein by reference in its entirety.

STATEMENT OF GOVERNMENT LICENSE RIGHTS

This invention was made with Government support under Grant No. R01 HL089043 awarded by the National Institute of Health Sciences. The Government has certain rights in the invention.

BACKGROUND OF THE INVENTION

Biofouling on blood-contacting medical device surfaces remains to be of major concern for thrombosis. Protein adsorption is the primary event that occurs on the surface of biomaterials in contact with biological media. Non-specific protein adsorption triggers biofouling culminating in serious adverse biological responses such as platelet activation, thrombus formation, complement activation, and inflammatory reaction among various others. Thus, anti-thrombogenic blood-contacting devices strive to effectively avoid non-specific protein adsorption. This is created through an ultra-low fouling interface between blood components and the surface they are in contact with. Synthetic polymer biomaterials with hydrophilic and charge-neutral characters are promising due to their high biocompatibility. Conventional biomaterials, such as poly(2-hydroxyethyl methacrylate) poly(HEMA) and poly(ethylene glycol) (PEG) have been historically used as the gold standards for surface modification. However, poly(HEMA) has low water content and poor resistance to protein adsorption while PEG can induce adverse reactions, including the emergence of anti-PEG antibodies and PEG-induced tissue histologic changes.

It is known that an indestructible hydration layer formed on the polymer chain surface can repel the adsorption of biomolecules with high efficacy. Thus, hydration induced nonfouling capability is a predominant feature for a hydrophilic nonfouling polymer biomaterial. Zwitterionic compounds comprising of super-hydrophilic zwitterionic groups, particularly phosphorylcholine (PC), carboxybetaine (CB) and sulfobetaine (SB), have become popular as blood-inert biomaterials over the past two decades. The zwitterionic groups, which are superhydrophilic and charge-neutral with an inner salt structure, can form a layer of strongly bound water molecules that cannot be displaced by bioactive species, thus inhibiting non-specific protein adsorption. Recently, CB-based polymers show excellent hydration-induced nonfouling capability for various applications, making them very attractive for blood-contacting surface use. Furthermore, CB groups have the unique capability to covalently immobilize biomolecules, such as proteins, enzymes and oligonucleotide, to their carboxyl groups.

Surface modification using zwitterionic polymers can be achieved either through "grafting from" or "grafting to" methods. To achieve noninvasive surface coatings for massive molded medical devices with various shapes and sizes, "grafting to" polymers are shown to be far more robust by simply applying various polymers with different architectures, such as homopolymer, random copolymer, and di-/tri-/multi-block copolymer, to various surfaces via silane, catechol, and photo-/heat-induced covalent bonding. Among them, random-type amphiphilic zwitterionic copolymers are a simple, yet effective nonfouling material that can effectively resist protein adsorption and platelet adhesion for a long term in blood-contacting surfaces. Poly(MPC-co-n-butyl methacrylate (BMA)) with about 30 mol % of hydrophilic unit has been applied to many surfaces of medical devices with excellent biocompatibility. However, comprehensive investigations of CB random copolymers are still lacking up to now. Furthermore, their capability for the surface functionalization of terminal carboxyl groups makes them an attractive surface modification material.

Despite the advances in the development of nonfouling polymeric materials and their use in surface coatings, a need exists for improved materials and surface coatings particularly improved materials that can be readily coated on surfaces to advantageously provide nonfouling surfaces for blood-contacting medical device surfaces. The present invention seeks to fulfill this need and provides further related advantages.

SUMMARY OF THE INVENTION

The present invention provides zwitterionic copolymers and their use in coatings to impart non-fouling and functionality to surfaces, particularly surfaces of blood-contacting medical devices. In certain aspects, the invention provides zwitterionic copolymers functionalized for their immobilization of surfaces, coating compositions that include the zwitterionic copolymers, surface coatings prepared from the zwitterionic copolymers, substrates having surfaces modified by the zwitterionic copolymers, and medical devices having surfaces modified by the zwitterionic copolymers.

In one aspect, the invention provides a method for inhibiting or preventing leaching of a plasticizer from a surface of a substrate, comprising:

(a) coating at least a portion of a surface of a substrate with a composition comprising a copolymer to provide a coated surface, the copolymer comprising first repeating units and second repeating units, wherein each of the first repeating units comprises a pendant zwitterionic group, and wherein each of the second repeating units comprises a pendant photoreactive group effective for crosslinking the copolymer on a surface, to provide a coated surface; and (b) irradiating the coated surface with light effective to crosslink the copolymer on the surface, thereby providing a coated surface effective for inhibiting or preventing leaching of a plasticizer from the surface.

In certain embodiments, the copolymer further comprises third repeating units, wherein each of the third repeating units comprises a pendant hydrophobic group effective for adsorbing the copolymer to the surface.

Surfaces that are advantageously treated by the above method include hydrocarbon-based surfaces, such as blood-contacting surfaces. Representative surfaces include polyolefin, polyester, polycarbonate, polyurethane (PU), polysulfone (PSF), poly(ether sulfone) (PES), polyamide, polyacrylic, polyimide, aromatic polyester, polyethylene (PE), polypropylene (PP), polystyrene (PS), poly(ethylene terephthalate) (PET), poly(vinyl chloride) (PVC), poly(dimethyl siloxane) (PMDS), poly(vinylidiene fluoride) (PVDF), poly(lactic acid) (PLA), and poly(methyl methacrylate) (PMMA) surfaces. In certain embodiments, the surface is a polyvinyl chloride surface or a polyurethane surface. In other embodiments, the surface is a cellulose or cellulose acetate surface.

In certain embodiments, the surface is the surface of polyvinyl chloride tubing or polyurethane tubing.

In other embodiments, the surface is a blood-contacting surface, such as a dialysis membrane or hydrocarbon-based membrane container.

In the above method, coating the surface with the composition comprises dipping the surface into the composition. In other embodiments, coating at least a portion of the surface comprises spraying, spinning, brushing, or rolling the composition onto the surface.

In certain embodiments, the method utilizes a copolymer of formula (III):

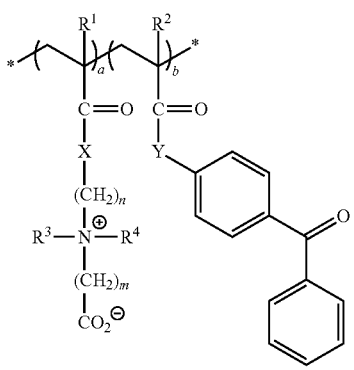

(III)

wherein $R_1$ and $R_2$ are independently —$(CH_2)_xH$, where x is an integer from 0 to 20;

$R_3$ and $R_4$ are independently —$(CH_2)_xH$, where x is an integer from 0 to 20;

X is O or NH;

Y is O or NH;

n is an integer from 1 to 20;

m is an integer from 1 to 20;

a is from about 0.10 to about 0.90 mole percent;

b is about 0.10 to about 0.90 mole percent;

a+b is 1.0; and

* represents the copolymer terminal groups.

In certain of these embodiments, $R_1$ is hydrogen or methyl, $R_2$ is hydrogen or methyl, $R_3$ and $R_4$ are methyl, and X is NH and Y is NH. In other of these embodiments, $R_1$ is hydrogen or methyl, $R_2$ is hydrogen or methyl, $R_3$ and $R_4$ are methyl, X is O, and Y is O. In certain embodiments, n is 2 or 3. In certain embodiments, m is 1 or 2. In certain embodiments, a is from about 0.70 to about 0.90 mole percent. In certain of these embodiments, a is about 0.80 mole percent. In certain embodiments, b is about 0.10 to about 0.30 mole percent. In certain of these embodiments, b is about 0.20 mole percent.

In one embodiment, the method utilizes a copolymer of formula (III), where $R_1$ is hydrogen, $R_2$ is hydrogen, $R_3$ and $R_4$ are methyl, X is NH, Y is NH, n is 3, and m is 1. In certain of these embodiments, a is about 0.80 mole percent. In certain of these embodiments, b is about 0.20 mole percent.

In other embodiments, the method utilizes a copolymer of formula (IV):

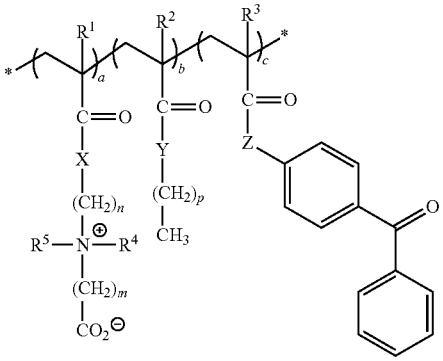

(IV)

wherein $R_1$, $R_2$, and $R_3$ are independently —$(CH_2)_xH$, where x is an integer from 0 to 20;

$R_4$ and $R_5$ are independently —$(CH_2)_xH$, where x is an integer from 0 to 20;

X is O or NH;

Y is O or NH;

Z is O or NH;

n is an integer from 1 to 20;

m is an integer from 1 to 20;

p is an integer from 0 to 20;

a is from about 0.10 to about 0.90 mole percent;

b is about 0.05 to about 0.95 mole percent;

c is from about 0.05 to about 0.95 mole percent;

a+b+c is 1.0; and

* represents the copolymer terminal groups.

In another aspect, the invention provides zwitterionic copolymers that are useful for coating surfaces to impart nonfouling properties to the coated surfaces.

In one embodiment, the invention provides a copolymer comprising first repeating units and second repeating units, wherein each of the first repeating units comprises a pendant zwitterionic group, and wherein each of the second repeating units comprises a pendant photoreactive group effective for crosslinking the copolymer. In a related embodiment, the copolymer further comprises third repeating units, wherein each of the third repeating units comprises a hydrophobic group effective for adsorbing the copolymer to a surface.

In another embodiment, the invention provides a copolymer comprising first repeating units, optional second repeating units, and optional third repeating units, provided that the copolymer includes at least first repeating units and optional second repeating units or at least first repeating units and optional third repeating units, wherein each of the first repeating units comprises a pendant zwitterionic group, wherein each of the second repeating units comprises a pendant photoreactive group effective for crosslinking the copolymer, and wherein each of the third repeating units comprises a pendant hydrophobic group effective for adsorbing the copolymer to a surface.

In a further embodiment, the invention provides a copolymer represented by formula (I):

$$*—(P_1)_a(P_2)_x(P_3)_y—* \qquad (1)$$

wherein $P_1$ is a repeating unit having a pendant zwitterionic group, $P_2$ is a repeating unit having a pendant hydrophobic group, $P_3$ is a repeating unit having a pendant photoreactive group, a is from about 0.10 to about 0.90 mole percent,
x is 0 to about 0.95 mole percent,
y is 0 to about 0.95 mole percent,
with the proviso that x and y are not both 0, and
a+x+y is 1.0.

In another embodiment, the invention provides a zwitterionic/hydrophobic copolymer having formula (II):

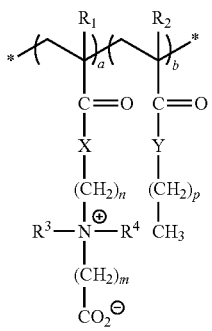

(II)

wherein
$R_1$ and $R_2$ are independently —$(CH_2)_xH$, where x is an integer from 0 to 20;
$R_3$ and $R_4$ are independently —$(CH_2)_xH$, where x is an integer from 0 to 20;
X is O or NH;
Y is O or NH;
n is an integer from 1 to 20;
m is an integer from 1 to 20;
p is an integer from 0 to 20;
a is from about 0.10 to about 0.90 mole percent;
b is about 0.10 to about 0.90 mole percent;
a+b is 1.0; and
* represents the copolymer terminal groups.

In another embodiment, the invention provides a zwitterionic/hydrophobic copolymer having formula (III):

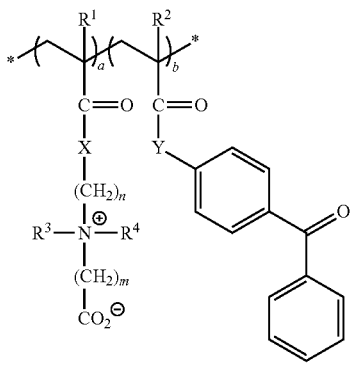

(III)

wherein
$R_1$ and $R_2$ are independently —$(CH_2)_xH$, where x is an integer from 0 to 20;
$R_3$ and $R_4$ are independently —$(CH_2)_xH$, where x is an integer from 0 to 20;
X is O or NH;
Y is O or NH;
n is an integer from 1 to 20;
m is an integer from 1 to 20;

a is from about 0.10 to about 0.90 mole percent;
b is about 0.10 to about 0.90 mole percent;
a+b is 1.0; and
* represents the copolymer terminal groups.

In a further embodiment, the invention provides a zwitterionic/hydrophobic copolymer having formula (IV):

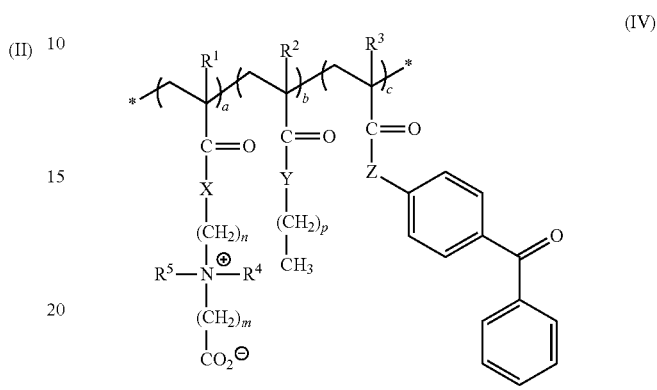

(IV)

wherein
$R_1$, $R_2$, and $R_3$ are independently —$(CH_2)_xH$, where x is an integer from 0 to 20;
$R_4$ and $R_5$ are independently —$(CH_2)_xH$, where x is an integer from 0 to 20;
X is O or NH;
Y is O or NH;
Z is O or NH;
n is an integer from 1 to 20;
m is an integer from 1 to 20;
p is an integer from 0 to 20;
a is from about 0.10 to about 0.90 mole percent;
b is about 0.05 to about 0.95 mole percent;
c is from about 0.05 to about 0.95 mole percent;
a+b+c is 1.0; and
* represents the copolymer terminal groups.

In further aspects, the invention provides coating compositions that include the zwitterionic copolymers and coated surfaces prepared using the zwitterionic copolymers and coating compositions. In certain embodiments, the coating composition includes a zwitterionic copolymer as described herein and optionally a carrier. In certain embodiments, the coating includes a zwitterionic copolymer as described herein or is derived from a zwitterionic copolymer as described herein (e.g., photocrosslinked zwitterionic copolymer).

In certain embodiments, the invention provides a substrate having at least a portion or all of its surface coated with a zwitterionic copolymer of the invention. Suitable surfaces include hydrocarbon-based surfaces and plastic surfaces. Representative surfaces include polyolefin, polyester, polycarbonate, polyurethane (PU), polysulfone (PSF), poly(ether sulfone) (PES), polyamide, polyacrylic, polyimide, aromatic polyester, polyethylene (PE), polypropylene (PP), polystyrene (PS), poly(ethylene terephthalate) (PET), poly(vinyl chloride) (PVC), poly(dimethyl siloxane) (PMDS), poly(vinylidiene fluoride) (PVDF), poly(lactic acid) (PLA), and poly(methyl methacrylate) (PMMA) surfaces. In certain embodiments, the surface is a polyvinyl chloride surface or a polyurethane surface. In other embodiments, the surface is a cellulose or cellulose acetate surface.

In certain embodiments, the substrate is PVC tubing, polyurethane tubing, a polysulfone dialysis membrane, or a hydrocarbon-based membrane container.

In certain embodiments, the substrate is a medical device having at least a portion or all of its surface coated with a zwitterionic copolymer as described herein.

In certain embodiments, the device is an implanted/unimplanted medical device from Class I, Class II, or Class III. In certain embodiments, the device is a plate, a dish, a tube, a tip, a catheter, an artificial blood vessel, an artificial heart, or an artificial lung. In other embodiments, the device is a hemodialyzer, PVC tubing, or polyurethane tubing.

In another aspect of the invention, methods for using the zwitterionic copolymers are provided.

In one embodiment, the invention provides a method for coating a surface of a substrate, comprising contacting the surface with a composition comprising a zwitterionic copolymer of the invention as described herein.

In a related embodiment, the invention provides a method for coating a surface of a substrate, comprising:
  (a) coating at least a portion of a surface of a substrate with a composition comprising a zwitterionic copolymer as described herein; and
  (b) irradiating the surface of the substrate with light effective to crosslink the copolymer.

In another embodiment, the invention provides a method for rendering a surface of a substrate nonfouling, comprising coating at least a portion of the surface with a composition comprising a zwitterionic copolymer as described herein.

In a related embodiment, the invention provides a method for rendering a surface of a substrate nonfouling, comprising:
  (a) coating at least a portion of a surface of a substrate with a composition comprising a zwitterionic copolymer as described herein; and
  (b) irradiating the surface of the substrate with light effective to crosslink the copolymer.

In a further embodiment, the invention provides a method for inhibiting blood protein adsorption on a surface of a substrate, comprising coating at least a portion of the surface with a composition comprising a zwitterionic copolymer as described herein.

In a related method, the invention provides a method for inhibiting blood protein adsorption on a surface of a substrate, comprising:
  (a) coating at least a portion of a surface of a substrate with a composition comprising a zwitterionic copolymer as described herein; and
  (b) irradiating the surface of the substrate with light effective to crosslink the copolymer.

In another embodiment, the invention provides a method for inhibiting or preventing leaching of a plasticizer from a surface of a substrate, comprising:
  (a) coating at least a portion of a surface of a substrate with a composition comprising a zwitterionic copolymer as described herein to provide a coated surface.

In a related embodiment, the invention provides a method for inhibiting or preventing leaching of a plasticizer from a surface of a substrate, comprising:
  (a) coating at least a portion of a surface of a substrate with a composition comprising a photoreactive zwitterionic copolymer as described herein to provide a coated surface; and
  (b) irradiating the coated surface with light effective to crosslink the copolymer on the surface, thereby providing a coated surface effective for inhibiting or preventing leaching of a plasticizer from the surface.

In certain of the above methods, contacting or coating the surface with the composition comprises dipping the surface into the composition (e.g., zwitterionic copolymer). In other embodiments, contacting or coating the surface with the composition comprises spraying, spinning, brushing, or rolling the composition onto the surface.

Suitable surfaces include hydrocarbon-based surfaces and plastic surfaces. Representative surfaces include polyolefin, polyester, polycarbonate, polyurethane (PU), polysulfone (PSF), poly(ether sulfone) (PES), polyamide, polyacrylic, polyimide, aromatic polyester, polyethylene (PE), polypropylene (PP), polystyrene (PS), poly(ethylene terephthalate) (PET), poly(vinyl chloride) (PVC), poly(dimethyl siloxane) (PMDS), poly(vinylidiene fluoride) (PVDF), poly(lactic acid) (PLA), and poly(methyl methacrylate) (PMMA) surfaces. In certain embodiments, the surface is a polyvinyl chloride surface or a polyurethane surface. In other embodiments, the surface is a cellulose or cellulose acetate surface.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 3 is a table that summarizes the characteristics of representative carboxybetaine random copolymers of the invention.

FIG. 17F adsorption of 100% human serum under static conditions tested using a Micro BCA protein assay kit. Uncoated: commercial PVC tubing. PCB-coated: PCB-coated PVC tubing soaked in PBS (1×, pH 7.4) at 37° C. for 1 week or 3 weeks. Results are expressed as mean±SD (n=3; *p<0.001, and **p>0.05).

DETAILED DESCRIPTION OF THE INVENTION

Figure 1:
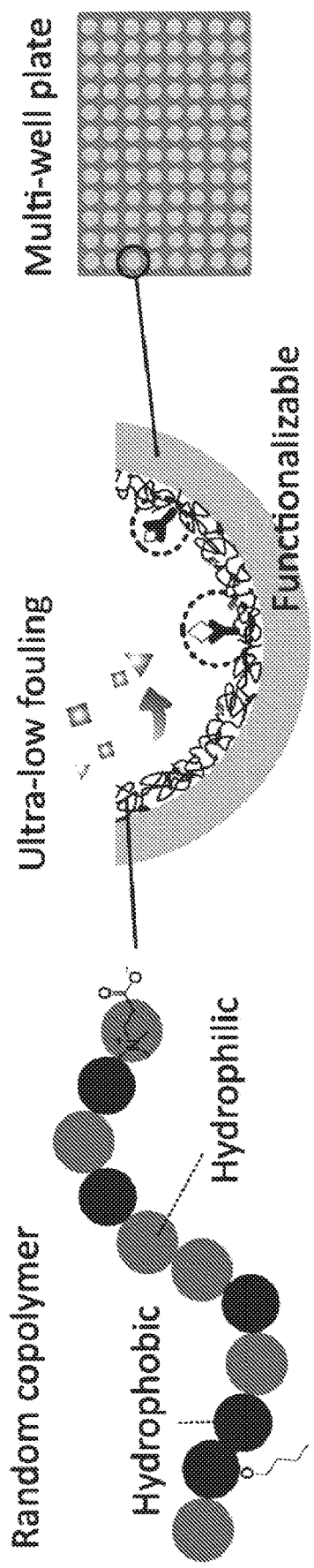
FIG. 1 is a schematic representation for the preparation of an ultra-low fouling and functionalizable carboxybetaine (CB) polymer surface in accordance with the present invention.

The present invention provides zwitterionic copolymers and their use in coatings to impart non-fouling and functionality to surfaces, particularly surfaces of blood-contacting medical devices. The invention provides zwitterionic copolymers functionalized for their immobilization of surfaces, coating compositions that include the zwitterionic copolymers, surface coatings prepared from the zwitterionic copolymers, substrates having surfaces modified by the zwitterionic copolymers, and medical devices having surfaces modified by the zwitterionic copolymers.

Zwitterionic Copolymers

In one aspect, the invention provides zwitterionic copolymers functionalized for their immobilization on surfaces.

In certain embodiments, the invention provides a copolymer useful for coating a surface, the copolymer comprising first repeating units and second repeating units, wherein each of the first repeating units comprises a pendant zwitterionic group, and wherein each of the second repeating units comprises a pendant photoreactive group effective for crosslinking the copolymer to a plastic surface. In certain of these embodiments, the copolymer further comprises third repeating units, wherein each of the third repeating units comprises a hydrophobic group effective for adsorbing the copolymer to a plastic surface.

In certain embodiments, the invention provides a copolymer useful for coating a surface, the copolymer comprising first repeating units, optional second repeating units, and optional third repeating units, provided that the copolymer includes at least first repeating units and optional second repeating units or at least first repeating units and optional third repeating units, wherein each of the first repeating units comprises a pendant zwitterionic group, wherein each of the second repeating units comprises a pendant photoreactive group effective for crosslinking the copolymer to a surface, and wherein each of the third repeating units comprises a pendant hydrophobic group effective for adsorbing the copolymer to a surface. In these embodiments, the copolymer is represented by formula (I):

$$*-(P_1)_a(P_2)_x(P_3)_y-* \tag{1}$$

wherein $P_1$ is a repeating unit having a pendant zwitterionic group, $P_2$ is a repeating unit having a pendant hydrophobic group, $P_3$ is a repeating unit having a pendant photoreactive group, a is from about 0.10 to about 0.90 mole percent, x is 0 to about 0.95 mole percent, y is 0 to about 0.95 mole percent, with the proviso that x and y are not both 0, and a+x+y is 1.0.

The copolymers of the present invention comprise repeating units derived from polymerizable monomers and comonomers. In the copolymer represented by formula (I), repeating units $P_1$, $P_2$, and $P_3$ taken together form the copolymer's backbone. Each repeating unit includes either a zwitterionic group, a hydrophobic group, or a photoreactive group. In certain embodiments, each of the zwitterionic group, the hydrophobic group, and the photoreactive group are pendant groups (i.e., these groups are pendant from the copolymer backbone). In certain of these embodiments, the copolymer having pendant groups are prepared from polymerizable monomers and comonomers having the pendant groups.

The nature of the copolymer's backbone is not critical so long as the backbone does not adversely affect the copolymer's overall performance; the performance of the copolymer's zwitterionic groups, hydrophobic groups, and photoreactive groups. Suitable copolymer backbones include polyesters, polycarbonates, polyurethanes, polyureas, polysulfides, polysulfones, polyimides, polyepoxies, aromatic polyesters, cellulosics, fluoropolymers, polyacrylics, polyamides, polyanhydrides, polyethers, vinyl polymers, phenolics, elastomers and other addition polymers. Representative copolymer backbones include those described in detail herein.

As used herein, the term "zwitterionic group" refers to a group that includes at least two functional groups, one having a positive and one having a negative electrical charge and the net charge of the group is zero. Representative zwitterionic groups include carboxybetaine (CB) groups, sulfobetaine (SB) groups, phosphobetaine (PHB) groups, and phosphorylcholine (PC) groups. The zwitterionic groups impart low-fouling and functionalizable properties to surfaces that are treated or coated with the copolymer.

The term "hydrophobic group" refers to a group that is hydrocarbon and non-polar in nature. The hydrophobic groups serve to facilitate binding of the copolymer to the surfaces treated with the copolymer (e.g., via hydrophobic-hydrophobic interaction). The nature of the copolymer's hydrophobic groups is not critical so long as the group achieves binding of the copolymer to the surface sufficient to the intended use of the treated or coated surface and does not adversely affect performance of the copolymer's zwitterionic groups or photoreactive groups. Suitable hydrophobic groups include groups that include hydrocarbon groups, such as alkyl and alkylene groups having two or more, three or more, or four or more carbons (e.g., ethyl, ethylene, propyl, propylene, butyl, butylene groups). Representative hydrophobic groups include C3-C20 alkyl groups (e.g., n-butyl), benzene ring-containing groups (e.g., phenyl), fluorinated alkyl (e.g., trifluoromethyl) and fluorinated aryl groups.

The term "photoreactive group" refers to a group that becomes reactive to crosslinking upon irradiation with ultraviolet light. The pendant photoreactive groups (i.e., crosslinking groups) serve to facilitate binding of the copolymer to the surfaces treated with the copolymer. The nature of the copolymer's photoreactive groups is not critical so long as the group achieves copolymer crosslinking on the surface sufficient to stabilize the copolymer on the treated or coated surface and does not adversely affect performance of the copolymer's zwitterionic groups or hydrophobic groups. Suitable photoreactive groups include groups that include groups that affect crosslinking upon irradiation with the appropriate wavelength of light (e.g., ultraviolet, 250-370 nm). Suitable photoreactive groups are derived from aromatic ketones, azides, diazo diazirine groups. Representative photoreactive groups include benzophenones, acetophenones, phenylazides, aryl azides (e.g., phenylazide), azidomethyl-coumarins, anthraquinones, and psoralen derivatives.

The photoreactive groups of the zwitterionic polymers described herein are effective to crosslink the copolymers. The photoreactive groups are also effective to crosslink the zwitterionic copolymer to the surface on which the copolymer has been coated where the surface includes C—H reactive toward the photoreactive groups. Representative surfaces to which the zwitterionic copolymers can be crosslinked include C—H containing surfaces such as polyethylene, polystyrene, polyethylene terephthalate, polyvinyl chloride, and cyclic polyolefin surfaces. The photoreactive zwitterionic copolymers described herein are not crosslinked to metal, metal alloy, or ceramic surfaces that do not include C—H reactive groups. The use of photoreactive zwitterionic copolymers as described herein provides surfaces having durable network polymer films.

In other embodiments, the zwitterionic copolymer includes crosslinking groups that are activated by light and heat. In further embodiments, the copolymer includes crosslinking groups that are activated by heat.

The copolymers of the invention and those useful in the methods of the invention include random copolymers prepared by copolymerization of comonomers (e.g., copolymerization of a polymerizable monomer that bears a zwitterionic group, a polymerizable monomer that bears a hydrophobic group, and a polymerizable monomer that bears a photoreactive group (e.g., copolymers of formulae (I), (II), (III), and (IV)). In the copolymer formulae described and shown herein, repeating units that include zwitterionic groups, repeating units that include hydrophobic groups, and repeating units that include photoreactive groups are depicted. See, for example, formulae (I), (II), III), and (IV). The depictions are not intended to limit the nature of the copolymer; the copolymers depicted may be random copolymers having the specified number of repeating units (e.g., for formula (I), "a" for repeating units that include zwitterionic groups, "x" for repeating units that include hydrophobic groups, and "y" for repeating units that include photoreactive groups).

The copolymers described herein may include additional repeating units so long as the additional repeating units do not interfere or adversely affect the properties of the copolymer's intended uses, as noted above. These copolymers of the invention "comprise" repeating units that include, for example, zwitterionic groups, repeating units that include hydrophobic groups, and repeating units that include photoreactive groups, as well as other repeating units.

In certain embodiments, the copolymers of the invention only include, for example, repeating units that include zwitterionic groups, repeating units that include hydrophobic groups, and repeating units that include photoreactive groups. These copolymers of the invention "consist of" repeating units that include zwitterionic groups, repeating units that include hydrophobic groups, and repeating units that include photoreactive groups, and do not include other repeating units.

The zwitterionic copolymers of the invention include zwitterionic groups up to about 90 mol %. For zwitterionic copolymers of the invention that include hydrophobic groups, the copolymers include hydrophobic groups up to about 70 mol %. For zwitterionic copolymers of the invention that include photoreactive groups, the copolymers include photoreactive groups up to about 30 mol %.

The zwitterionic copolymers of the invention have a weight average molecular weight from about 1,000 to about 2,000,000.

Zwitterionic/Hydrophobic Copolymers

In one embodiment, the invention provides copolymers having zwitterionic groups and hydrophobic groups, each pendant from the copolymer's backbone (i.e., zwitterionic/hydrophobic copolymers). The pendant zwitterionic groups impart low-fouling and functionalizable properties to surfaces that are treated or coated with the copolymer. The pendant hydrophobic groups serve to facilitate binding of the copolymer to the surfaces treated with the copolymer (e.g., via hydrophobic-hydrophobic interaction). The relative amounts of zwitterionic groups and hydrophobic groups pendant from the copolymer's backbone are adjustable via copolymer synthesis to achieve the desired degree of low-fouling and functionalization and binding of the copolymer to the surface, each of which can be tuned depending on the nature (e.g., composition) of the surface to be treated or coated.

In certain aspects, the present invention provides a simple, yet effective modification approach for hydrophobic materials using amphiphilic zwitterionic (e.g., carboxybetaine, CB) random copolymers via a dip-coating technique. By adjusting the composition of the hydrophilic and the hydrophobic units in this series of amphiphilic copolymers, the effect of polymeric amphiphilicity on nonfouling capability was explored and established the optimal compositions for surface coating. 100% human serum adsorption was measured on CB random copolymer coated surfaces. Results were compared to those of a commercial 96-well plate with an "ultra-low attachment surface." Furthermore, the CB copolymer surface was subsequently functionalized with anti-fibrinogen by covalent bonding between the carboxyl group within CB and the amino group within the antigen. Thus, this CB polymer material and modification technique is promising for a wide range of applications, including nonfouling medical devices and medical diagnostics.

In one embodiment, the invention provides a copolymer of formula (II):

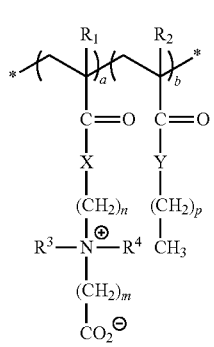
(II)

wherein
$R_1$ and $R_2$ are independently —$(CH_2)_xH$, where x is an integer from 0 to 20;
$R_3$ and $R_4$ are independently —$(CH_2)_xH$, where x is an integer from 0 to 20;
X is O or NH;
Y is O or NH;
n is an integer from 1 to 20;
m is an integer from 1 to 20;
p is an integer from 0 to 20;
a is from about 0.10 to about 0.90 mole percent;
b is about 0.10 to about 0.90 mole percent;
a+b is 1.0; and
* represents the copolymer terminal groups.

In certain of these embodiments, $R_1$ and $R_2$ are independently selected from the group consisting of hydrogen and methyl.

In certain embodiments, $R_3$ and $R_4$ are independently selected from the group consisting of hydrogen and C1-C3 alkyl.

In certain embodiments, n is 1, 2, 3, 4, 5, or 6. In some embodiments, n is 2 or 3.

In certain embodiments, m is 1, 2, 3, 4, 5, or 6. In some embodiments, m is 1 or 2.

In certain embodiments, p is 1, 2, 3, 4, 5, or 6. In some embodiments, p is 3.

In certain embodiments, a is from about 0.20 to about 0.40 mole percent. In some embodiments, a is about 0.30 mole percent.

In certain embodiments, b is about 0.60 to about 0.80 mole percent. In some embodiments, b is about 0.70 mole percent.

In certain embodiments, $R_1$ is hydrogen or methyl, $R_2$ is hydrogen or methyl, $R_3$ and $R_4$ are methyl, and X is NH and Y is O.

In other embodiments, $R_1$ is hydrogen or methyl, $R_2$ is hydrogen or methyl, $R_3$ and $R_4$ are methyl, X is O, and Y is O.

In further embodiments, $R_1$ is hydrogen, $R_2$ is methyl, $R_3$ and $R_4$ are methyl, X is NH, Y is O, n is 3, m is 1 and p is 2. In certain of these embodiments, a is about 0.30 mole percent.

In other embodiments, $R_1$ is methyl, $R_2$ is methyl, $R_3$ and $R_4$ are methyl, X is O, Y is O, n is 2, m is 2 and p is 2. In certain of these embodiments, a is about 0.30 mole percent.

The following is a description of the preparation, characterization and use of representative zwitterionic/hydrophobic copolymers of the invention and their use in the compositions and methods of the invention.

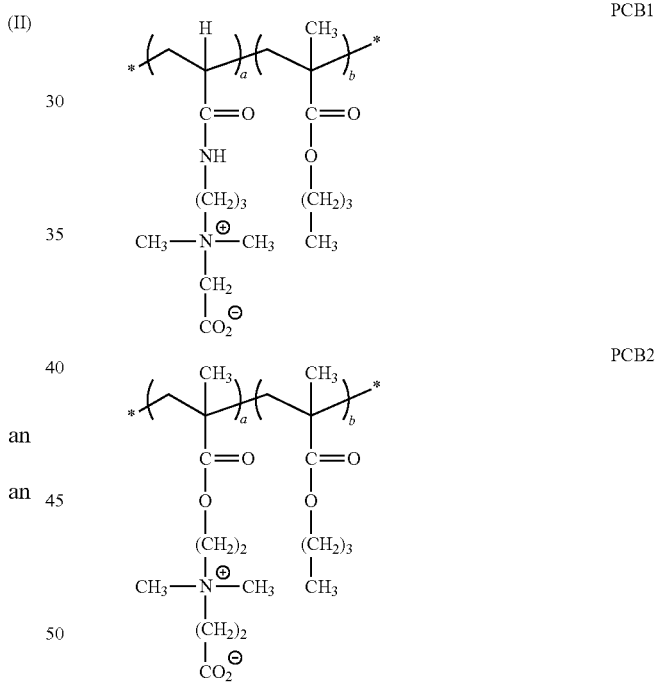

The invention provides an effective surface modification approach to impart hydrophobic surfaces with super-hydrophilicity using ultra-low fouling/functionalizable carboxybetaine (CB) copolymers via a dip-coating technique. A series of CB random copolymers with varying amphiphilicities was synthesized and coated on hydrophobic polypropylene (PP) and polystyrene (PS) surfaces. Nonfouling capability of each coating was screened by enzyme-linked immunosorbent assay (ELISA), and further comprehensively assessed against 100% human serum by Micro BCA protein assay kit. The random copolymer containing about 30 mol % of CB unit showed superhydrophilicity with the highest air contact angle of more than 165° in DI water and the best nonfouling capability against 100% human blood serum. Surfaces of a 96-well plate coated with the optimal CB random copolymer showed significantly better nonfouling capability than those of a commercial 96-well plate with an ultra-low attachment surface. Adhesion of mouse embryonic fibroblast cells (NIH3T3) was completely inhibited on surfaces coated with CB random copolymers. Furthermore, the optimal nonfouling CB copolymer surface was functionalized with an antigen via covalent bonding where its specific interactions with its antibody were verified. Thus, this CB random copolymer is capable of imparting both ultra-low fouling and functionalizable capabilities to hydrophobic surfaces for blood-contacting devices.

The following describes representative polycarboxybetaines, their properties, their use in preparing non-fouling surfaces, and the properties of the coated surfaces.

Figure 2A:
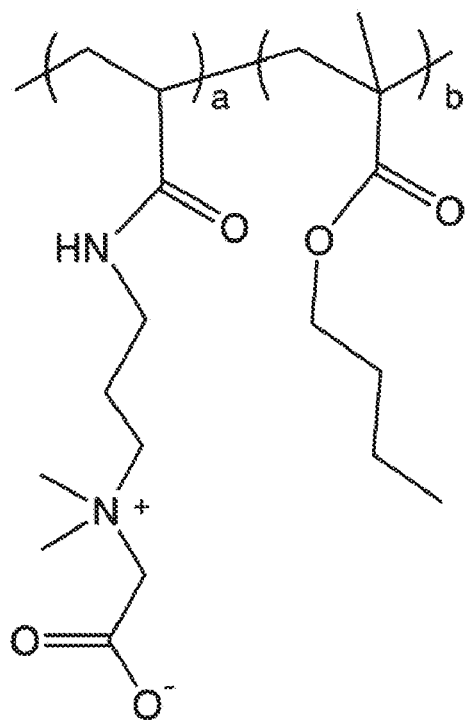
FIGS. 2A and 2B illustrate the chemical structures of representative carboxybetaine (CB) random copolymers of the invention: poly(CB1-co-BMA) (PCB1) (FIG. 1A), and poly(CB2-co-BMA) (PCB2) (FIG. 1B). The numerals 1 and 2 after CB refer to the number of carbons between the carboxyl group and the quaternary ammonium cation. The composition of each unit in the copolymer was calculated through integration of characteristic protons in $^1$H-NMR spectrum, where 3.82 ppm (—$CH_2$—, 2H) for the CB1 unit, 2.42 ppm (—$CH_2$—, 2H) for the CB2 unit, and 1.45-1.63 ppm (—$CH_2$—, 4H) for the BMA unit. The carboxyl groups in PCB2 can be activated by EDC/NHS chemistry, and covalently bond with amino groups of, for example, proteins, enzyme, and aptamer/oligonucleotides. CB1 is carboxybetaine acrylamide, 1-carboxy-N,N-dimethyl-N-(3'-acrylamidopropyl) ethanaminium inner salt; CB2 is carboxybetaine methacrylate, 2-carboxy-N,N-dimethyl-N-(2'-methacryloyloxyethyl) ethanaminium inner salt; and BMA is n-butyl methacrylate.
Figure 2B:
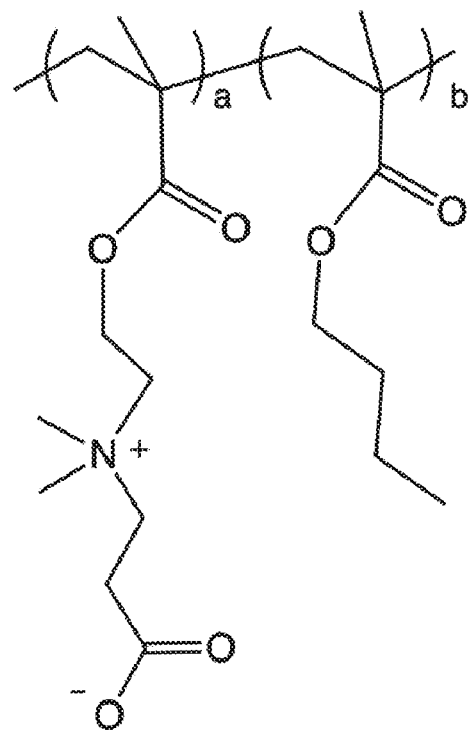

Synthesis of Random Copolymers. Polyolefins have been widely manufactured for biomedical applications. However, these hydrophobic polymeric hydrocarbon-based materials will trigger non-specific protein adsorption, platelet activation, blood clotting, thrombogenesis and other biofouling-associated issues. For practical applications, it is highly desirable to use the simplest approach to achieve the set goals. Free radical polymerization method is one of the most common and useful approaches for making polymers from small-scale laboratory trial to large-scale industrial application, particularly for polymerization of vinyl monomers. Amphiphilic random copolymers were synthesized through a conventional free radical polymerization method using AIBN as a thermal free radical initiator. Viscosity of these reaction solutions gradually increased along with the processing of polymerization at 65° C., indicating the conversion of monomers to copolymers. From the integral values of characteristic peaks in $^1$H-NMR spectra, the unit fraction of each monomer was obtained: 3.82 ppm (—$CH_2$—, 2H) for the CB1 unit, 2.42 ppm (—$CH_2$—, 2H) for the CB2 unit, and 1.45-1.63 ppm (—$CH_2$—, 4H) for the BMA unit. The chemical structures and synthetic details about these polymers are shown in FIGS. 2A and 2B and Table 1 (FIG. 3), respectively. Hydrophilic CB unit and hydrophobic BMA unit in the polymer chain were randomly distributed, with a total composition approximately equal to that of the monomer feed solutions. The solubility of CB random copolymers in an aqueous solution mainly depends on the CB unit composition. Copolymers containing more than 30 mol % of CB unit will be easily dissolved in an aqueous solution, while less than 30 mol % will become water-insoluble (Table 1). Thus, water-insoluble CB copolymer containing 30 mol % CB unit is the best coating material among these copolymers. These results match with other random copolymers containing phosphorylcholine group, which has been widely utilized for surface modification of biomedical devices.

Figure 4:
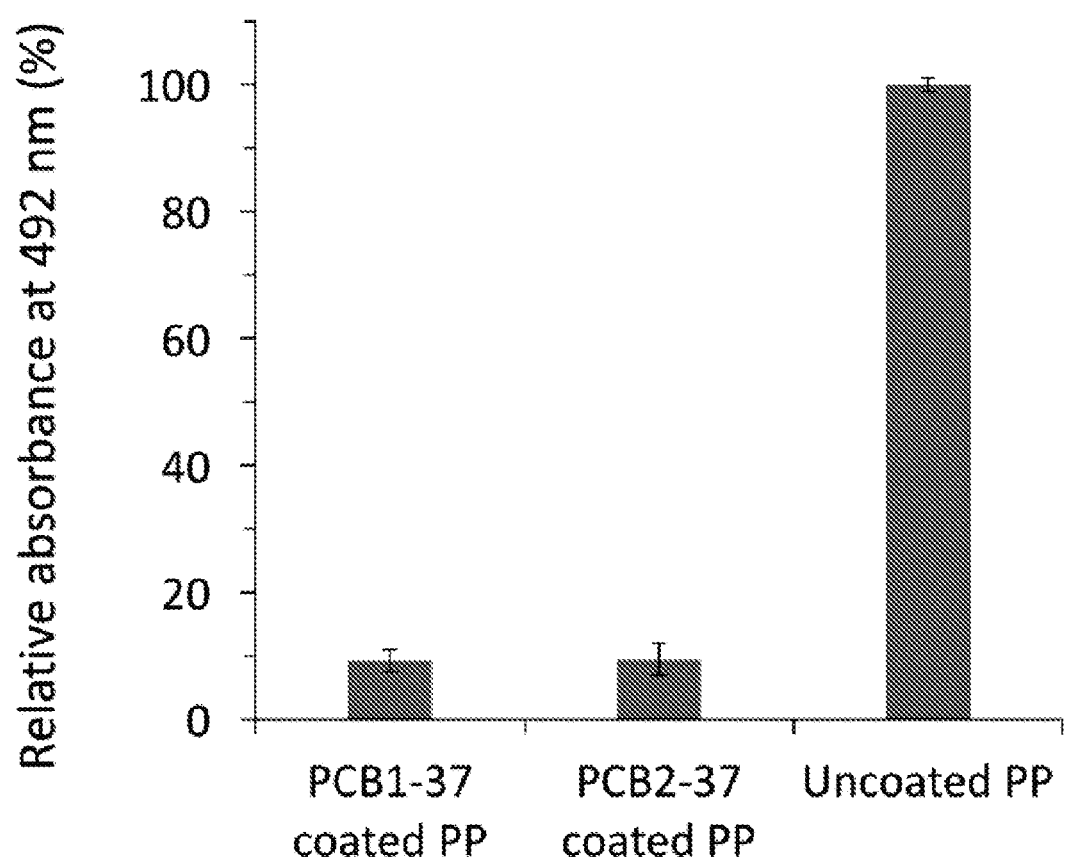
FIG. 4 compares relative adsorption of fibrinogen (1.0 mg/mL, 1×PBS, pH 7.4) on a PP surface coated with representative carboxybetaine random copolymers of the invention, PCB1-37 and PCB2-37, at 0.5 wt % concentration.
Figure 5B:
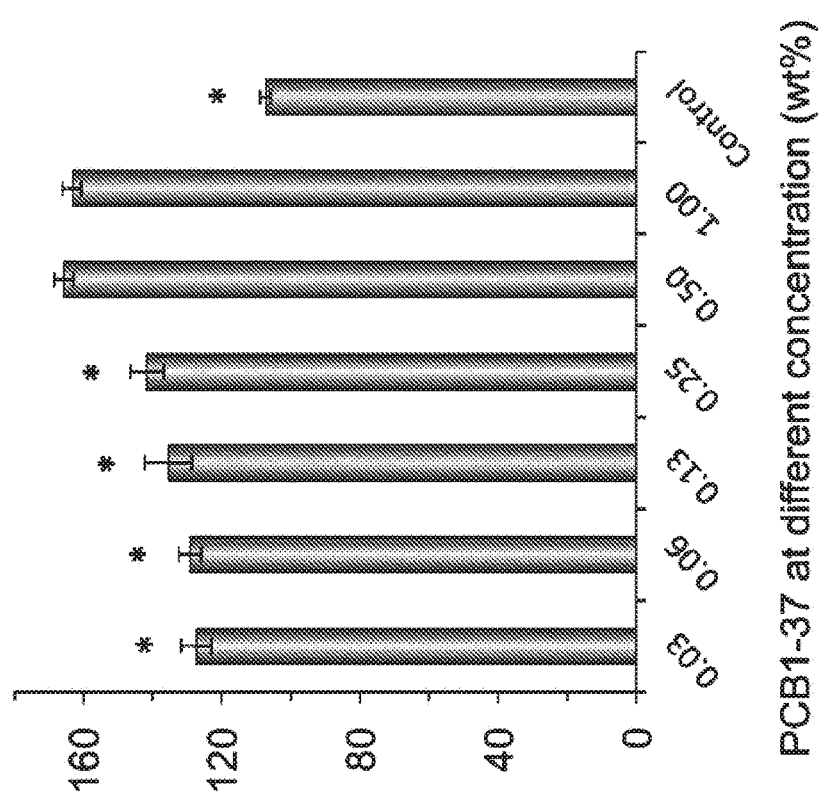
FIGS. 5A and 5B compares air contact angle measured in distilled water on polypropylene (PP) substrates modified with different CB random copolymers (5A) and PCB1-37 (5B) at different concentrations. The numeral designation refers to the molar ratio of two units in copolymers (i.e., 28 in PCB1-28 indicates that the molar ratio of CB/BMA in this copolymer is 2/8). Single asterisk (*) in 5A indicates statistically significant difference ($p<0.05$, n=5) compared to PCB1-37; and single asterisk (*) in 5B indicates statistically significant difference ($p<0.05$, n=5) compared to 0.50 wt %.
Figure 5A:
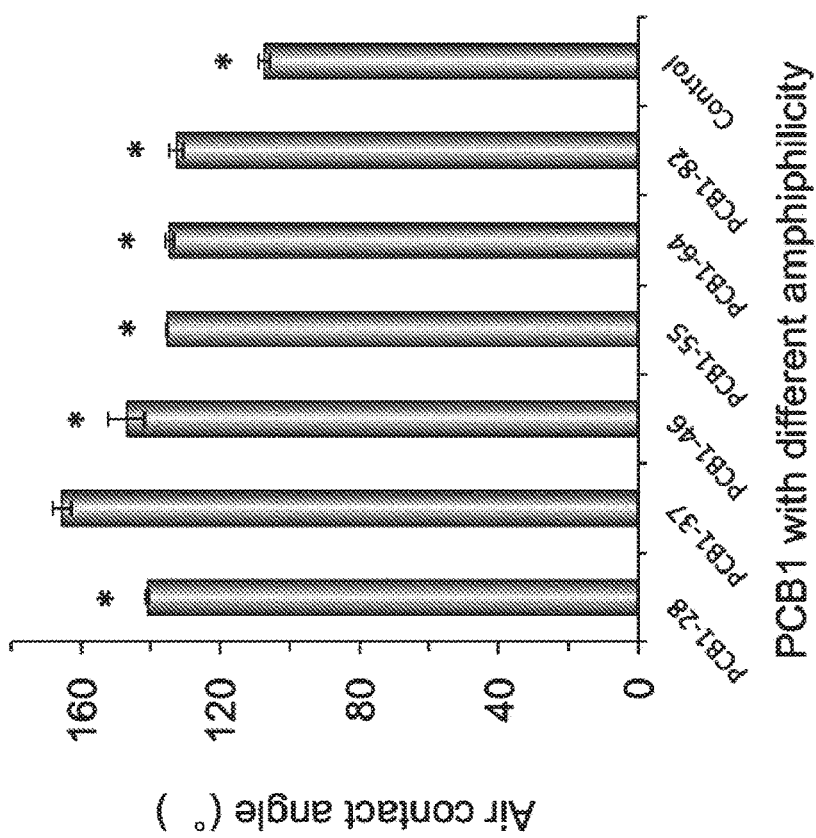
Figures 6A, 6B:
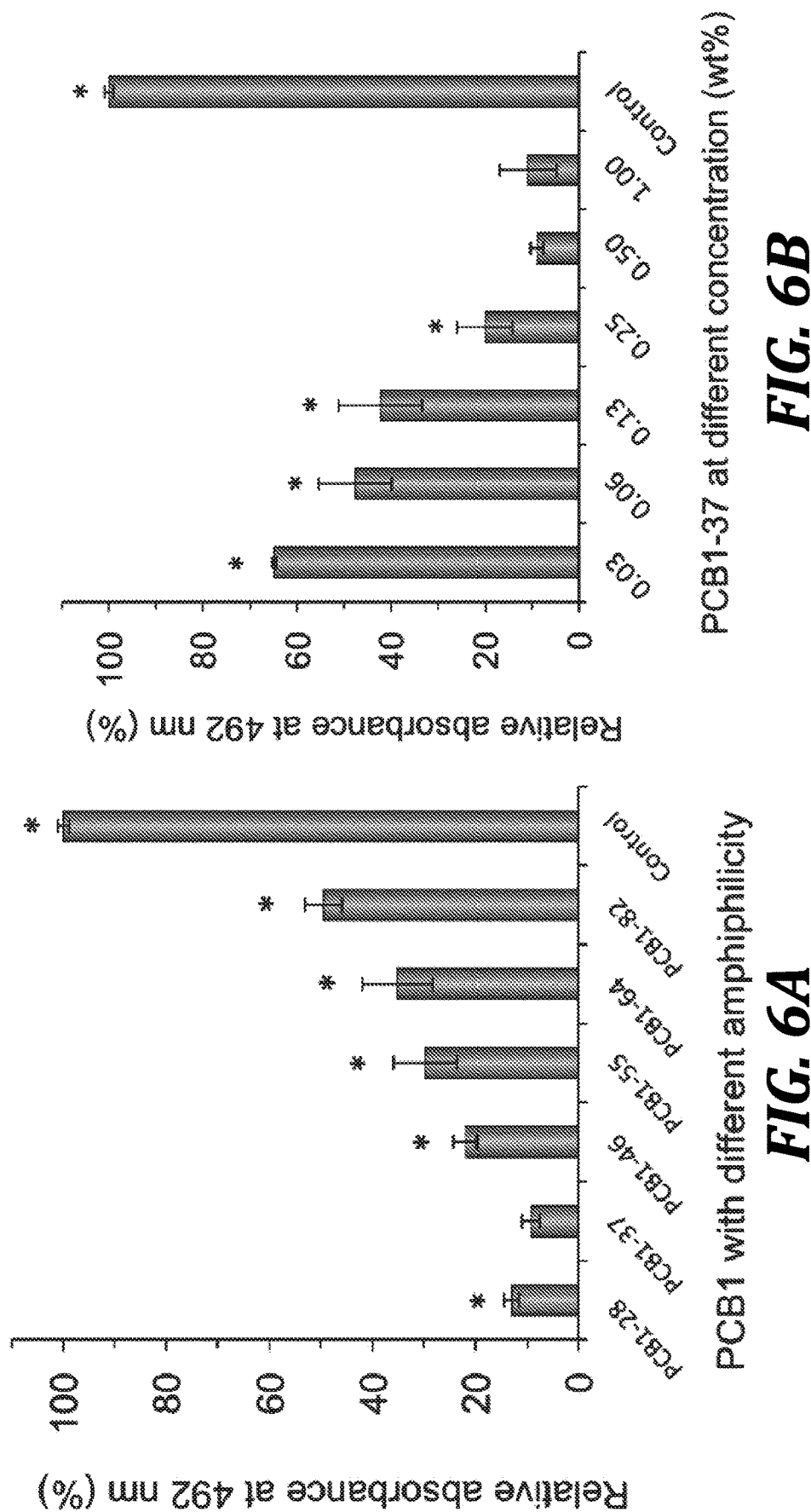
FIGS. 6A and 6B compare relative adsorbed amount of fibrinogen (1.0 mg/mL, 1×PBS, pH 7.4) on a PP surface coated with different CB random copolymers (6A) and PCB1-37 (6B) at different concentrations. The numeral designation refers to the molar ratio of two units in copolymers (i.e., 28 in PCB1-28 indicates that the molar ratio of CB/BMA in this copolymer is 2/8). Single asterisk (*) in 5A indicates statistically significant difference (p<0.05, n=5) compared to PCB1-37; and single asterisk (*) in 5B indicates statistically significant difference (p<0.05, n=5) compared to 0.50 wt %. Relative absorbance at 492 nm indicates the relative adsorbed amount of fibrinogen.

Air Contact Angles and Screening of Coatings for Protein Adsorption. Amphiphilic CB copolymers with different hydrophobic/hydrophilic compositions can impart different nonfouling capabilities. Hydrophilic (CB) unit can promote ionic-induced hydration that can bind water molecules strongly to enhance nonfouling capability. However, strong hydration force may cause the detachment of coating materials from the surface. Hydrophobic (BMA) unit will bind the hydrophobic substrate surface strongly, to stabilize the CB unit on the surface in an aqueous solution and increase coating durability. Thus, it is necessary to prepare these coating random polymers with an appropriate molar ratio of CB/BMA so as to maximize both nonfouling and surface-binding properties. Results of air contact angle in FIGS. 5A and 5B showed that the copolymers containing about 30 mol % of CB unit exhibits superhydrophilicity with an air contact angle up to 165°. Its superhydrophilicity is related to its excellent performance as shown in FIG. 6A, where the random polymer with about 30 mol % of CB unit has the strongest protein repelling capability. Other polymers with higher CB compositions are easily detached from PP surfaces due to their high solubility in an aqueous solution. Although PCB1-28 and PCB1-37 are both water-insoluble, higher CB compositions can increase their repelling capability against non-specific protein adsorption. In addition, the concentration of the polymer solution is another essential factor that affects the coated amount of zwitterionic polymer and thus nonfouling capability. As shown in FIG. 6B, the absorbed amount of Fg decreased dramatically along with increasing of polymer concentration from 0.03 to 0.5 wt %, while above 0.5 wt % fouling reached a saturated relative low level that less than 15% compared to uncoated substrate. In addition, both PCB1-37 and PCB2-37 polymers showed similar nonfouling properties (FIG. 4).

The stability of CB polymer (about 30 mol % of CB unit) coating layer was confirmed under dry condition by comparing the polymer thickness of CB coated gold chips before and after soaking into PBS (1×, pH 7.4), using a spectroscopic ellipsometer. The thicknesses of modified CB polymer layers on gold substrates were calculated as 29.38±1.10 nm before soaking. This value did not significantly change after the substrates was soaked into PBS for two months when film thickness remained to be 28.80±0.73 nm.

Protein Adsorption from 100% Blood Proteins and Serums. The interactions between blood components and biomaterials may trigger a series of subsequent complex biological responses including protein adsorption, platelet adhesion/activation, blood coagulation and thrombosis. Rapid non-specific adsorption of plasma proteins has been considered as the first event occurring on biomaterial surfaces during blood/material interactions. Thus, it is crucial to evaluate the adsorption of main plasma proteins (e.g., fibrinogen, albumin, and γ-globulin) to understand the blood compatibility of biomaterials. Importantly, 10% diluted single-protein solutions are frequently utilized for this evaluation, but this testing condition is still far from the actual blood environment. As described herein, both 100% single blood proteins and 100% human serums were used. Non-specific protein adsorption amount was tested by Micro BCA protein assay kit.

Figure 7A:
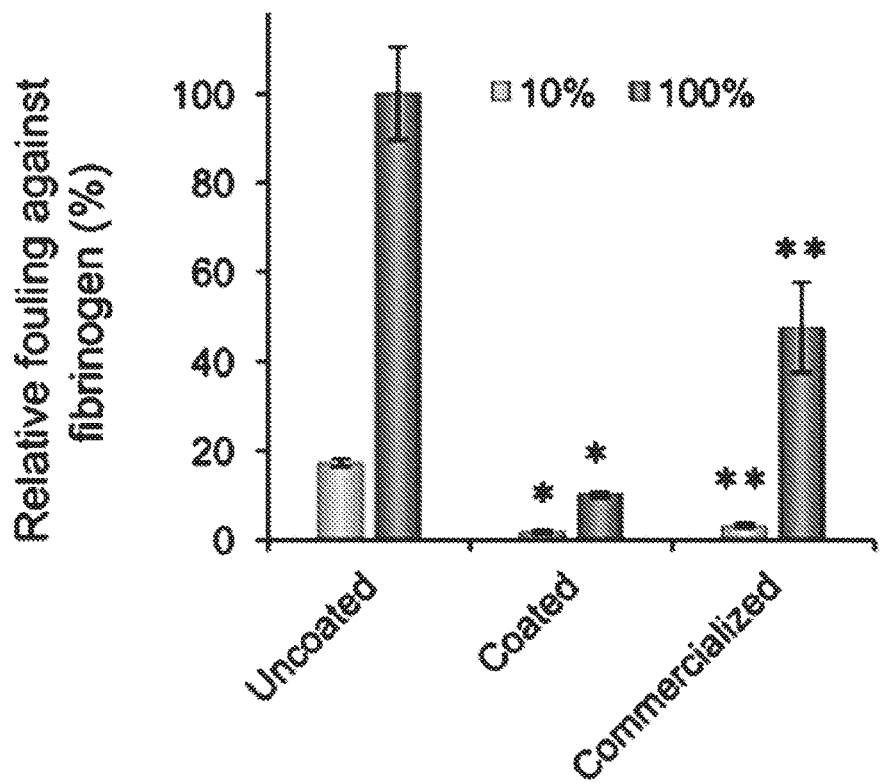
FIGS. 7A-7D compare non-specific protein adsorption against (a) human plasma fibrinogen (Fg) (7A), human serum albumin (HSA) (7B), human blood γ-globulin (7C), and human blood serum (7D) on 96-well plate with three kinds of surfaces: uncoated polystyrene surface, PCB1-37 coated polystyrene surface, and commercial plate with an ultra-low attachment surface (Corning Costar Corp., Corning, N.Y., USA). The Corning ultra-low surface coating is a hydrophilic, neutrally charged coating covalently bound to the polystyrene surface. Both 10% and 100% of single blood proteins and human blood serums were used to evaluate their nonfouling capability. The uncoated surface and the commercial product with an ultra-low attachment surface were utilized as controls. Concentration of 100% of Fg, HSA, and γ-globulin in blood are 3.0, 45, and 16 mg/mL, respectively. Normal human blood serum (pooled mixed gender) was used as received and without dilution. Single asterisk (*) indicates statistically significant difference (p<0.01, n=5) compared to either uncoated surface or commercialized ultra-low attachment surface; double asterisk (**) indicates statistically significant difference (p<0.01, n=5) compared to uncoated surface.
Figure 7B:
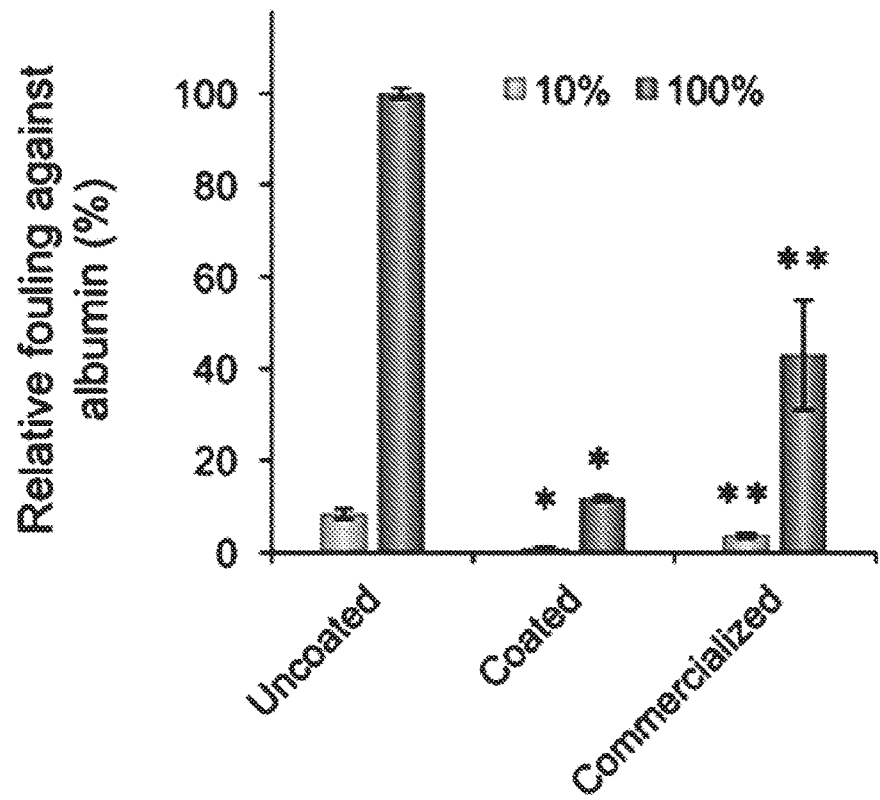
Figure 7C:
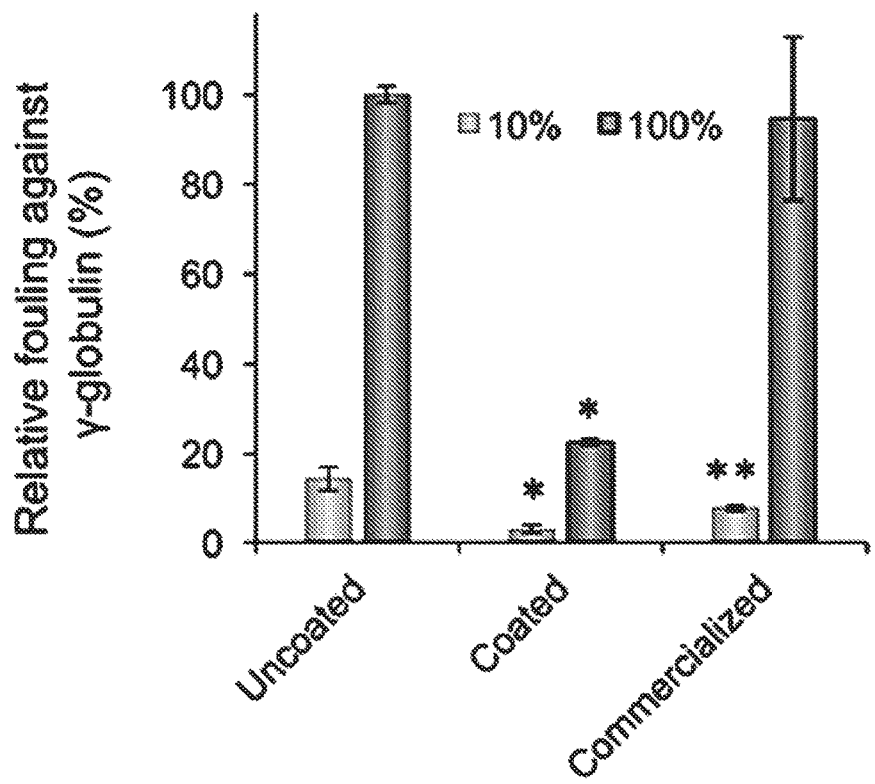
Figure 7D:
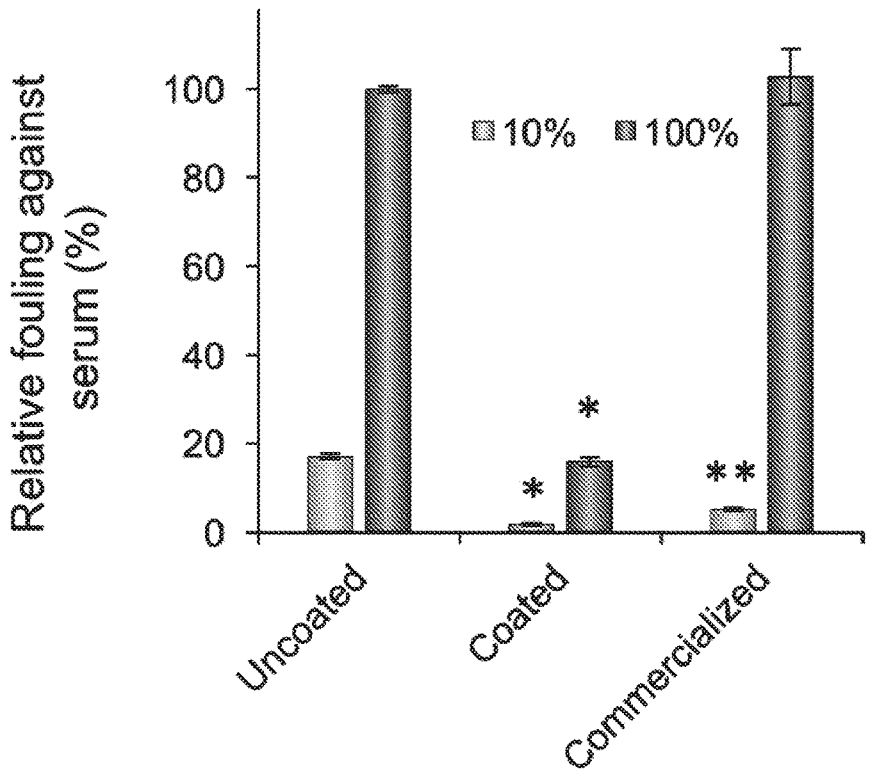

In FIGS. 7A-7D, for CB polymer-coated surfaces, the adsorbed amount of different types of proteins and undiluted serum was significantly reduced compared to uncoated surfaces both at 10% and 100% concentrations, indicating that zwitterionic CB polymer coating layer can impart ultra-low fouling capability to hydrophobic hydrocarbon-based surfaces. Although the commercial 96-well plate with an ultra-low attachment surface can repel protein adsorption from single-protein solutions at lower (10%) concentrations, there is still approximately 50% protein adsorption when protein concentration increases to 100% (FIGS. 7A and 7B). Importantly, although the commercial surface can repel the adsorption of single blood proteins at 10% concentrations, they lost nonfouling capability completely after being soaked in either 100% human serum or 100% γ-globulin environment (FIGS. 7C and 7D).

Figure 8:
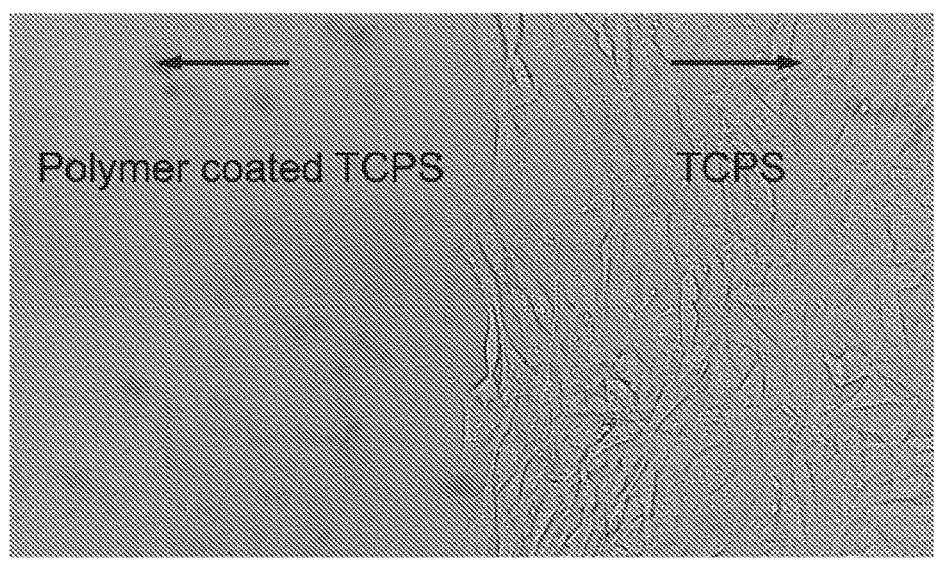
FIG. 8 is compares images of surfaces illustrating adhesion and migration behavior of NIH3T3 mouse embryonic fibroblast cells on the CB polymer (PCB1-37) coated TCPS surface (left) and on the original TCPS surface (right).

Cell adhesion. NIH3T3 cells are able to adhere, proliferate and migrate on a normal tissue culture polystyrene (TCPS) plate. After seeding them onto the surface of TCPS plate with a zwitterionic CB copolymer partially coated, cells will gradually adhere and spread out on TCPS surface. In contrast, most of the cells will remain spherical shape and cannot adhere on the CB copolymer surface. After being cultured for 72 h and slightly rinsed with fresh medium, no adhered cells were observed on the CB copolymer coated surface, while cells proliferated and reached sub-confluent on the normal TCPS surface with a very clear border (FIG. 8). For fibroblast cells, adhesion is essential in maintaining multicellular structure and function, which is important for subsequent proliferation and migration. Fibronectin plays a major role in the adhesion of many cell types, and the adsorption of fibronectin will directly affect cell adhesion to substrate surfaces. Superhydrophilic zwitterionic polymer surfaces have excellent nonfouling capability against non-specific protein, including fibronectin. Thus, fibroblast cell adhesion was completely prevented by the CB polymer coating layer.

Figure 9:
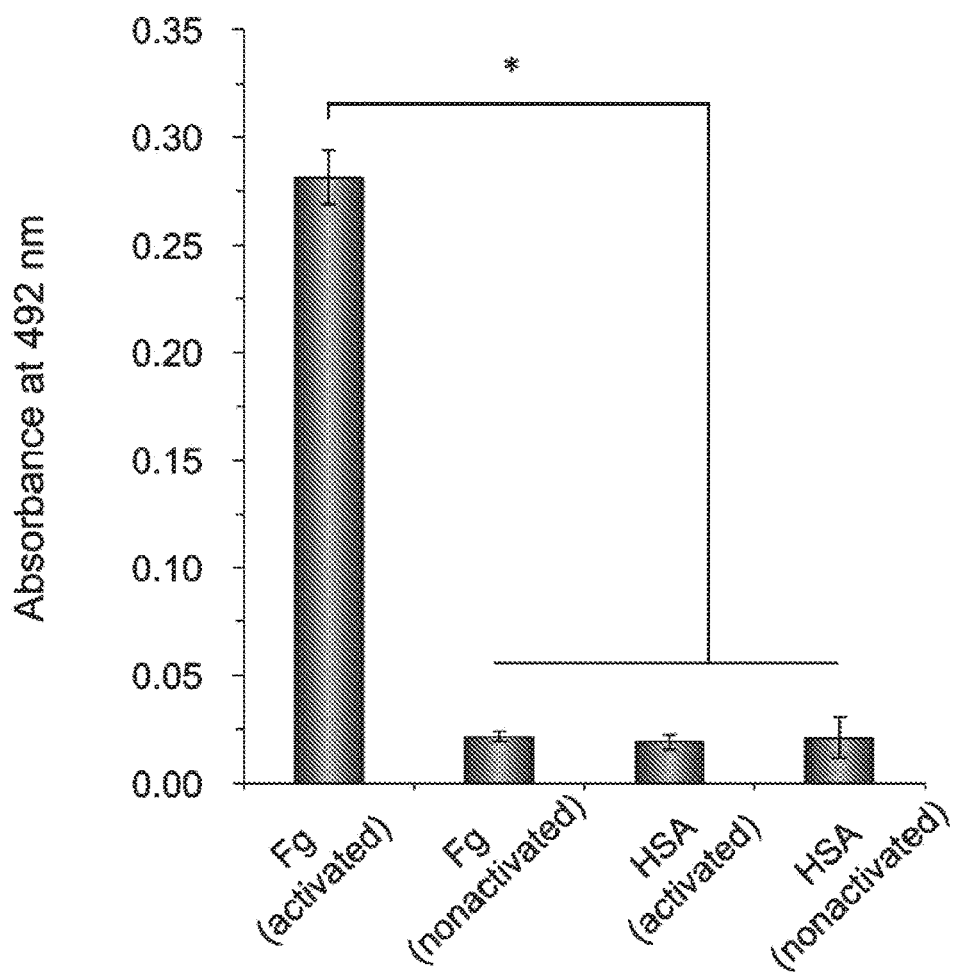
FIG. 9 compares surface functionalization and specific antibody-antigen interaction on the 96-well plate coated with the CB random copolymer, PCB2-37. Both Fg and HSA were conjugated to the CB polymer surface activated by EDC/NHS chemistry, respectively. Anti-Fg conjugated with HRP was utilized to evaluate specific binding, further to verify the feasibility for diagnosis using 96-well plates. Absorbance at 492 nm indirectly represents the amount of conjugated anti-Fg on the surface. The non-activated surface and the surface conjugated with HSA were utilized as controls. Single asterisk (*) indicates statistically significant difference (p<0.001, n=5).

Surface functionalization. To further evaluate the capability and versatility of the CB random copolymer-modified 96-well polystyrene plate for conjugating biomolecules, Fg and HSA were covalently immobilized via EDC/NHS coupling chemistry, respectively. The antibody detection was then conducted via enzyme chromogenic reaction. A typical antibody, anti-Fg conjugated with HRP was added into each well and ensured sufficient contact with surfaces. The degree of color reaction can indirectly show the amount of antibody detection. The non-activated CB surface will maintain non-fouling capability without any adhered biomolecules on the surface, leading to no subsequent antibody detection (FIG. 9, Fg non-activated). For the surface covalently bonded with HSA yet contacted with anti-Fg, there is no specific antibody-antigen induced binding as well (FIG. 9, HSA activated and HSA non-activated). The degree of surface functionalization could be adjusted by changing EDC/NHS concentration and the pH of the antibody conjugation buffer. Previous studies have shown that CB surfaces can still maintain nonfouling capability even being partially conjugated with biomolecules. Thus, this CB polymer modified 96-well plate is promising for the detection of biomolecules in complex media, including serum, plasma, and blood.

Example 1 describes the preparation, characterization, and use of representative zwitterionic/hydrophobic copolymers of the invention.

Zwitterionic/Photoreactive Copolymers

In another embodiment, the invention provides copolymers having zwitterionic groups and photoreactive groups, each pendant from the copolymer's backbone. The pendant zwitterionic groups impart low-fouling and functionalizable properties to surfaces that are treated or coated with the copolymer. The pendant photoreactive groups serve to facilitate binding (i.e., covalent coupling) of the copolymer to the surfaces treated with the copolymer. The relative amounts of zwitterionic groups and photoreactive groups pendant from the copolymer's backbone are adjustable via copolymer synthesis to achieve the desired degree of low-fouling and functionalization and binding of the copolymer to the surface, each of which can be tuned depending on the nature (e.g., composition) of the surface to be treated or coated.

Biofouling on implanted, blood-contacting medical device surfaces remains to be of serious concern for adverse biological reactions. Medical grade polyvinyl chloride (PVC) material has been used in the market for decades, particularly as the blood-contacting tubing. However, they are still facing serious biofouling issue during the clinical applications. Nature shows that low adhesion and high wettable surfaces are the keys to inhibit surface biofouling and non-mild interaction induced variation of blood components.

Medical grade polyvinyl chloride (PVC) tubing is resistant to many chemicals, solvents, corrosion and has a long-life expectancy, and also resistant to most sterilization methods. PVC's extremely smooth surface provides maximum fluid flow characteristics, reducing the fouling build up that could lead to nonspecific blood protein adsorption and bacterial growth. However, it is essential to be aware that most commercial medical grade PVC tubing is blended with plasticizer (up to 40%) to ensure the mechanical flexibility, and their surfaces are quite hydrophobic, which may cause serious adverse reactions when contact with human blood, including blood protein adsorption, platelets activation/aggregation, red blood cells lysis, complement activations and so on. Although medical grade PVC tubing in the current market has been used in the hospital with blood contacting applications for decades, the tubing is not designed originally to avoid the above issues. Notably, medical grade hydrophobic PVC-based materials have already shown serious thrombin generation, complement activation, and others. Thus, compositions and methods to impart the surface of medical grade PVC tubing with biocompatibility are urgently required.

Hydrophilic bioinspired nonfouling materials have been used for surface coating of medical devices for decades. As a unique zwitterionic material, poly(carboxybetaine) (PCB), shows undetectable protein adsorption (<0.3 ng/cm$^2$) against undiluted human serum or plasma and extensively reported in a broad range of biomedical applications without trigger unfavorable biological reactions, which exceeds the performance of conventional hydrophilic or amphiphilic polymers (e.g. PEG). The carboxybetaine (CB) groups, which are super-hydrophilic and charge-neutral with an inner salt structure, can form a layer of strongly bound water molecules that cannot be displaced by bioactive species, thus inhibiting the non-specific interaction between blood components and tubing surface completely. Nonetheless, it is still a challenge to stabilize super-hydrophilic CB polymer directly onto the surface of commercial hydrophobic products aiming for practical clinical applications with a simple and effective method.

In certain embodiments, the zwitterionic/photoreactive copolymer has both superhydrophilic carboxybetaine (CB) units and hydrophobic/photosensitive N-(4-benzoylphenyl) acrylamide (BPAA) units. In certain of these embodiments, the zwitterionic/photoreactive copolymer has formula (III):

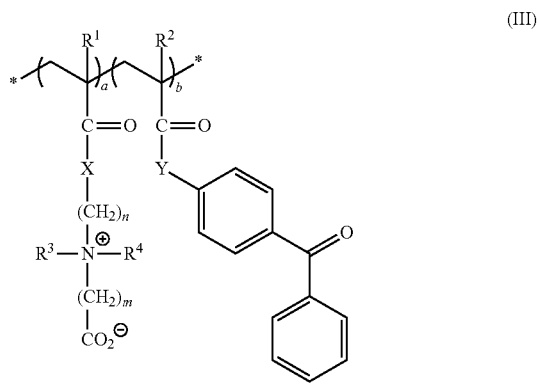

wherein $R_1$ and $R_2$ are independently —$(CH_2)_x$H, where x is an integer from 0 to 20;

$R_3$ and $R_4$ are independently —$(CH_2)_xH$, where x is an integer from 0 to 20;

X is O or NH;

Y is O or NH;

n is an integer from 1 to 20;

m is an integer from 1 to 20;

a is from about 0.10 to about 0.90 mole percent;

b is about 0.10 to about 0.90 mole percent;

a+b is 1.0; and

* represents the copolymer terminal groups.

In certain of these embodiments, $R_1$ and $R_2$ are independently selected from the group consisting of hydrogen and methyl.

In certain embodiments, $R_3$ and $R_4$ are independently selected from the group consisting of hydrogen and C1-C3 alkyl.

In certain embodiments, n is 1, 2, 3, 4, 5, or 6. In some embodiments, n is 2 or 3.

In certain embodiments, m is 1, 2, 3, 4, 5, or 6. In some embodiments, m is 1 or 2.

In certain embodiments, a is from about 0.70 to about 0.90 mole percent. In some embodiments, a is about 0.80 mole percent.

In certain embodiments, b is about 0.10 to about 0.30 mole percent. In some embodiments, b is about 0.20 mole percent.

In certain embodiments, $R_1$ is hydrogen or methyl, $R_2$ is hydrogen or methyl, $R_3$ and $R_4$ are methyl, and X is NH and Y is NH.

In other embodiments, $R_1$ is hydrogen or methyl, $R_2$ is hydrogen or methyl, $R_3$ and $R_4$ are methyl, X is O, and Y is O.

In further embodiments, $R_1$ is hydrogen, $R_2$ is hydrogen, $R_3$ and $R_4$ are methyl, X is NH, Y is NH, n is 3, and m is 1. In certain of these embodiments, a is about 0.80 mole percent and b is about 0.20 mole percent.

The following is a description of the preparation, characterization and use of representative zwitterionic/photoreactive copolymers of the invention and their use in the compositions and methods of the invention.

The present invention provides a surface modification strategy that directly imparts commercial hydrophobic medical grade PVC tubing with superhydrophilicity and nonfouling capability via a simple and effective dip-coating method. The strategy is realized through covalently grafting a zwitterionic carboxybetaine (CB) copolymer to the internal surface of the PVC tubing by photo-induced conjugation and self-crosslinking. The CB copolymer coated commercial medical grade PVC tubing (Streamline Airless System Set, Medisystems Corporation, MA, USA) shows high surface wettability and ultra-low fouling against 100% human serum.

Figures 10A, 10B:
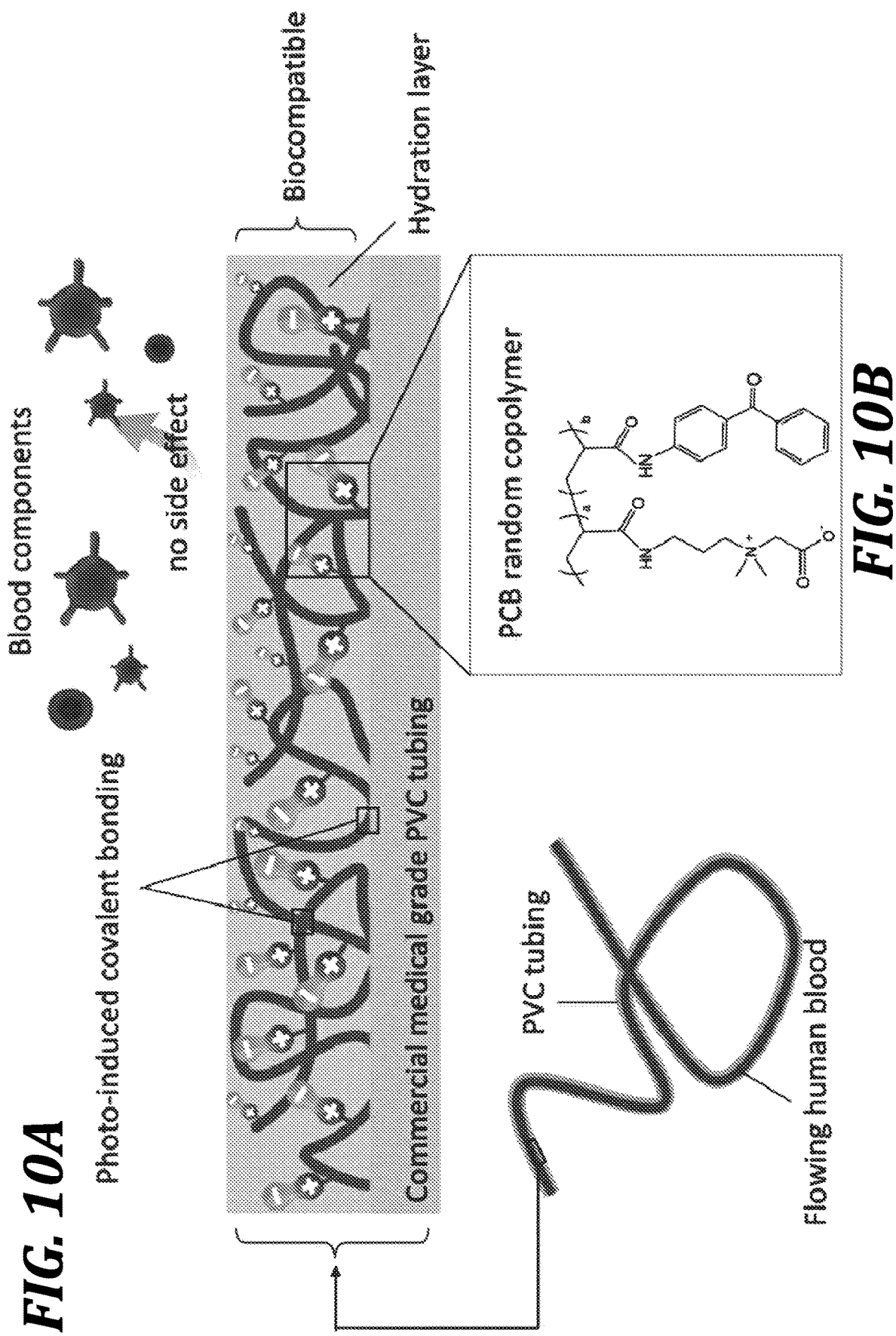
FIG. 10A is a schematic representation of zwitterionic carboxybetaine (CB) copolymer coated commercial medical grade blood contacting PVC tubing.
FIG. 10B illustrates the chemical structure of a representative photoreactive carboxybetaine (CB) polymer useful in the method of the invention.

FIG. 10A is a schematic illustration of the method of the invention: a CB copolymer is covalently grafted to the internal surface of the medical grade PVC tubing by photo-induced conjugation and crosslinking. A representative photoreactive CB copolymer (FIG. 10B) was prepared through conventional radical polymerization, and a medical grade PVC tubing was coated by synthesized polymer and stabilized under UV irradiation. The surfaces grafted with PCB copolymer through dip-coating showed significant better resistance to nonspecific protein adsorption against 100% human serum than uncoated tubing. Therefore, this surface modification strategy is highly promising for improving the biocompatibility of current commercial medical-grade PVC tubing.

The amphiphilic random copolymers were synthesized through a conventional free radical polymerization method using AIBN as a thermal free radical initiator. The viscosity of these reaction solutions gradually increased along with the processing of polymerization at 65° C., indicating the conversion of monomers to copolymers. From the calculation of the integral values of characteristic peaks in $^1H$ NMR spectra, the unit fraction of each monomer was obtained. The existence of all functional units was verified with $^1H$ NMR, where unit fraction of each monomer was obtained from the integral values of characteristic peaks: 3.82 ppm (—$CH_2$—, 2H) for the CB unit and 6.80-7.85 ppm (benzophenone-H, 9H) for the BPAA unit. The chemical structure of this polymer is shown in FIG. 10B. Hydrophilic CB monomer and hydrophobic/photosensitive BPAA in the polymer chain were randomly distributed, with a total composition approximately equal to that of the monomer feed solutions. These results highly match with other random copolymers containing phosphorylcholine group, which has been widely utilized for surface modification of biomedical devices.

Figure 11A:
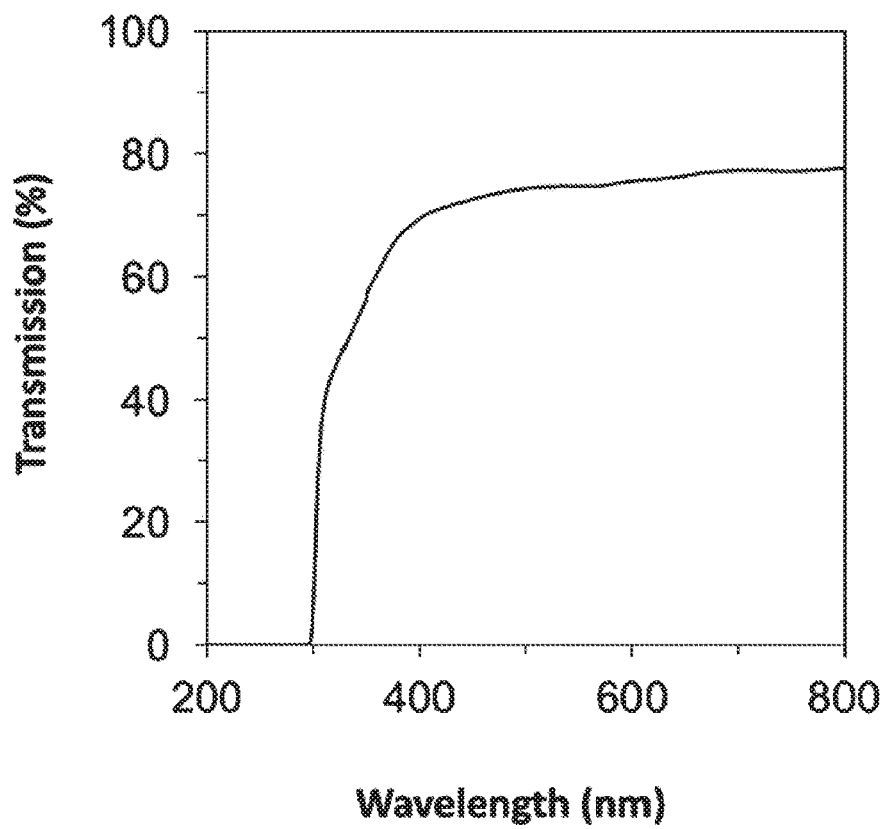
FIG. 11A illustrates UV light permeability through commercial medical grade PVC tubing.
Figure 11B:
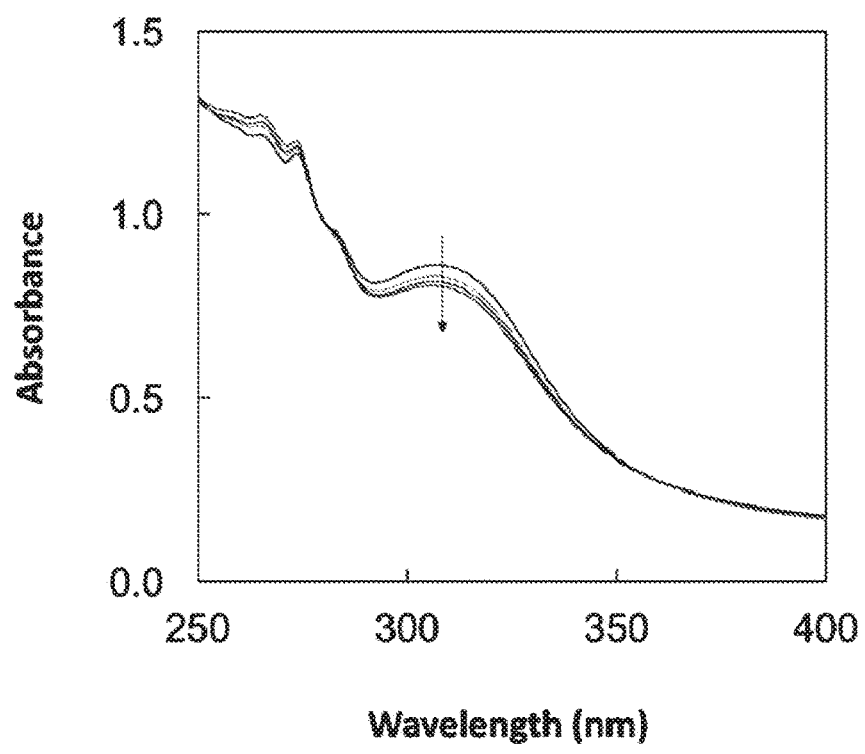
FIG. 11B illustrates permeated light-induced degradation of photosensitive (benzophenone) group on PCB copolymer.

The UV light permeability test shows that this PVC tubing has 50% of light transmission at 312 nm wavelength, which is the best irradiation wavelength for benzophenone group (FIG. 11A). Thus, the physically adhered polymer on the internal surface could be stabilized easily by applying external UV light. Results show that this polymer is very sensitive to UV light (312 nm) with the variation of absorbance spectrum from 300 to 350 nm, indicating the occurrence of photo-induced covalent binding to the PVC tubing surface and self-crosslinking (FIG. 11B).

Figure 12A:
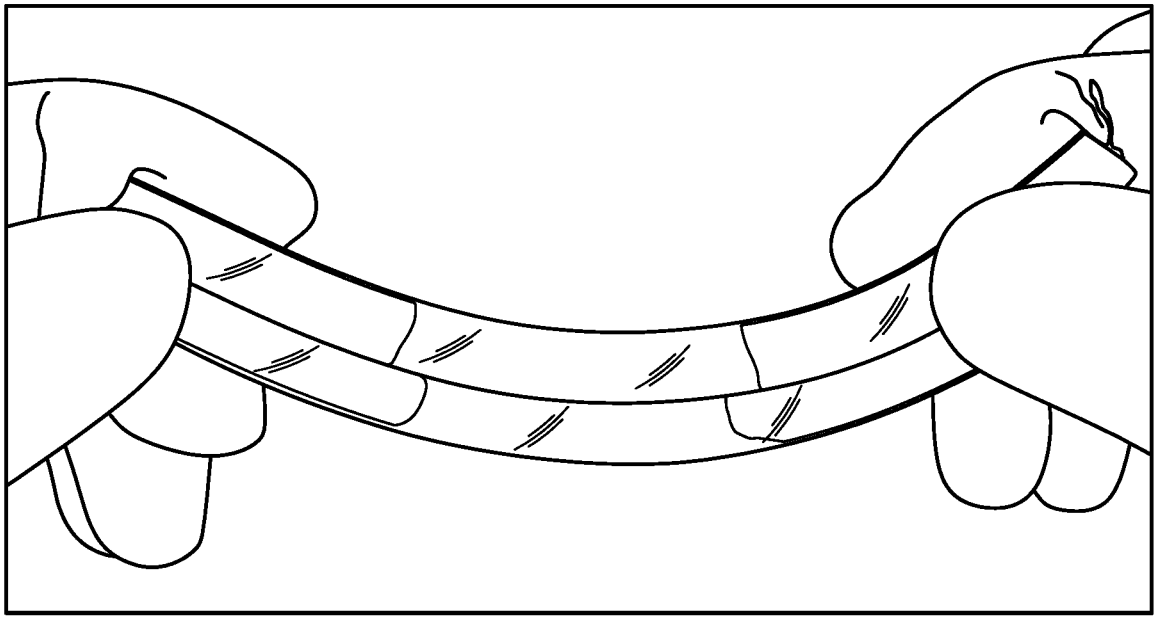
FIG. 12A illustrates commercial flat PVC tubing
Figure 12B:
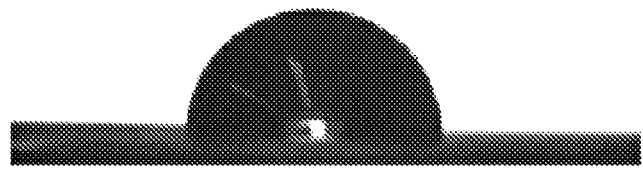
FIG. 12B compares water contact angle on uncoated PVC film and PCB-coated PVC film.
Figure 12B:
Figure 13A:
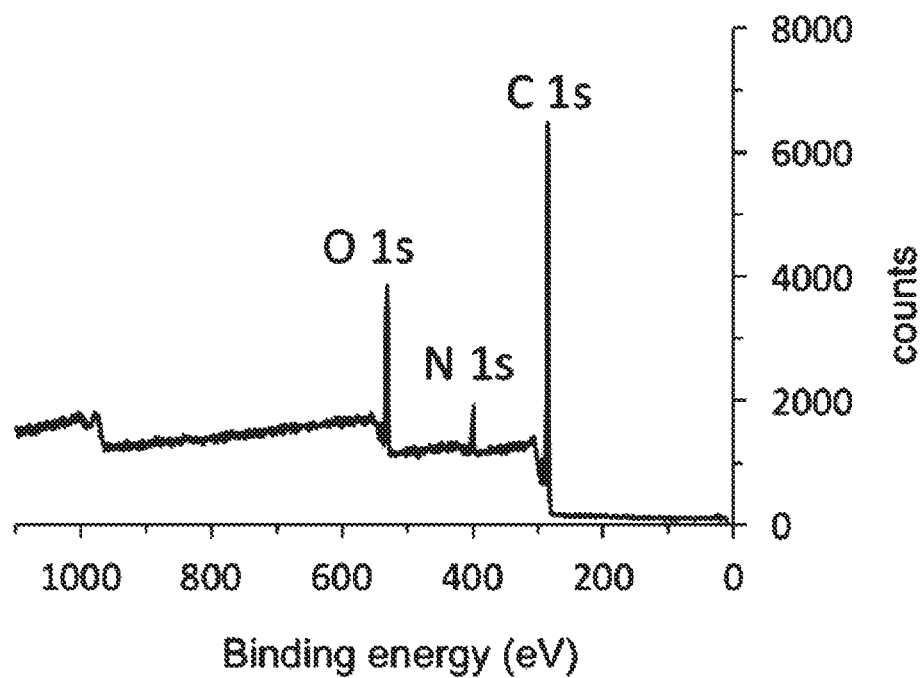
FIGS. 13A-13D compare X-ray photoelectron spectroscopy (XPS) survey spectra of four: representative PCB copolymer (13A), uncoated commercial PVC tubing (13B), PCB-coated commercial PVC tubing storage for 1 week at the dry condition (13C), and PCB-coated commercial PVC tubing storage for 3 weeks at the dry condition (13D).
Figure 13B:
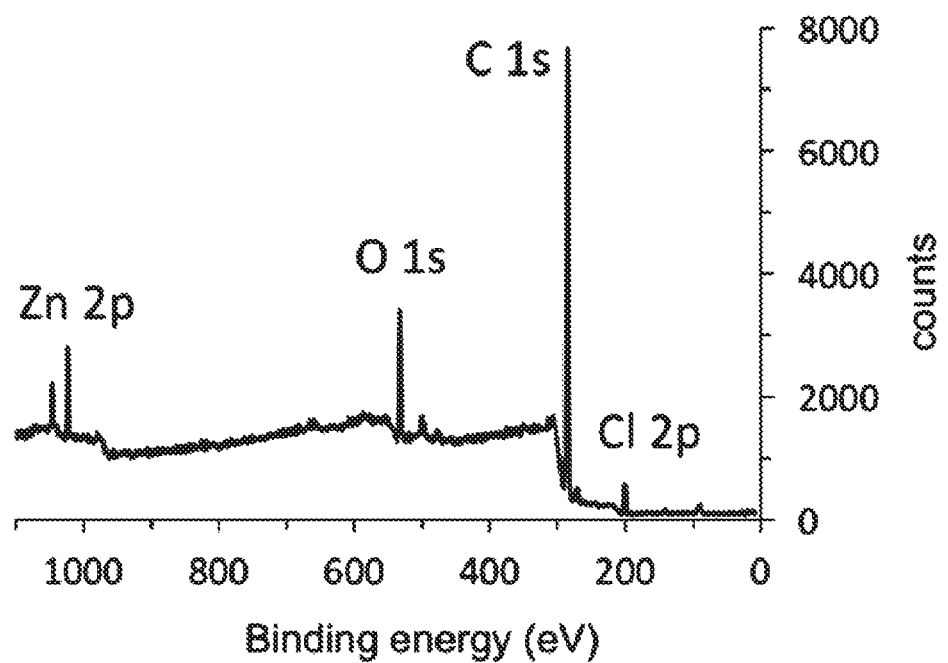
Figure 13C:
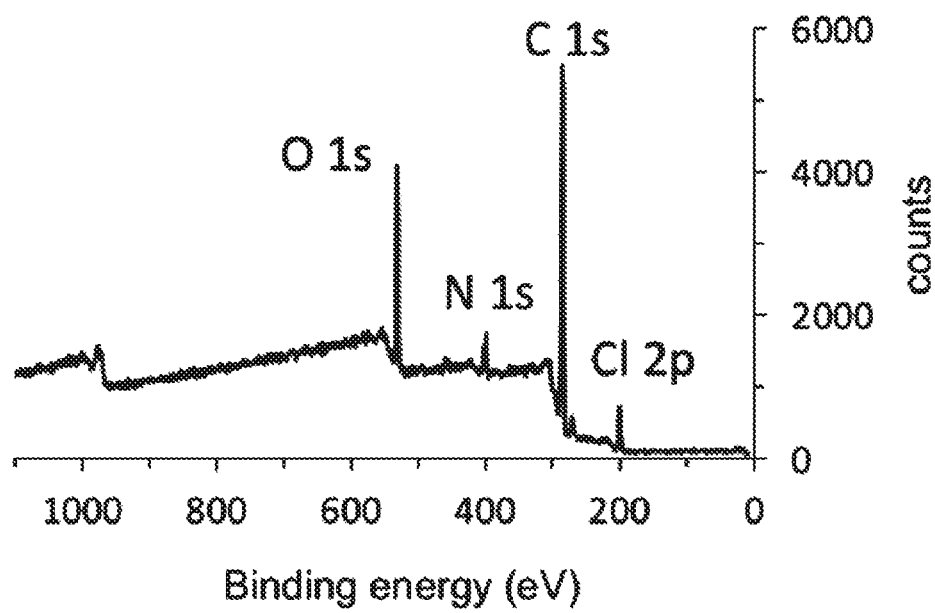
Figure 13D:
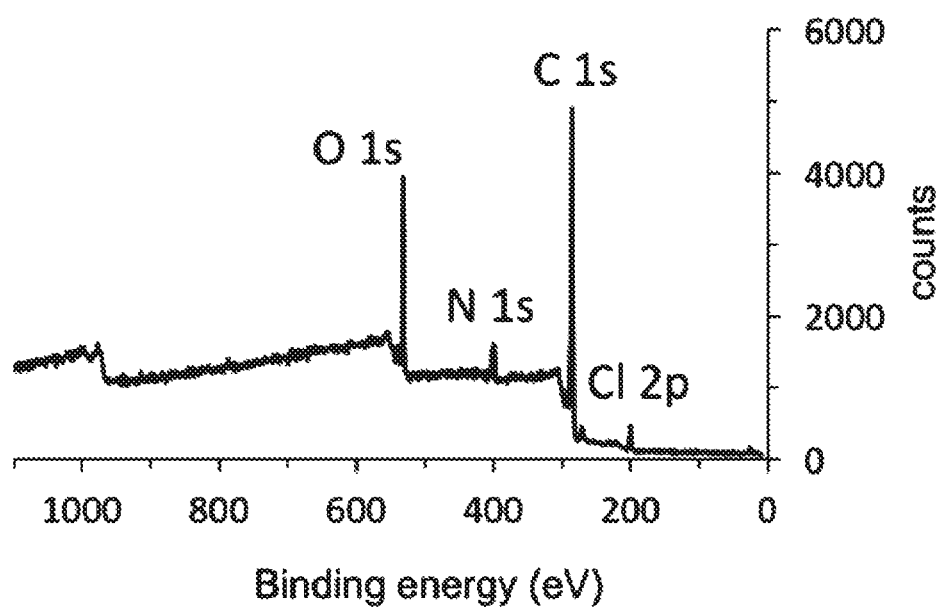

Hydrophilic nature is one of the key characteristics of PCB grafted surface. The water contact angles under dry condition were measured directly on the coated and uncoated medical grade PVC tubing. The results show that on the curved PVC tubing (FIG. 12A), the water contact angle on the PCB coated tubing is much smaller than the uncoated one. In general, the water contact angle of the PCB-coated flat PVC surface is around 10°, while the uncoated PVC flat surface is greater than 85° (FIG. 12B). Thus, grafting of PCB copolymer converted hydrophobic PVC tubing surface to a super-hydrophilic surface.

X-ray photoelectron spectroscopy (XPS) was used to verify the existing and stability of PCB polymer aiming to make our technique more closely to clinical application. The binding energy (BE) was corrected using the C 1s peak at 285 eV as a reference. XPS results show that PCB-coated surface has same N 1s peak as the original PCB polymer (FIGS. 13A-13D) and a steady atom composition (Table 1) was obtained even after preserved at the dry state and room temperature for 3 weeks.

TABLE 1

Surface atom composition of different samples.

| Sample | Atomic Concentration (%) | | | | |
|---|---|---|---|---|---|
|  | C 1s | O 1s | N 1s | Cl 2p | Zn 2p |
| 1) PCB polymer | 79.9 | 14.4 | 5.9 | / | / |
| 2) Uncoated | 86.4 | 8.6 | / | 3.3 | 1.7 |
| 3) Coated (1 week) | 74.0 | 15.3 | 5.7 | 5.0 | / |
| 4) Coated (3 week) | 74.6 | 16.2 | 5.5 | 3.7 | / |

The results show that PCB was successfully grafted on the internal surface of commercial medical grade PVC tubing with excellent stability. Interestingly, the peak of zinc (Zn 2p) was also observed from the survey spectrum, indicating the existing of ZnO which was commonly coated on medical-grade PVC surface to improve the anti-microbial capability.

Figure 14:
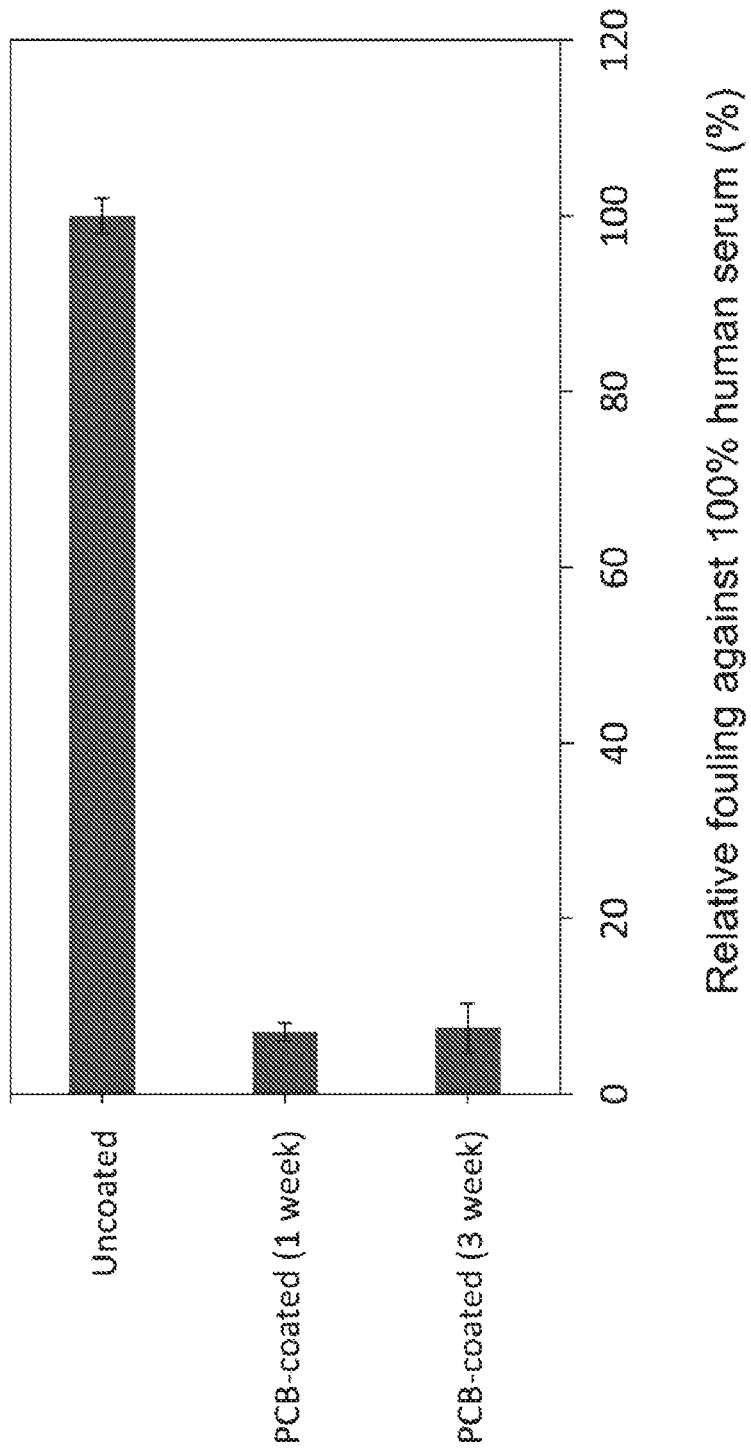
FIG. 14 compares relative fouling against 100% human serum on PCB coated and uncoated medical grade PVC tubing.

Biofouling assessments are essential to evaluate the clinical application potential of current design strategy. Protein adsorption is the primary event that occurs on the surface of biomaterials in contact with a biological environment. In FIG. 14, adsorbed amount of serum proteins on CB polymer-coated tubing were significantly reduced compared to uncoated tubing, indicating that zwitterionic CB polymer coating layer has high anti-fouling capability. Importantly, there is no difference between the fouling level of PCB-coated tubing preserved for one week and three weeks. This further demonstrates the stability of PCB coating layer and consistency with the XPS results. All of the results show that the representative PCB copolymer can impart medical grade PVC tubing with super-hydrophilicity and durable antifouling capability.

In summary, in one aspect, the invention provides a functional random-type amphiphilic zwitterionic copolymer having both superhydrophilic carboxybetaine (CB) units and hydrophobic/photosensitive N-(4-benzoylphenyl) acrylamide (BPAA) units that is useful as a surface coating material. The CB-random-copolymer-modified medical grade PVC tubing has significantly improved non-fouling properties than the commercial uncoated medical grade PVC tubing with ultralow attachment surface. The surface coating is advantageously simple and effective for large-scale applications via a dip-coating method. Its utility is further verified through its ability to achieve a noninvasive coating and a long-term duration. Thus, this technique is promising for a wide range of medical and engineering applications, particularly on medical grade PVC tubing.

Example 2 describes the preparation, characterization, and use of representative zwitterionic/photoreactive copolymers of the invention.

In a related embodiment, the present invention provides a surface modification strategy that directly inhibits or prevents leaching of plasticizers from a surface (e.g., a plastic surface, such as a polyvinyl chloride surface (PVC) or a polyurethane (PU) surface) such as commercial hydrophobic medical grade PVC or PU tubing via a simple and effective method. In one embodiment, the strategy is realized through covalently grafting a zwitterionic carboxybetaine (CB) copolymer to the internal surface of the PVC tubing by photo-induced conjugation and self-crosslinking.

Surface modification of a commercial polyvinyl chloride (PVC) medical devices with zwitterionic copolymers of the invention improves the biocompatibility of PVC and prevents the migration of plasticizer (e.g., phthalate esters, such as di-2-ethylhexyl phthalate (DEHP)) from PVC to patients under various shear stresses.

The following is a description of the preparation, characterization and use of representative zwitterionic/photoreactive copolymers of the invention to impart biocompatibility and inhibit plasticizer leaching on polyvinyl chloride.

Biofouling on implanted, blood-contacting medical device surfaces remains serious concern for adverse biological reactions. Medical-grade polyvinyl chloride (PVC) materials have been used for decades, particularly as blood-contacting tubes and containers. However, these materials face (a) biofouling related issues (e.g., platelet activation, complement activation, and thrombin generation) and (b) leaching issue of toxic plasticizers in clinical applications. The present invention provides a surface modification method that can dramatically prevent blood protein fouling, human platelet activation, and complement activation on commercial medical-grade PVC materials under various dynamic perturbations. The surface coating can be achieved via a simple yet effective dip-coating, followed by light-irradiation using a biocompatible polymer consisting of zwitterionic carboxybetaine (CB) groups and photosensitive crosslinking groups. This biocompatible polymer with tunable functional groups can be routinely fabricated at any scale and impart super-hydrophilicity and non-fouling capability on commercial PVC materials. Furthermore, the polymer effectively prevented leaching of toxic plasticizer out from commercial medical-grade PVC materials. This technique is readily applicable to many other medical devices requiring biocompatible surfaces.

Medical-grade polyvinyl chloride (PVC) has been used in flexible medical products, due to its resistance to most chemicals, solvents, and sterilization methods, and its low cost. Although these products have passed initial critical toxicological, biological, and physiological testing, medical-grade PVC-based materials continue to receive increasing criticism due to emergence of serious blood protein adsorption, platelets activation/aggregation, red blood cells lysis, thrombin generation, complement activation, and others, because unfavorable interactions occur between non-biocompatible PVC and blood components. Blood protein adhesion plays a major role in determining the biocompatibility of materials, which has been considered as the primary event that triggering subsequent adverse reactions. Thus, imparting the medical-grade PVC with biocompatible surfaces will effectively reduce biofouling buildup.

In fact, about 30% of all plastic-based disposable medical devices used in hospitals are usually made from flexible PVC, which is physically blended with up to 40 wt % plasticizers (e.g., phthalates) to ensure their mechanical flexibility as blood-contacting tubes, containers and others. Importantly, the plasticizers can leach from PVC materials into patients to different degrees while in contact with blood, potentially causing serious adverse health effects (e.g., renal toxicity, endocrine toxicity, reproductive system disease, neurotoxicity, hepatotoxicity, and cardiotoxicity) in certain groups of patients. Thus, many studies have been reported about non-toxic plasticizers and non-migrating alternative plasticizers. However, due to lack of the comprehensive evaluation of their long-term health effects, functional effectiveness and cost consideration, currently most of the medical-grade PVC materials on the market are still prepared with conventional methods, facing the leaching issue of toxic plasticizers. Thus, it is desirable to modify the medical-grade PVC products with a biocompatible material that effectively eliminate biofouling-induced adverse reactions and prevent the migration of toxic plasticizer without affecting the prominent properties of the PVC matrix such as inertness, sterilizability, and flexibility.

Current methods for improving the biocompatibility of medical-grade PVC material include importing hydrophobic components (e.g., silicone derivates and polytetrafluoroethylene), grafting hydrophilic antifouling materials (e.g., allylamine, poly(acrylamide), polyethylene glycol), and changing the surface nano/micro-structure. However, none of them clearly demonstrated the capability to solve the issues of non-biocompatibility and plasticizer leaching simultaneously. Notably, hydrophobic materials containing fouling-release moieties (e.g., silicone derivates) could potentially exhibit adverse biological responses such as platelets/complement activation during adhesion-release cycles. Importantly, blood proteins have higher adhesion affinity with a hydrophobic surface, and they show a less organized secondary structure upon adsorption onto a hydrophobic surface than onto a hydrophilic surface.

Hydrophilic nonfouling materials have been used for surface coating of medical devices for decades, including zwitterionic polymers, poly(ethylene glycol), poly(hydroxy-functional acrylates), poly(2-oxazoline)s, poly(vinylpyrrolidone), poly(glycerol), peptides and peptoids. As a unique zwitterionic material, poly(carboxybetaine) (PCB), shows undetectable protein adsorption (<0.3 ng/cm$^2$) against undiluted human serum or plasma and extensively reported in a broad range of biomedical applications without triggering unfavorable biological reactions, which exceeds the performance of conventional hydrophilic or amphiphilic polymers. The carboxybetaine (CB) groups, which are super-hydrophilic and charge-neutral, can form a layer of strongly bound water molecules thus inhibiting the non-specific interaction between blood components and tubing surfaces completely. Nonetheless, it is a great challenge to stabilize super-hydrophilic CB polymer directly onto the surface of commercial hydrophobic tubes aiming for practical clinical applications with a simple and effective method. In addition, to prevent plasticizer leaching, surface modification of plasticized PVC is one of the most frequently investigated strategies, among which surface crosslinking is the most successful technique.

In one embodiment, the invention provides a surface modification method for carboxybetaine copolymer (PCB), aiming to directly impart commercial hydrophobic medical-grade plasticized PVC tubing (Streamline Airless System Set, Medisystems Corporation, MA, USA) with super-hydrophilicity and non-fouling capability and with low plasticizer migration from PVC tubing. The PCB copolymer with tunable functional groups (i.e., zwitterionic carboxybetaine groups, and photosensitive crosslinking groups) was prepared through radical polymerization. The medical-grade plasticized PVC tubing was dip-coated using this polymer, and subsequently, an ultraviolet (UV) light at 312 nm wavelength was applied on the coated surface to stabilize the coated PCB polymer layer and to prevent plasticizer migration via surface crosslinking. The stability and non-cytotoxicity of PCB polymer were confirmed with X-ray photoelectron spectroscopy (XPS) and checked based on ISO 10993-5 guideline, respectively. The wettability and non-fouling capability, platelet activation level, and complement activation level of coated PVC surfaces were directly compared with those on uncoated ones. Notably, the non-fouling capability against 100% human serum under different dynamic perturbations/shear stresses was verified using surface plasmon resonance (SPR), and the plasticizer migration from PVC tubing was effectively prevented. Both the biocompatibility under different dynamic perturbations and the capability of inhibiting plasticizer leaching of PCB copolymers is demonstrated by the method. In addition, these materials and surface modification strategies are applicable to other medical devices.

Figure 15C:
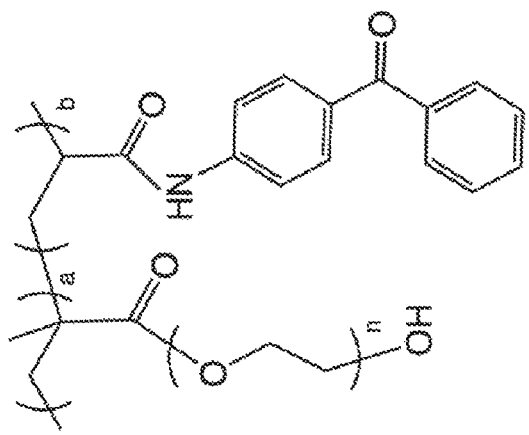
FIGS. 15A-15C illustrates the chemical structures of polymers: poly(CBAA-co-BPAA) (PCB) (15A); poly (CBAA-co-BPAA-co-NB acrylamide) (PCB-NB) (15B); and poly(PEGMA-co-BPAA) (PPB) (15C). CBAA: carboxybetaine acrylamide. BPAA: N-(4-benzoylphenyl) acrylamide. NB acrylamide: nile blue acrylamide. PEGMA: poly(ethylene glycol) methacrylate with an average Mn 360.
Figure 15B:
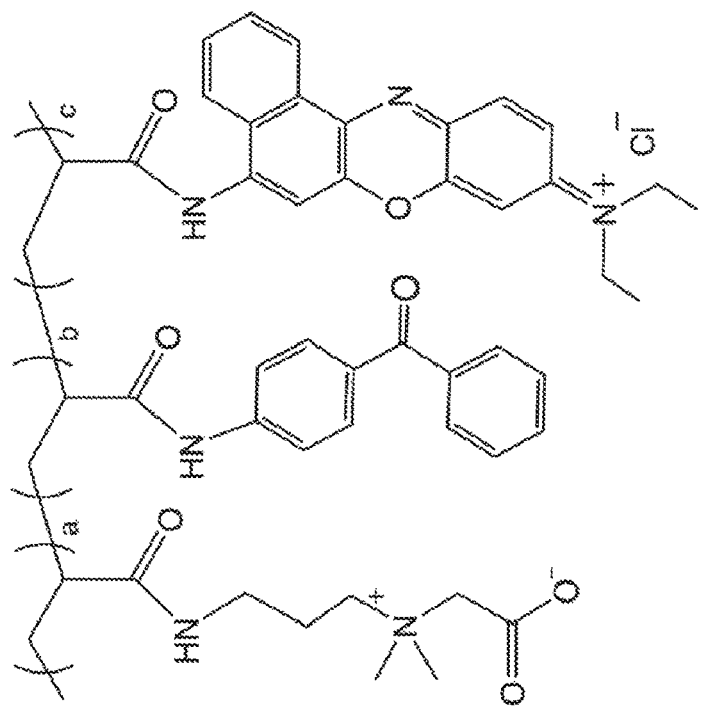
Figure 15A:
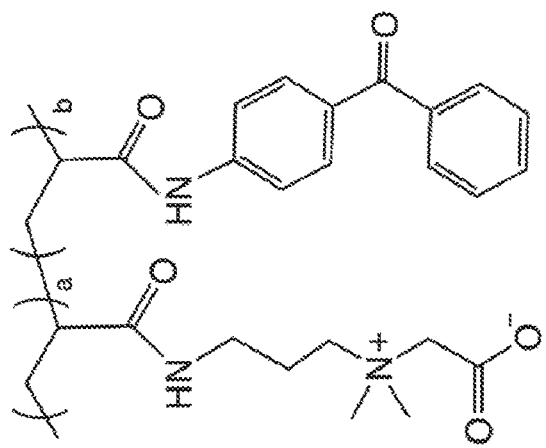

Synthesis of Copolymers. The photo-reactive amphiphilic random copolymers were synthesized through a conventional free radical polymerization method using AIBN as a thermal free radical initiator. This method can ensure the polymers with tunable functional groups can be routinely fabricated at any scale, particularly for industrial scale-up. The viscosity of these reaction solutions gradually increased along with the processing of polymerization at 65° C., indicating the conversion of monomers to copolymers. The chemical structure of poly(CBAA-co-BPAA) (PCB) polymers is shown in FIG. 15A. The CBAA groups are super-hydrophilic and totally charge-neutral that can effectively inhibit the adhesion of blood proteins, cells, and bacteria. The photosensitive groups (BPAA) can stabilize the polymer on the PVC surface through photo-induced crosslinking further preventing the migration of plasticizer. The existing of all functional units was verified with $^1$H NMR, where the unit fraction of each monomer was obtained from the integral values of characteristic peaks: 3.82 ppm (—CH$_2$—, 2H) for the CB unit and 6.80-7.85 ppm (benzophenone-H, 9H) for the BPAA unit. Hydrophilic CB monomer and hydrophobic/photosensitive BPAA in the polymer chain were randomly distributed, with a total composition approximately equal to that of the monomer feed solutions (Table 2). The chemical structures of poly(CBAA-co-BPAA-co-NB acrylamide) (PCB-NB) and poly(PEGMA-co-BPAA) (PPB) are shown in FIGS. 15B and 15C, respectively.

TABLE 2

Characteristics of Representative Synthesized Copolymers$^a$

| | monomer unit composition (mol %) | | | | | molecular weight $^c$ | | solubility $^d$ | |
|---|---|---|---|---|---|---|---|---|---|
| | in feed | in copolymer $^b$ | initiator | polymerization | yield | | | | |
| | CBAA/BPAA | CBAA/BPAA | (mmol/L) | time (h) | (%) | $M_w \times 10^4$ | $M_w/M_n$ | ethanol | water |
| PCB | 80/20 | 81/19 | 5 | 16 | 88 | 4.6 | 2.1 | ++ | ++ |
| PCB-NB | 80/20 | 78/22 | 5 | 16 | 82 | 3.3 | 2.6 | ++ | ++ |
| PPB $^a$ | 80/20 | 79/21 | 5 | 16 | 81 | 4.2 | 2.2 | ++ | ++ |

Figure 16A:
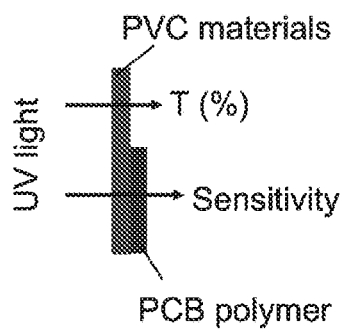
FIGS. 16A-16H relate to light-induced crosslinking of PCB polymer on the internal tubing surface: the transmission light-induced crosslinking of PCB polymer on the internal tubing surface (16A); UV light permeability through commercial medical-grade PVC tubing (16B); photosensitivity of PCB copolymer on the internal tubing surface to transmission light (16C); the water contact angle of pure DI water on uncoated and PCB-coated PVC surfaces (16D); the X-ray photoelectron spectroscopy (XPS) survey spectrum of PCB copolymers (16E), uncoated commercial PVC tubing (16F), PCB-coated commercial PVC tubing storage for 1 week at the dry condition (16G), and PCB-coated commercial PVC tubing storage for 3 weeks at the dry condition (16H). The binding energy (BE) was corrected using the C1s peak at 285 eV as a reference.
Figure 16B:
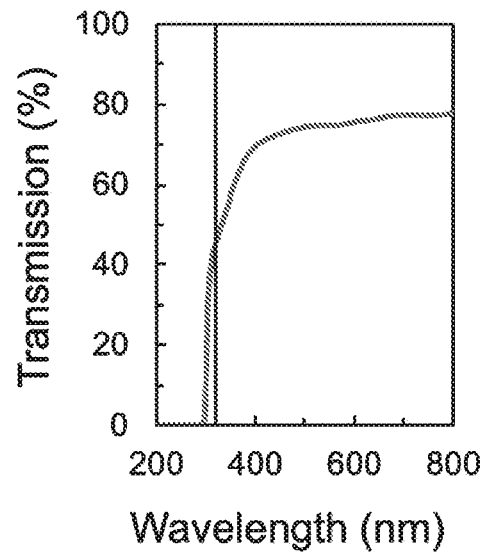
Figure 16C:
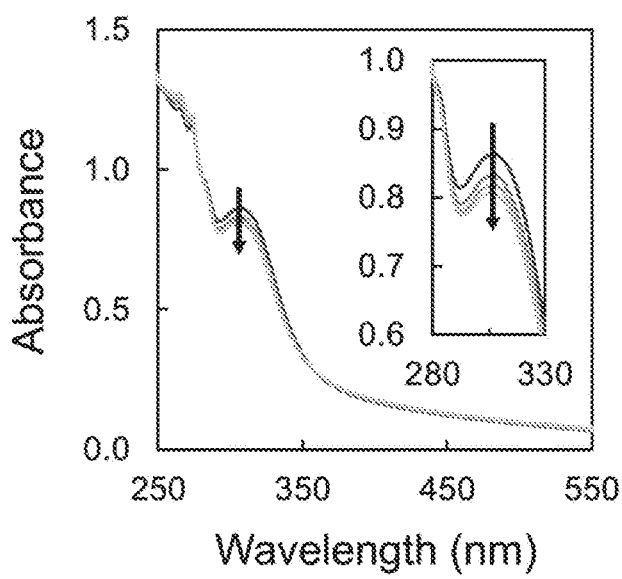
Figure 16D:
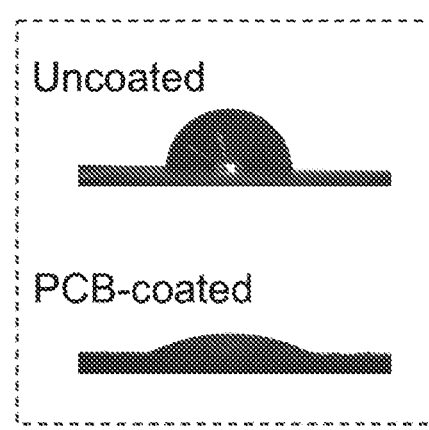
Figure 16E:
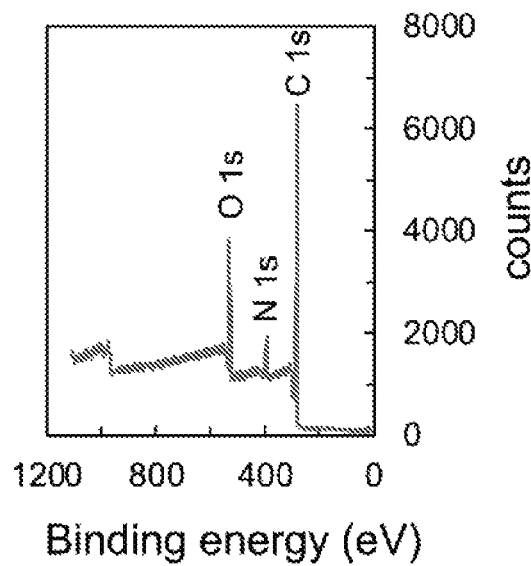
Figure 16F:
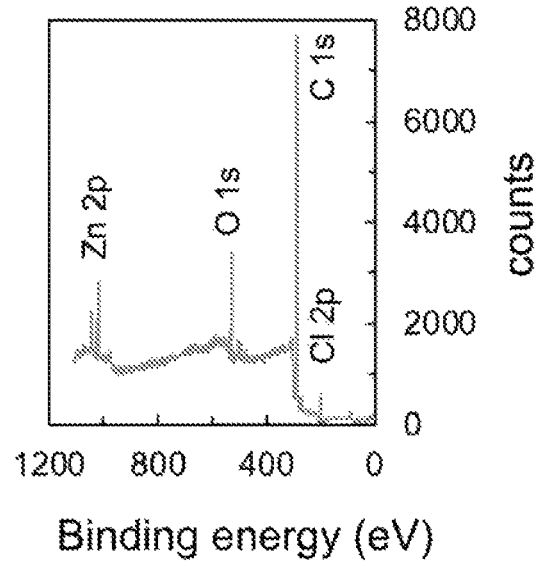
Figure 16G:
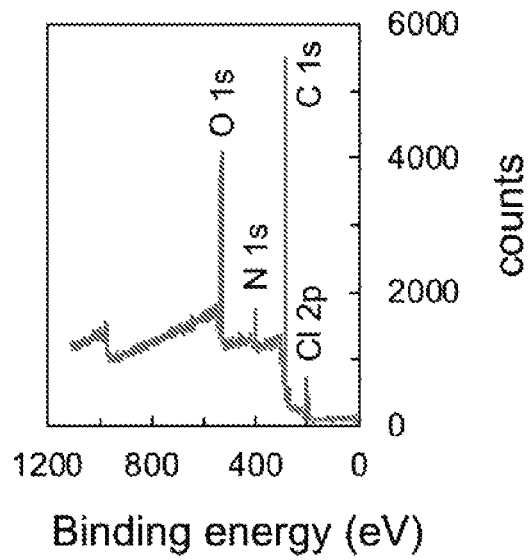
Figure 16H:
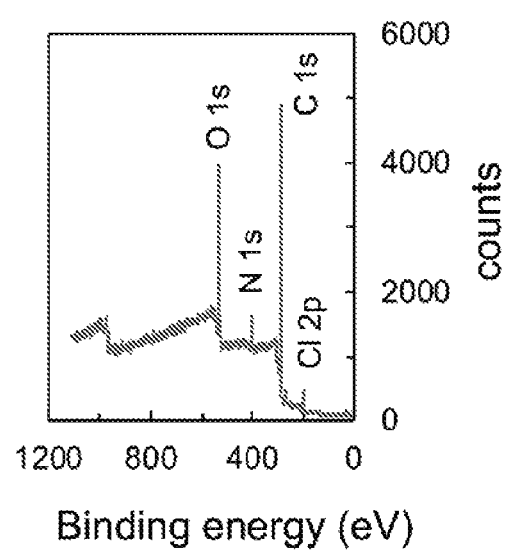

Surface characterization. The UV light permeability test shows that the commercial PVC tubing has 50% of light transmission at 312 nm wavelength (FIGS. 16A and 16B), which is the best irradiation wavelength for benzophenone group in PCB copolymers. Thus, applying external UV light will stabilize the PCB polymers on the internal surface of the tubing. Results in (FIG. 16C) show that this polymer is very sensitive to UV light (312 nm) with the variation of absorbance spectrum from 300 to 350 nm, indicating the occurrence of photo-induced covalent binding to the PVC tubing surface and self-crosslinking. Hydrophilic nature is one of the key characteristics of the PCB grafted surface. The water contact angles under dry conditions were measured directly on the coated and uncoated medical-grade PVC tubing. The water contact angle on the PCB coated tubing is much smaller than that on the uncoated one (FIG. 16D). In general, the water contact angle of the PCB-coated flat PVC surface is around 10°, while the uncoated PVC flat surface is more than 85°. Thus, grafting of PCB copolymer converted hydrophobic PVC tubing surface to super-hydrophilic.

Coating stability. The US FDA requires containers that will come in contact with blood and blood components to not have coating leaching issues. X-ray photoelectron spectroscopy (XPS) was used to verify the existing and stability of PCB polymer aiming to make the technique more closely to practical application. The binding energy (BE) was corrected using the C is peak at 285 eV as a reference. XPS results show that the PCB-coated surface has the same N is peak as the original PCB polymer (FIGS. 16E-16H) and a steady atom composition was obtained even after preserved at the dry state and room temperature for 3 weeks. Thus, PCB was successfully grafted on the internal surface of commercial medical-grade PVC tubing with excellent stability. The peak of zinc (Zn 2p) was also observed from the survey spectrum, indicating the existing of zinc compound (e.g., ZnO) which is commonly coated on medical-grade PVC surface to improve the anti-microbial capability. In addition, the stability of PCB under wet conditions was evaluated. The commercial tubing was coated with a fluorescent-tagged PCB polymer (PCB-NB) and soaked at PBS/ 100% human plasma at 37° C. The amount of leached PCB-NB in the solution was evaluated through the analysis of the UV/Vis spectrum at 590 nm wavelength. The result showed that the PCB polymer absorption peak could not be observed after soaking at either PBS or 100% human plasma at 37° C. for 24 h indicating the stability of PCB polymer under wet conditions.

Biofouling assessments. Protein adsorption plays a major role in biocompatibility evaluation and it is the primary event that occurs on the surface of biomaterials in biological environments. Importantly, protein adsorption behaviors are dependent on both the surface characteristics of the biomaterials and various shear stresses. Both albumin and fibrinogen showed a stronger binding affinity and less organized secondary structure toward hydrophobic alkyl surfaces compared to hydroxyl group terminated hydrophilic surface, with the effect observed greater for albumin. Less plasma proteins adsorption on polyurethane surfaces was observed with increasing shear rate. The adsorption behaviors of plasma proteins on zwitterionic carboxybetaine polymer surfaces under both dynamic and static conditions using a surface plasmon resonance (SPR) biosensor with tunable flow rates and a Micro BCA protein assay kit, respectively, is described herein.

Figure 17A:
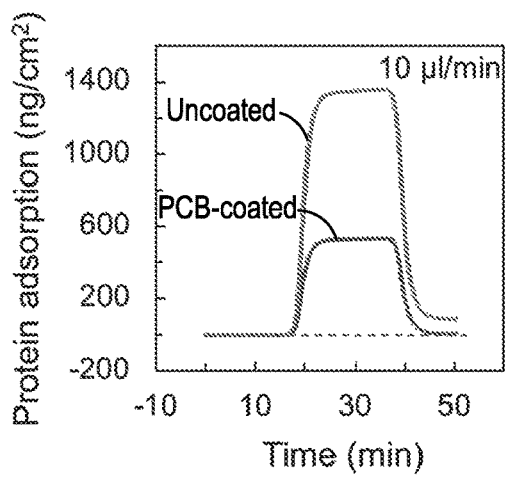
FIGS. 17A-17F show the non-fouling capability assessment: adsorption behavior of 100% human serum on PVC surface and PCB polymer-coated PVC surfaces at dynamic conditions with four different flow rates (10, 40, 100, and 200 μL/min) tested by a surface plasmon resonance (SPR) biosensor (17A-17D). The different flow rates cause different shear forces on the interface between the serum and tubing. Uncoated: SPR chips coated with PVC. PCB-coated: SPR chips coated with PVC first layer and PCB polymer second layer. The thicknesses of PVC and PCB were measured under dry conditions with a value of 18±0.8 nm and 21±1.2 nm, respectively.
Figure 17B:
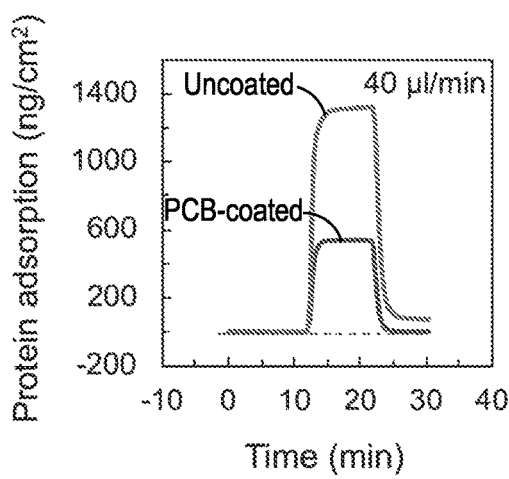
Figure 17C:
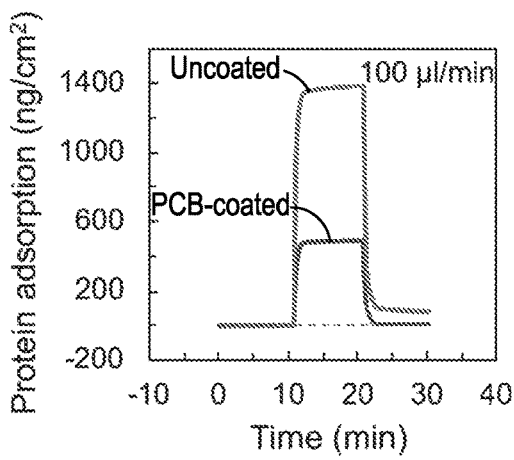
Figure 17D:
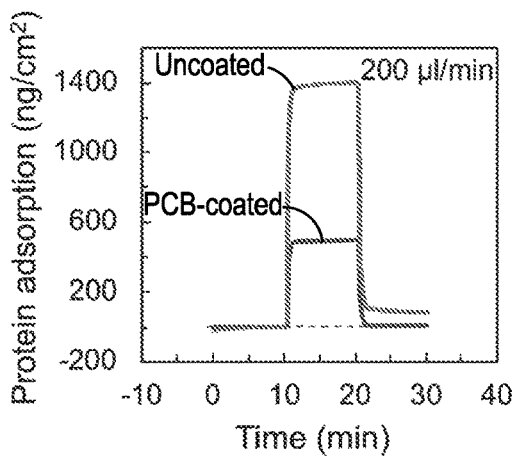
Figure 17E:
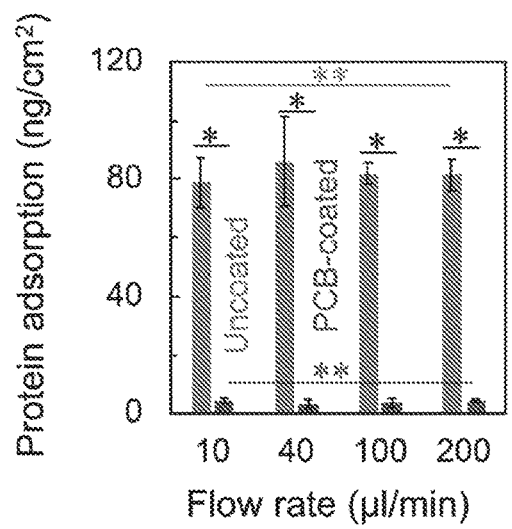
Figure 17F:
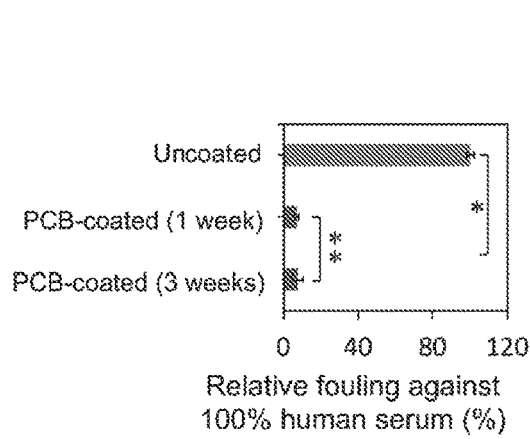

The quantity of nonspecific adsorbed proteins was evaluated using SPR before serum injection and after buffer washing on both uncoated (SPR chips coated with PVC) and PCB-coated (SPR chips coated with PVC first layer and PCB polymer second layer) surfaces (FIGS. 17A-17D). The sharp increase after serum injection was attributed to the change in the bulk refractive index. To compensate for the loss of SPR surface sensitivity due to the coated polymer layer, the sensor response to protein adsorption was calibrated at different polymer thicknesses. The adsorbed amounts of proteins under four different flow rates 10, 40, 100, and 200 μL/min on PCB-coated surfaces are 4.3, 3.3, 3.6 and 4.4 ng/cm$^2$, while on uncoated surfaces are 78.7, 85.9, 81.9, and 81.4 ng/cm$^2$ (FIG. 17E). This result shows that PCB-coated surface has ultra-low fouling (<5.0 ng/cm$^2$) capability and <10% of fouling compared to uncoated surfaces under dynamic conditions regardless of shear stress, and this result is consistent with the result from Micro BCA protein assay kit under static conditions (FIG. 17F). Besides, there is no difference between the fouling level of PCB-coated tubing preserved in PBS for one week and three weeks. This further demonstrates the stability of the PCB coating layer and consistency with the XPS results under dry conditions. Thus, the zwitterionic PCB copolymer can impart medical-grade PVC tubing with super-hydrophilicity and durable antifouling capability.

Figure 18A:
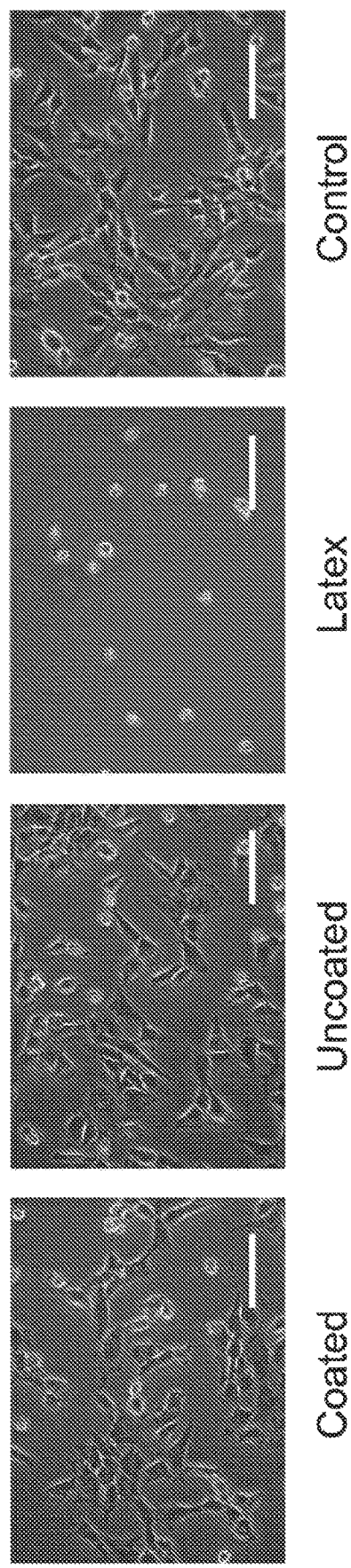
FIGS. 18A-18C illustrates the cytotoxicity evaluation of PCB polymers. Phase-contrast microscopic images of NIH3T3 mouse embryonic fibroblast cells after 48 hours' incubation with elution from PCB-coated tubing, uncoated tubing, latex, and normal cell culture medium (18A) and cell culture medium containing different concentrations of PCB polymers (18B). Scale bar: 50 μm. The cytotoxicity of the PCB polymer was checked based on ISO 10993-5 guideline. The release of the cytosolic enzyme lactate dehydrogenase (LDH) was determined by incubating the cells with different concentrations of PCB polymers at 37° C. in 5% $CO_2$ for 1.0 h (18C). Negative control (NC): cells were cultured with normal serum-free cell culture medium. Positive control (PC): cells were cultured with 0.2 vol % Tween 20 in the serum-free cell culture medium. All the medium was supplemented with phenol red and 1× penicillin/streptomycin. Results are expressed as mean±SD (n=5; *p<0.001, and **p>0.05).
Figure 18B:
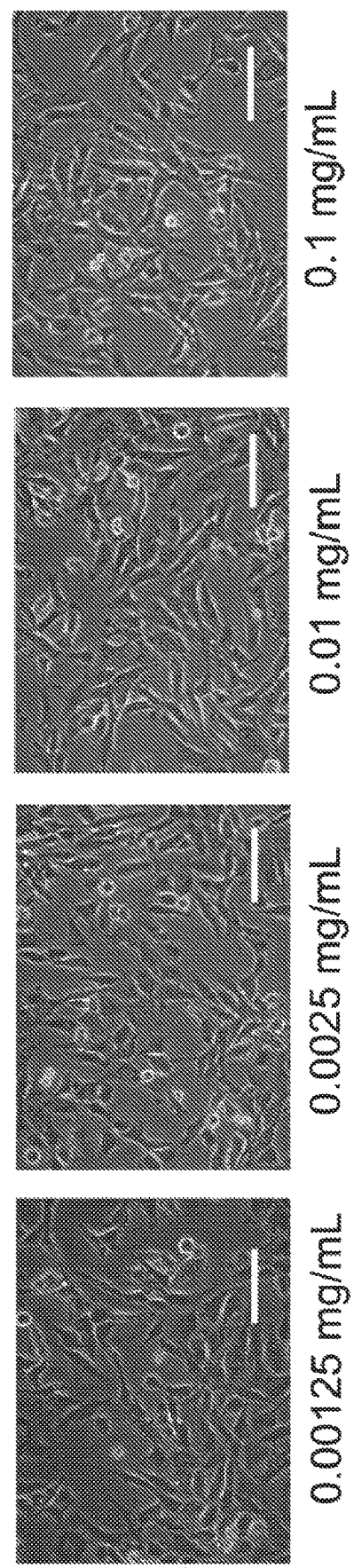
Figure 18C:
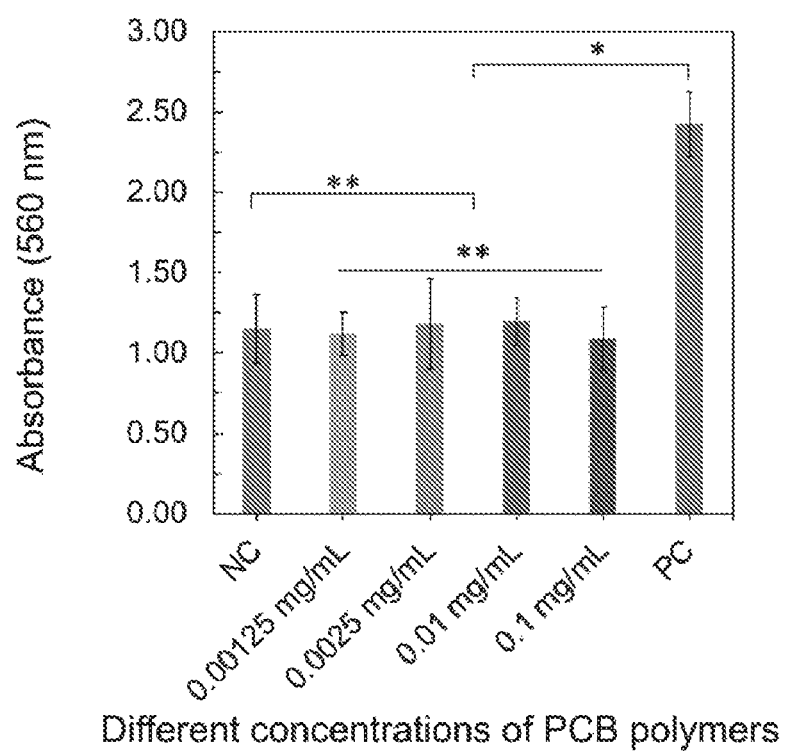

PCB polymer toxicity. The cytotoxicity of the PCB polymer was checked based on ISO 10993-5 guideline. The morphology of NIH3T3 cultured in elution of PCB-coated tubing or medium containing dissolved PCB polymers was observed and compared with controls. As shown in FIG. 18A, the morphology of NIH3T3 cultured in the elution from PCB-coated tubing has no difference from that on uncoated tubing and control samples in the normal cell culture medium. In contrast, cells lost their original spindle shape after being cultured in elution of latex, which is a toxic material used as positive control. Notably, the morphology of cells cultured in the medium containing dissolved PCB polymers did not change compared with the controls as well (FIG. 18B). Thus, PCB polymers are not toxic based on ISO 10993-5 guidelines. Also, cytotoxicity induced by different concentrations (0.00125, 0.0025, 0.01, and 0.1 mg/mL) of PCB polymers was assessed by LDH leakage into the culture medium. A positive correlation between absorbance value at 560 nm and relative LDH levels was used to evaluate cell membrane damage caused by the polymers. The released amount of LDH from cells being cultured with PCB-containing medium has no significant difference from those cultures under normal conditions. In contrast, the released LDH level from cells cultured with 0.20 vol. % Tween 20 medium solution was much higher than the others (FIG. 18C). These results indicated that PCB polymers did not exert cytotoxic effects on the membranes of living cells.

Figure 19A:
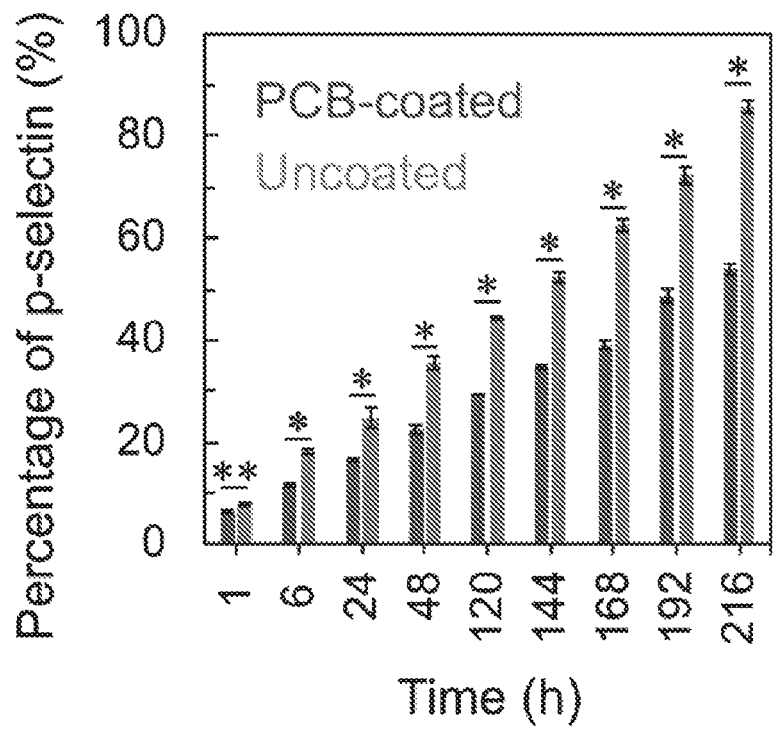
FIGS. 19A-19D illustrate the effect of PCB polymers on platelet quality. The activation levels were assessed by flow cytometry via p-selectin % (19A). The functionality was assessed via von Willebrand Factor (VWF) binding affinity (19B). The viability was assessed by flow cytometry via annexin V % (19C). The morphology score (MS) is used as a simple indicator of platelet health and is defined as 4×(disc %)+2×(spheres %)+(dendrite %) (19D). PCB-coated: PCB-coated PVC surfaces. Uncoated: uncoated PVC surfaces. Results are expressed as mean±SD (n=5; *p<0.001, and **p>0.05).
Figure 19B:
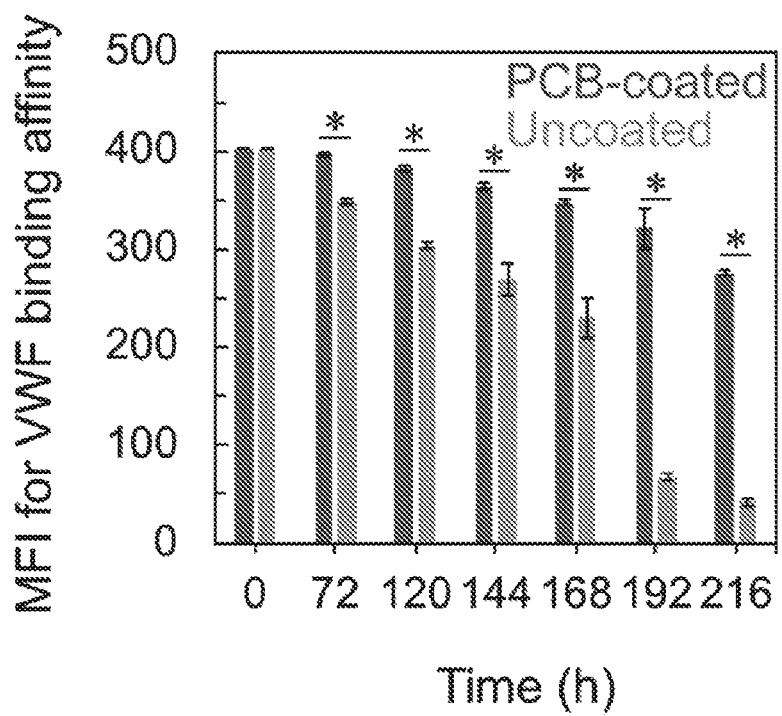
Figure 19C:
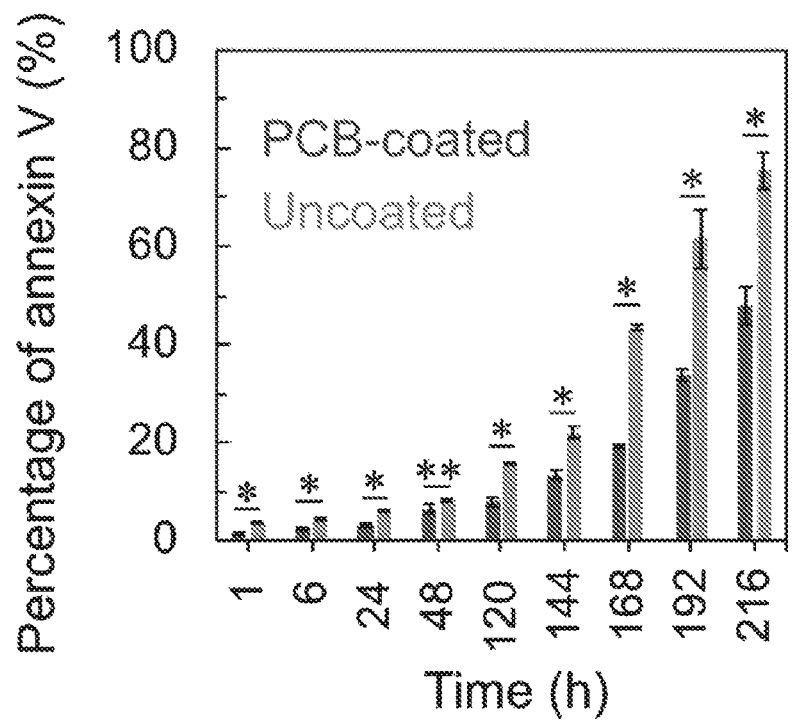
Figure 19D:
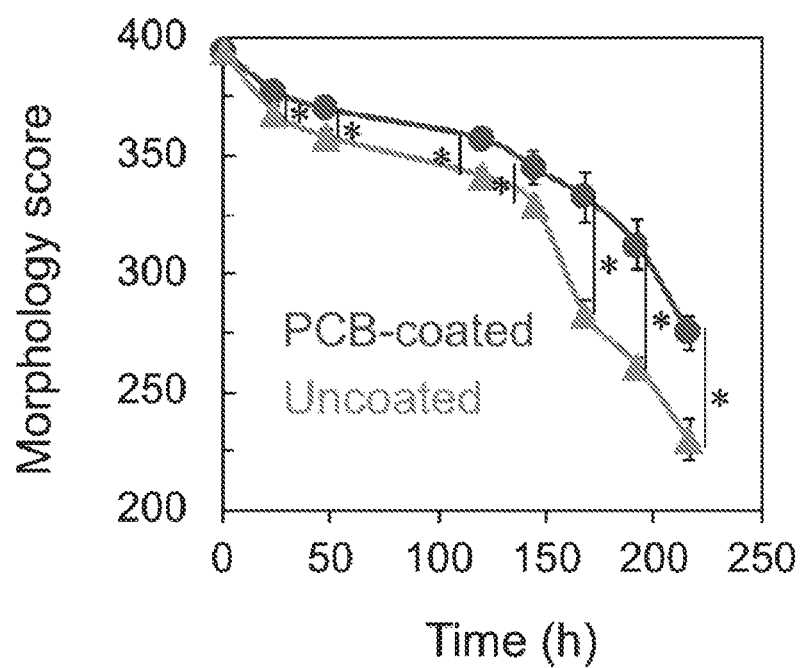

Effect of PCB polymer on platelet quality. The quality of platelets in PCB-coated PVC surfaces and uncoated PVC surfaces are compared to verify the potential of PCB polymers for blood-contacting medical devices. The platelet activation level and binding affinity with von Willebrand factor (VWF) are the most critical parameters to assess the ability of platelets to clot, which directly reflects the quality of platelets. p-Selectin (CD62) is a glycoprotein and a well-described marker of platelet activation. During platelet activation, p-selectin translocates from intracellular granules to the external membrane. The activation level of platelets in the PCB-coated surfaces is much lower than that in uncoated PVC surfaces, indicating the effective inhibition of platelet activation through the use of PCB polymers (FIG. 19A). The functionality test of platelets is the most critical parameter to assess the ability of platelets to clot. As an adhesive plasma glycoprotein, VWF plays a fundamental role in platelet plug formation under physiologic conditions, allowing circulating platelets to adhere and plug sites of vascular injury. The higher mean fluorescence intensity (MFI) (FIG. 19B) correlated with a higher binding affinity with VWF. The platelets on PCB-coated surfaces have a higher binding affinity with VWF than that on uncoated ones from 0 to 168 h, which becomes more obvious after 168 h. Annexin V is commonly used to detect apoptotic cells by its capability to bind phosphatidylserine, which is a platelet apoptosis marker when occurring on the outer leaflet of the plasma membrane. Thus, higher binding of annexin V indicates increased cell apoptosis with decreased viability. As shown in FIG. 19C, platelets on the PCB-coated hydrophilic surfaces have a lower binding level of annexin V than those in uncoated ones, indicating that the PCB-modified surface can effectively maintain platelet viability. Healthy inactivated platelets exhibit biconvex discoid structures with a 2-3 μm in the greatest diameter. Shape changes from discoid to spheroid (disk-to-sphere transformation) occur with the deterioration of platelet health. The morphology score (MS) is used as a simple indicator of platelet health and is defined as 4×(disc %)+2×(spheres %)+(dendrite %). The MS value of the platelets on PCB-coated surfaces is much higher than that in uncoated PVC surfaces (FIG. 19D). Thus, PCB polymer on hydrophobic PVC surfaces can effectively prevent platelet quality deterioration, which makes PCB polymer promising for fabricating blood-contacting devices.

Figure 20:
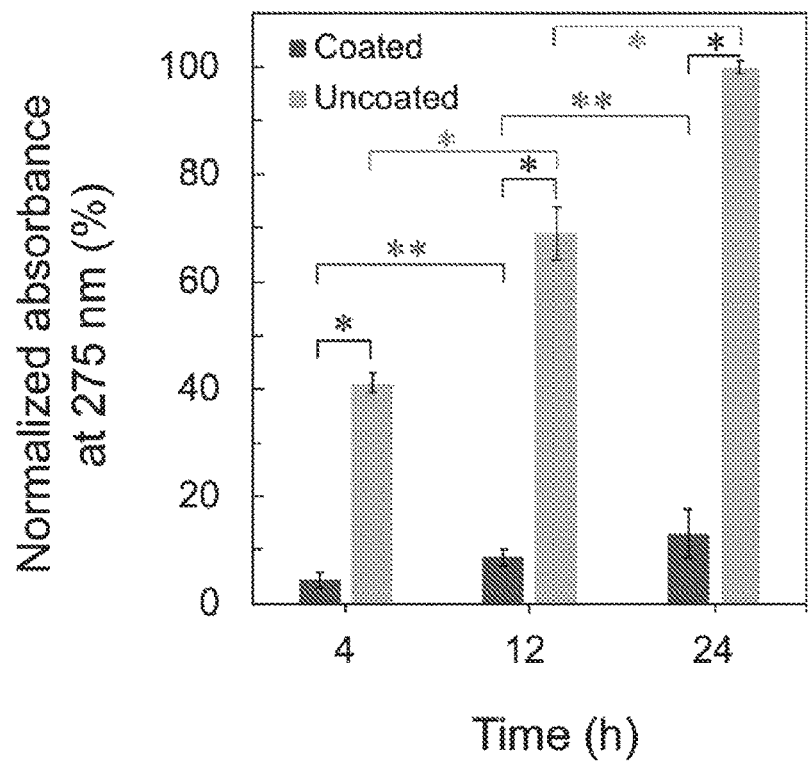
FIG. 20 compares migration of the plasticizer from photoreactive PCB polymer-coated plasticized-PVC and uncoated plasticized-PVC tubing. The absorbance at 275 nm wavelength has a direct proportion with the concentration of leached plasticizers. Results are expressed as mean±SD (n=3; *p<0.001, and **p<0.05).

Plasticizer leaching. Phthalate esters, particularly di-2-ethylhexyl phthalate (DEHP), are the most frequently used plasticizer for commercial PVC due to easy plasticization and processing along with competitive costs. However, DEHP-contained PVC materials are still controversial and not forbidden for biomedical applications although many studies have shown the toxicity of DEHP. Current methods for eliminating the toxicity of plasticized-materials include (a) inhibiting the leaching of DEHP plasticizers through chemical or physical surface modification, (b) developing alternatives to DEHP (e.g., adipates, azelates, citrates, and trimellitates), and (c) creating plasticizer-free alternative polymers to PVC (e.g., silicones, polyurethanes, and polyolefins). Inhibiting the leaching of DEHP could be the most well-evaluated method which require long-term and comprehensive assessments. Notably, surface crosslinking of PVC materials is the most successful technique to effectively prevent DEHP leaching in the current stage. DEHP has three spectral bands around 210 nm, 225 nm and 275 nm. As described herein, the absorption values at 275 nm wavelengths were compared between coated and uncoated PVC tubing. Results in FIG. 20 show that the leached DEHP level from PCB-coated PVC tubing is significantly lower than that from uncoated ones, and it is about 12% of that from uncoated tubing at 24 h. This demonstrates that surface grafted photo-reactive PCB-polymers effectively prevent the migration of DEHP, leading promising applications on eliminating the toxicity of plasticized-PVC materials. The photo-induced surface crosslinking of PCB polymers could be the key to stabilize PCB polymer on the PVC surface and prevent the migration of plasticizers.

Figure 21:
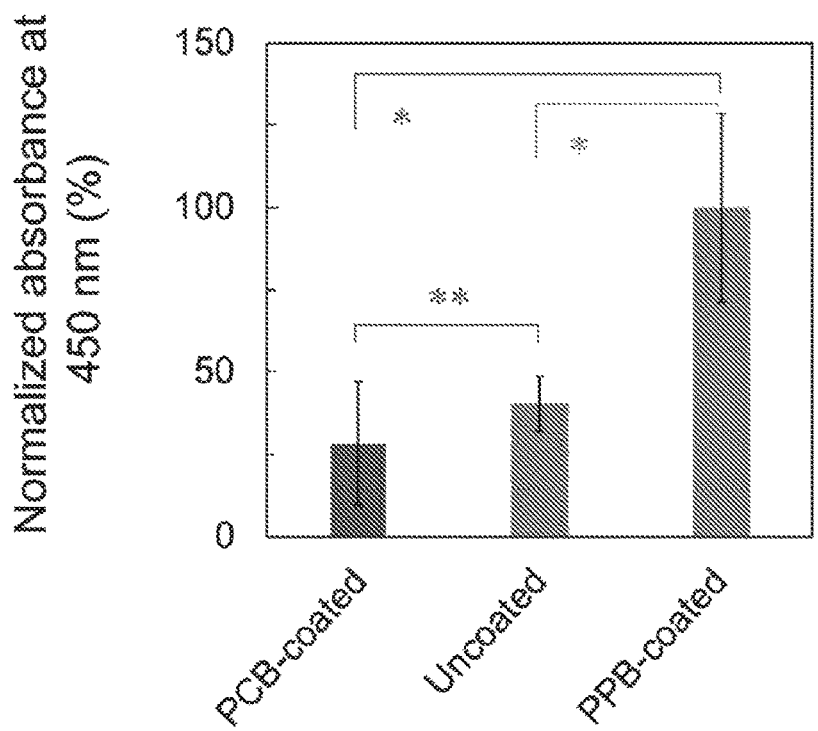
FIG. 21 compares activation of complement system on different PVC tubing: PCB-coated, uncoated, and PPB-coated. The absorbance at 450 nm wavelength has the direct proportion with concentration of terminal complement complexes (sC5b-9). Results are expressed as mean±SD (n=3; *p<0.001, and **p>0.05).

Complement activation. The complement system contains a series of over 20 proteins, circulating in the blood and tissue fluids, and is a primary contributor to the innate immune system that can clear foreign cells and organisms through direct lysis or by recruiting leukocytes that promote phagocytosis. The complement system is activated through three pathways: classical, alternative, and lectin pathway. The artificial biomaterials surface mainly triggers the alternative pathway by the adsorption of metastable complement protein C3b, which further initiates the whole complement cascade to induce formation of the terminal complement complexes (sC5b-9) that activate leukocytes and induce inflammatory response. Thus, the amount of sC5b-9 reflects the capability of biomaterials to the stimulation of the complement system. Importantly, both the terminal hydroxyl (—OH) groups and oxidation of poly(ethylene glycol) (PEG) chains strongly activate the complement system via the alternative pathway, so that the copolymer poly(PEGMA-co-BPAA) (PPB) will be a complement system activator (positive control). Results in FIG. 21 show that the serum contacted with either the PCB-coated or uncoated medical-grade PVC materials have a lower level of terminal complement complexes (sC5b-9) than PPB-coated ones, demonstrating a lower affinity of PCB polymers to activate complement system than PPB-coated surfaces. In addition, complement cascade was not completely inhibited on neither PCB-coated nor uncoated surfaces and there are no significant differences between them. This is because the extra-complement activation triggered at the interface between serum and air where plasma proteins get denatured and/or conformationally changed, and the activation was amplified and could not be terminated once it was triggered. For PPB-coated surfaces, the activation caused by PPB copolymers is much more severe than that from the serum/air interface, thus the whole activation level is high. Thus, these results demonstrate that the PCB polymers are not complement-activating biomaterials.

In summary, in one embodiment, the invention provides a functional random-type amphiphilic zwitterionic copolymer that includes both super-hydrophilic carboxybetaine (CB) units and hydrophobic/photosensitive N-(4-benzoylphenyl) acrylamide (BPAA) for use as a surface coating material. A CB random copolymer-modified commercial medical-grade PVC tubing can dramatically prevent blood protein fouling, human platelet activation, and complement activation under different dynamic perturbations. This surface coating lies within its simple yet effective large-scale applications via a dip-coating method, following by a UV light-irradiation. Its utility is further verified through its ability to achieve a noninvasive coating and a long-term duration. Furthermore, the polymer effectively prevented leaching of toxic plasticizer out from commercial medical-grade PVC materials. Thus, this method simultaneously solves the issues of non-biocompatibility and plasticizer leaching of PVC materials. The method is readily applicable to many other medical devices requiring biocompatible and additive-leaching-inhibiting surfaces.

Example 3 describes the preparation, characterization, and use of representative zwitterionic/photoreactive copolymers of the invention to prevent leaching of plasticizers from plastic surfaces.

Zwitterionic/Hydrophobic/Photoreactive Copolymers

In a further embodiment, the invention provides copolymers having zwitterionic groups, hydrophobic groups, and photoreactive groups, each pendant from the copolymer's backbone. The pendant zwitterionic groups impart low-fouling and functionalizable properties to surfaces that are treated or coated with the copolymer. The pendant hydrophobic groups serve to facilitate binding of the copolymer to the surfaces treated with the copolymer (e.g., via hydrophobic-hydrophobic interaction). The pendant photoreactive groups serve to facilitate copolymer crosslinking of the copolymer on the surface treated with the copolymer. The relative amounts of zwitterionic groups, hydrophobic groups, and photoreactive groups pendant from the copolymer's backbone are adjustable via copolymer synthesis to achieve the desired degree of low-fouling and functionalization and binding of the copolymer to the surface, each of which can be tuned depending on the nature (e.g., composition) of the surface to be treated or coated.

The certain of these embodiments, the invention provides a zwitterionic copolymer having superhydrophilic carboxybetaine (CB) units, hydrophobic binding n-butyl methacrylate (BMA) units, and hydrophobic/photosensitive N-(4-benzoylphenyl) acrylamide (BPAA) units that is useful as a surface coating material for platelet storage bags, methods for coating surfaces of platelet storage bags with the copolymer, and platelet storage bags coated with the copolymer.

Platelets are unique blood component which plays vital roles in hemostasis, thrombosis, inflammation, and wound healing. Platelet-based therapy, platelet transfusion, is an effective method to treat bleeding in people with either thrombocytopenia or platelet function defects. Importantly, the shelf-life of in vitro preserved platelets under the current standard condition is only half (4-7 days) of those in vivo bloodstream (8-10 days). Thus, improvement of platelet storage conditions to increase their shelf-life is required to mitigate the rising demand for platelets. The shelf-life of platelet is strongly affected by two reasons: (i) bacterial contamination and (ii) platelet storage lesion (PSL). The risk of bacterial contamination can be alleviated through a strict aseptic collection and highly sensitive bacterial diagnosis, while the predominant limitation factor PLS is strongly affected by storage conditions including container, the buffer component, temperature, respiration gas exchange efficiency, pH decreasing, lactate accumulation, consumption of nutrients and others. Although lots of attempts have been performed, including novel storage media additives, cold storage, and lyophilization, for practical application the current standard platelet preservation is still agitating platelets at room temperature (20-24° C.) inside a hydrophobic (e.g., poly(vinyl chloride)) storage bag. In fact, high-quality platelet storage has never been extended to 8 days. One of the keys that induce quality loss is the unfavorable interaction between the platelets and non-biocompatible storage bag surface, including irretrievable plasma protein denaturation, platelet activation and biofilm formation on hydrophobic plasticized PVC materials. Notably, medical grade hydrophobic PVC-based materials also shown serious thrombin generation and complement activation. Thus, imparting hydrophobic surface of storage bag with biocompatibility remains a major challenge.

Currently, biocompatibility of platelet bags is improved from two aspects: (i) changing the surface nano/microstructure/pattern to impart super-hydrophobicity along with the mixture of fouling release materials (e.g., silicone derivatives), and (ii) grafting neutral bioinspired nonfouling materials (e.g., zwitterionic polymers, poly(ethylene glycol), or poly(2-oxazoline)) to impart surface with super-hydrophilicity. Importantly, a non-fouling surface verified with traditional methods involving rinse procedures is still suspicious for being a biocompatible surface, because hydrophobic materials, particularly for those containing fouling lease moieties (e.g., silicone) could eventually exhibit low biofouling yet serious adverse biological responses (e.g., platelet activation, complement activation) during adhesion-release cycle. Although activation of platelets has been commonly considered as the subsequent response of adhesion caused by the adsorption of fibrinogen, non-platelet/protein adhesion surface do not prevent platelet activation completely. Therefore, evaluation of eventually amount of adsorbed protein/platelet is insufficient and it is crucial to study platelet properties in solution. Hydrophilic bioinspired nonfouling materials have been used for surface coating of medical devices for decades. As a unique zwitterionic material, poly(carboxybetaine) (PCB), shows undetectable protein adsorption (<0.3 ng/cm$^2$) against undiluted human serum or plasma and extensively reported in a broad range of biomedical applications without trigger unfavorable biological reactions, which exceeds the performance of conventional hydrophilic or amphiphilic polymers (e.g., PEG). The carboxybetaine (CB) groups, which are super-hydrophilic and charge-neutral with an inner salt structure, can form a layer of strongly bound water molecules that cannot be displaced by bioactive species, thus inhibiting the non-specific interaction between blood components and bag surface completely. Nonetheless, it remains a challenge to stabilize super-hydrophilic CB polymer directly onto the surface of commercialized hydrophobic products aiming for practical clinical applications with a simple and effective method.

In certain embodiments, the invention provides a copolymer of formula (IV):

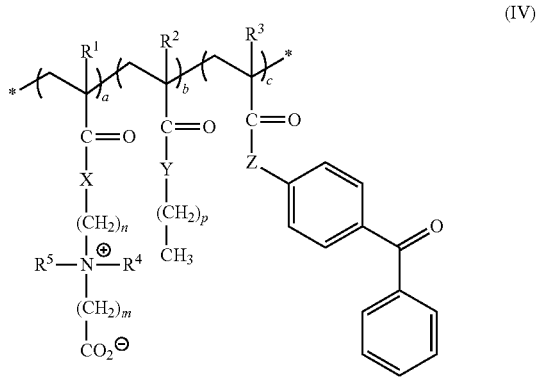

wherein
$R_1$, $R_2$, and $R_3$ are independently —(CH$_2$)$_x$H, where x is an integer from 0 to 20;
$R_4$ and $R_5$ are independently —(CH$_2$)$_x$H, where x is an integer from 0 to 20;
X is O or NH;
Y is O or NH;
Z is O or NH;
n is an integer from 1 to 20;
m is an integer from 1 to 20;
p is an integer from 0 to 20;
a is from about 0.10 to about 0.90 mole percent;
b is about 0.05 to about 0.95 mole percent;
c is from about 0.05 to about 0.95 mole percent;
a+b+c is 1.0; and
* represents the copolymer terminal groups.

In certain of these embodiments, $R_1$, $R_2$, and $R_3$ are independently selected from the group consisting of hydrogen and methyl.

In certain embodiments, $R_4$ and $R_5$ are independently selected from the group consisting of hydrogen and C1-C3 alkyl.

In certain embodiments, n is 1, 2, 3, 4, 5, or 6. In some embodiments, n is 2 or 3.

In certain embodiments, m is 1, 2, 3, 4, 5, or 6. In some embodiments, m is 1 or 2.

In certain embodiments, p is 1, 2, 3, 4, 5, or 6. In some embodiments, p is 3.

In certain embodiments, a is from about 0.70 to about 0.90 mole percent. In some embodiments, a is about 0.70 mole percent.

In certain embodiments, b is about 0.05 to about 0.25 mole percent. In some embodiments, b is about 0.20 mole percent.

In certain embodiments, c is about 0.05 to about 0.20 mole percent. In some embodiments, b is about 0.10 mole percent.

In one embodiment, $R_1$, $R_2$, and $R_3$ are hydrogen, $R_4$ and $R_5$ are methyl, and X is NH, Y is O, and Z is NH.

In another embodiment, $R_1$, $R_2$, and $R_3$ are hydrogen, $R_4$ and $R_5$ are methyl, and X is NH, Y is O, and Z is NH, n is 3, m is 1 and p is 3.

In certain of the above embodiments, a is about 0.70 mole percent, b is about 0.20 mole percent, and c is about 0.10 mole percent.

The following is a description of the preparation, characterization and use of representative zwitterionic/hydrophobic/photoreactive copolymers of the invention and their use in the compositions and methods of the invention.

Figures 22A, 22B:
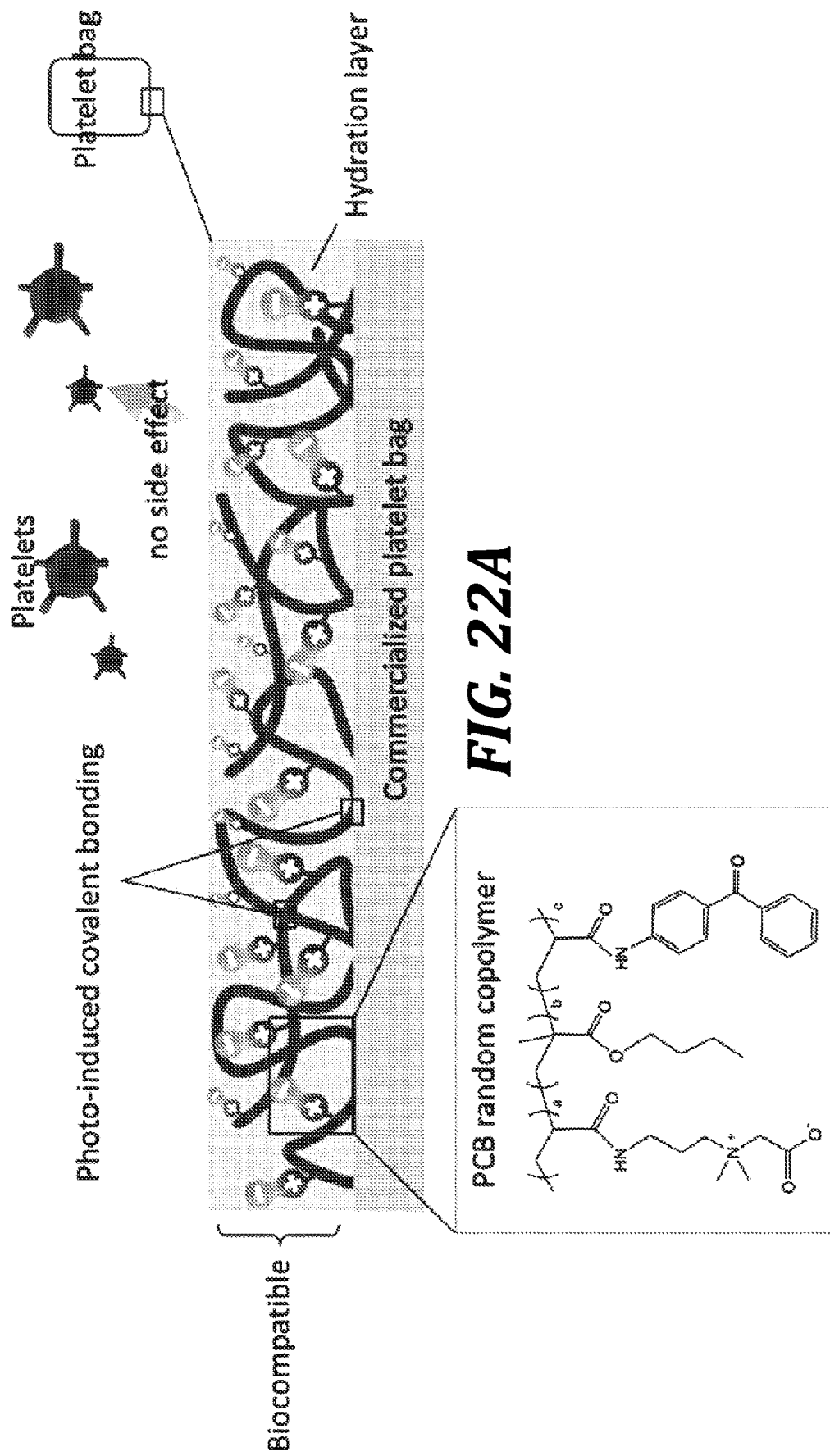
FIG. 22A is a schematic illustration of the surface modification of a representative commercial platelet bag with carboxybetaine (CB) copolymer.
FIG. 22B illustrates the chemical structure of a representative zwitterionic carboxybetaine (CB) copolymer of the invention.
Figure 22C:
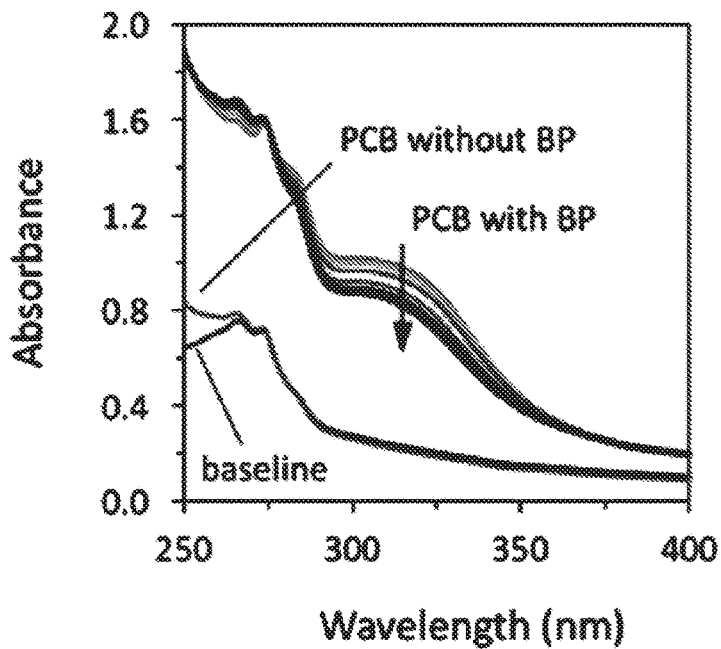
FIG. 22C illustrates that photosensitivity of a representative photoreactive CB copolymer.

The present invention provides a surface modification strategy for CB polymers to directly impart commercialized hydrophobic platelet storage bag with superhydrophilicity and nonfouling capability via an extremely simple and effective dip-coating technique. This is realized through covalently grafting CB copolymer to the internal surface of the storage bag by photo-induced conjugation and crosslinking (FIG. 22A). The CB moiety is super-hydrophilic which make it difficult to be attached to commercialized hydrophobic platelet storage bag, a hydrophobic binding group (n-butyl methacrylate, BMA) (e.g., 20 mol %), and a photosensitive groups (benzophenone) (e.g., 10 mol %) were included in the copolymer. Benzophenone groups have been widely used as photoinitiators to promote chemical conjugation, which produces a diradical under UV irradiation from 250 to 365 nm that abstracts aliphatic hydrogens to form a covalent binding. In order to introduce this binding group into the copolymer, a monomer N-(4-benzoylphenyl) acrylamide (BPAA) was synthesized and then copolymerized with other monomers to form the multifunctional copolymer (FIG. 22B). The presence of the functional units was verified with $^1$H NMR, where unit fraction of each monomer was obtained from the integral values of characteristic peaks: 3.82 ppm (—$CH_2$—, 2H) for the CB unit, 1.45-1.63 ppm (—$CH_2$—, 4H) for the BMA unit, and 6.80-7.85 ppm (benzophenone-H, 9H) for the BPAA unit. Results show that this polymer is very sensitive to UV light (312 nm) with the variation of absorbance spectrum from 300 to 350 nm, indicating the occurrence of photo-induced covalent binding (FIG. 22C).

Figure 23A:
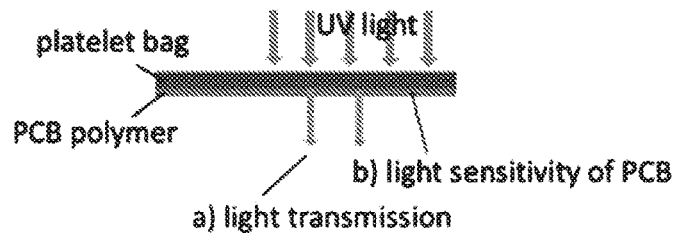
FIGS. 23A-23F illustrate representative surface modification in accordance with the invention: UV light permeability through commercialized platelet bag and permeated light-induced degradation of photosensitive (benzophenone) group (23A); surface morphology of platelet bag before and after coating (23B); X-Ray Photoelectron Spectroscopy (XPS) survey spectrum, high-resolution spectra of C 1s, O 1s and N 1s, and atom composition of five different samples: (1) PCB copolymer, (2) commercialized platelet bag, (3) commercialized platelet bag rinse with ethanol, (4) PCB-coated commercialized platelet bag, and (5) PCB-coated commercialized platelet bag soaked in buffer (23C-23E, respectively); and static air contact angle in distilled water and static water contact angle under dry condition (23F).
Figure 23B:
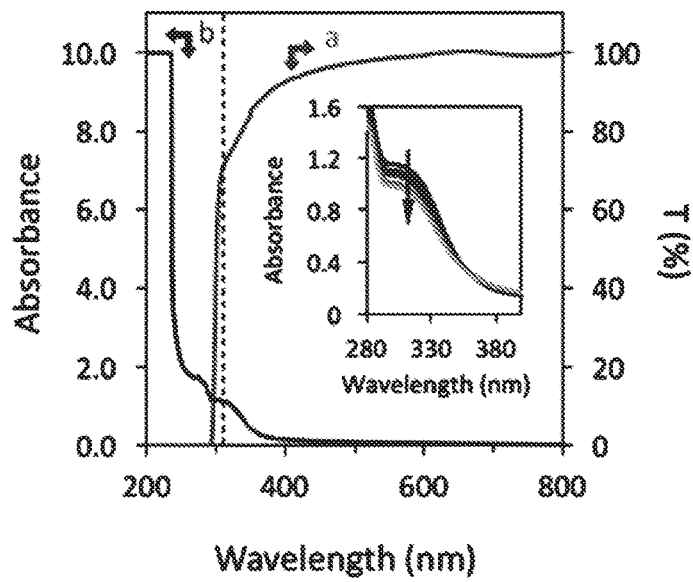

Modification of commercialized platelet bag will only happen on the internal surface without damage on original bag properties. To achieve this goal, a representative PCB polymer was dissolved into a DI water at an extremely low concentration (0.5 wt %) and subsequently injected into the bag with slightly shaking to ensure all the surface can be coated with the polymer. The UV light permeability test shows that this bag has 70% of light transmission at 312 nm wavelength, which is exactly the best irradiation wavelength for benzophenone group (FIG. 23A). Thus, the physically adhered polymer on the internal surface could be stabilized easily by applying external UV light. The coating thickness of copolymer using this technique is usually around <50 nm so that we could not see obvious differs from the SEM image (FIG. 23B). Interestingly, a textured surface was found and this morphology can prevent the internal surfaces from blocking during heat sterilization or blood processing. Other studies have shown that textured surfaces had much more serious biofouling compared with a smooth surface. Commercialized platelet bags are mainly made of PVC with a blended plasticizer (up to 40%) to ensure the intrinsic bag mechanical flexibility and gas permeation. Thus, a simple rinse of the surface with ethanol at a short period (10 s) was applied to reduce the leaching effect of plasticizer on PCB stability.

Figure 23C:
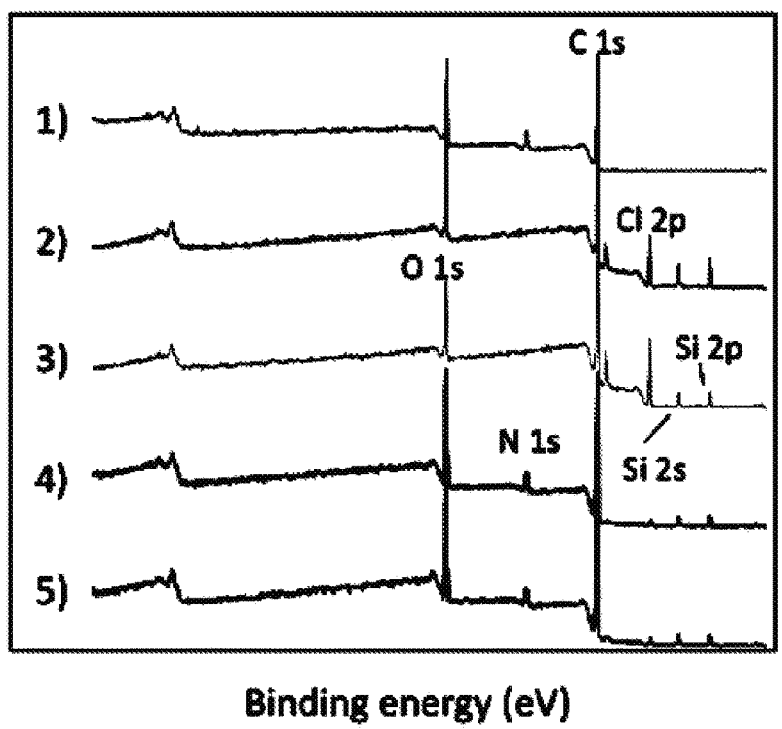
Figure 23D:
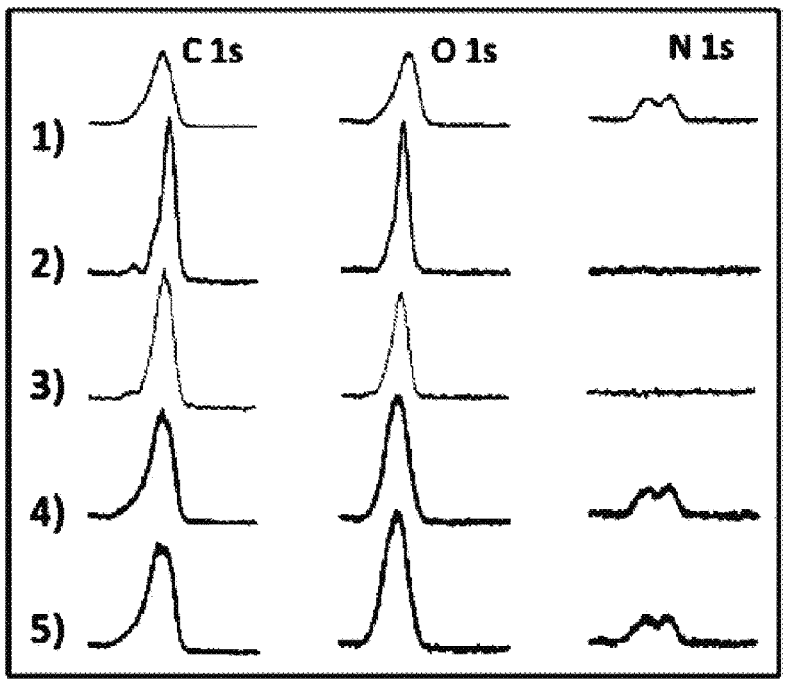
Figures 23E, 23F:
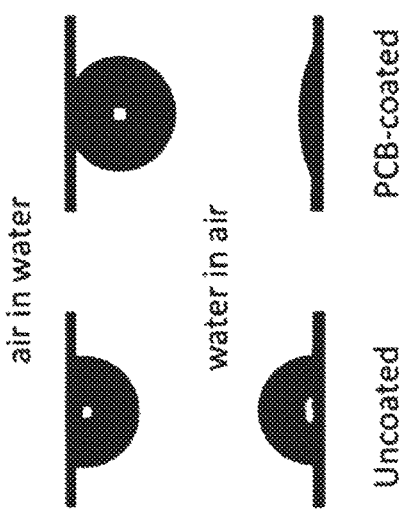
Figure 24A:
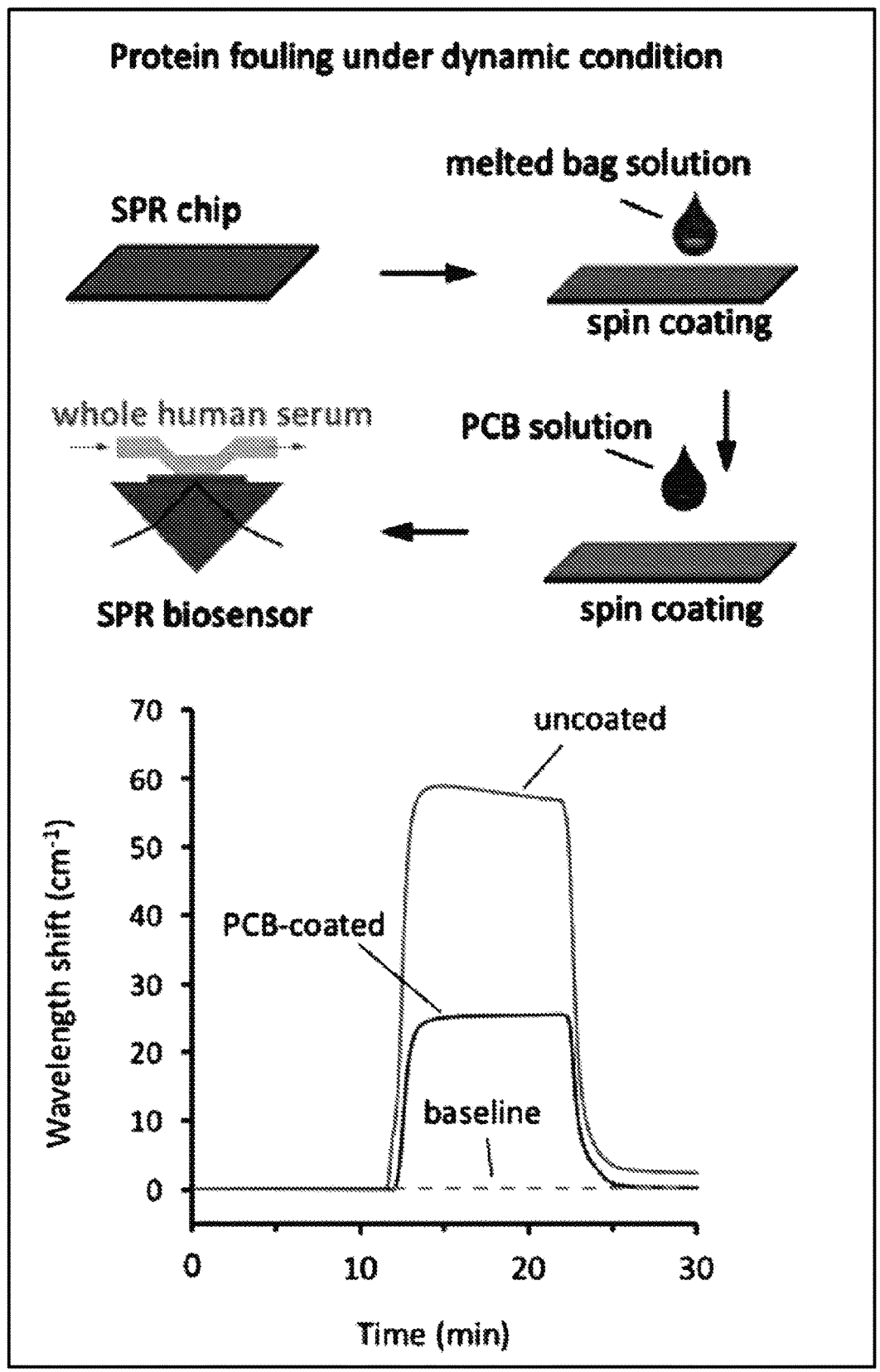
FIGS. 24A-24F illustrate nonfouling capability assessment of representative zwitterionic carboxybetaine (CB) copolymers of the invention: adsorption of human blood protein under dynamic condition tested by surface plasmon resonance (SPR) (24A); adsorption of human blood protein under static condition tested using a Micro BCA protein assay kit (24B); adhesion behavior of mammalian cells (NIH3T3) (24C); adhesion behavior of fresh human platelets (24D); adhesion and biofilm formation of a gram-positive strain of *Staphylococcus epidermidis* (24E) and a gram-negative strain of *Pseudomonas aeruginosa* (24F).

US Food and Drug Administration (FDA) require empty containers those will contact blood and blood components should not have leaching issues. Thus, x-ray photoelectron spectroscopy (XPS) was used to verify the PCB stability aiming to make the technique more closely to clinical application. The binding energy (BE) was corrected using the C is peak at 285 eV as a reference. XPS results show that PCB-coated surface has same N is peak as the original PCB polymer (FIGS. 23C and 23D) and a steady atom composition was obtained even after soaking in a buffer for 2 weeks (FIG. 23E), which can cover the entire lifetime period of platelets. Thus, PCB was successfully grafted on the internal surface of commercialized platelet bag with excellent stability. Interestingly, two silicon peaks (Si 2s and Si 2p) were observed from the survey spectrum, which demonstrates that this bag was treated with hydrophobic silicon-based materials with fouling releasing property. This phenomenon was further verified by real-time monitoring fouling against 100% human serum under dynamic condition (FIG. 24A). Hydrophilic nature is one of the key characteristics of PCB grafted surface. The water contact angles under dry condition and the air contact angles in an aqueous medium were measured. All contact angles were directly measured from the photographic images. The water contact angles of the PCB-coated surface were dramatically decreased from 90° to 10°, and air contact angles increased significantly from 80° to 160° (FIG. 23F). Thus, grafting of PCB copolymer converted hydrophobic surface to superhydrophilic.

Figure 24B:
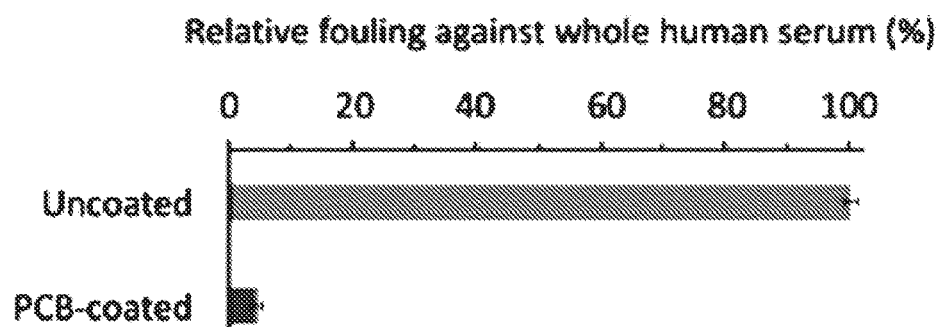

Biofouling on implanted, blood-contacting medical device surfaces remains to be of serious concern despite decades of research. The PCB-coated platelet bags will be used for platelet preservation, which involves direct contact with human blood proteins and platelets eventually. Thus, biofouling assessments are essential to evaluate the clinical application potential of current design strategy. Protein adsorption is the primary event that occurs on the surface of biomaterials in contact with a biological environment. Proteins might show different adsorption behavior under dynamic and static conditions. Thus, PCB-coated commercialized platelet bag against 100% human serum were evaluated under both dynamic condition and static condition using surface plasmon resonance (SPR) and a Micro BCA protein assay kit and, respectively. SPR is widely used to characterize in situ real-time interaction between polymer surface and proteins with a detection limit of <0.3 ng/cm$^2$. The SPR chips were successively spin-coated with commercialized platelet bag/THF solution and PCB copolymer/DI water solution. The thickness of the first layer (melted PVC bag) and the second layer (PCB polymer) was measured under dry conditions with a value of 18±1.2 nm and 20±2.1 nm. FIG. 24A shows the change in the SPR signal attributed to serum adsorption as a function of time. For the chip coated with melted platelet bag, the wavelength ship increased and subsequently showed a steady decreasing tendency while continuing flowing 100% human serum, indicating a fouling release behavior possible induced by silicone-based additives confirmed by XPS results. The sharp increase in signal at the point of serum injection was attributed to the change in the bulk refractive index. The amount of nonspecific adsorption was evaluated from the wavelength shift from before protein injection to after washing with buffer. The wavelength shifts of the PCB-coated and uncoated chips were 0.20 and 2.24 nm, corresponding to serum adsorption of 3.4 and 38.1 ng/cm$^2$, respectively. This result has shown that PCB-coated surface has ultra-low fouling (<5.0 ng/cm$^2$) capability and less than 10% of fouling compared with uncoated surfaces under a dynamic condition which is consisted with Micro BCA protein assay kit result (FIG. 24B).

Figure 24C:
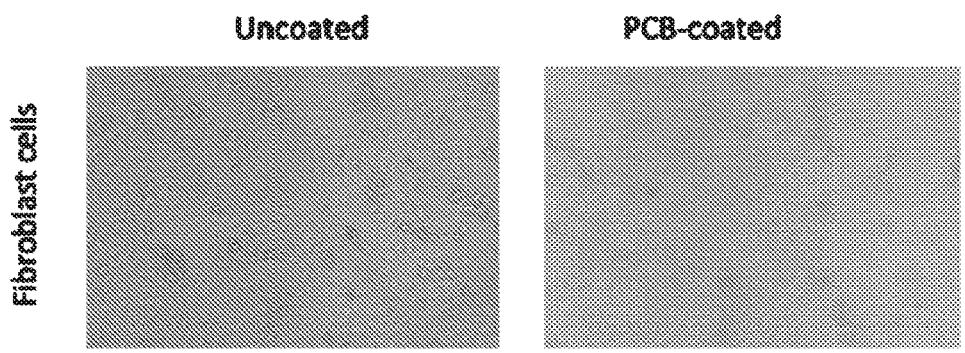
Figure 24D:
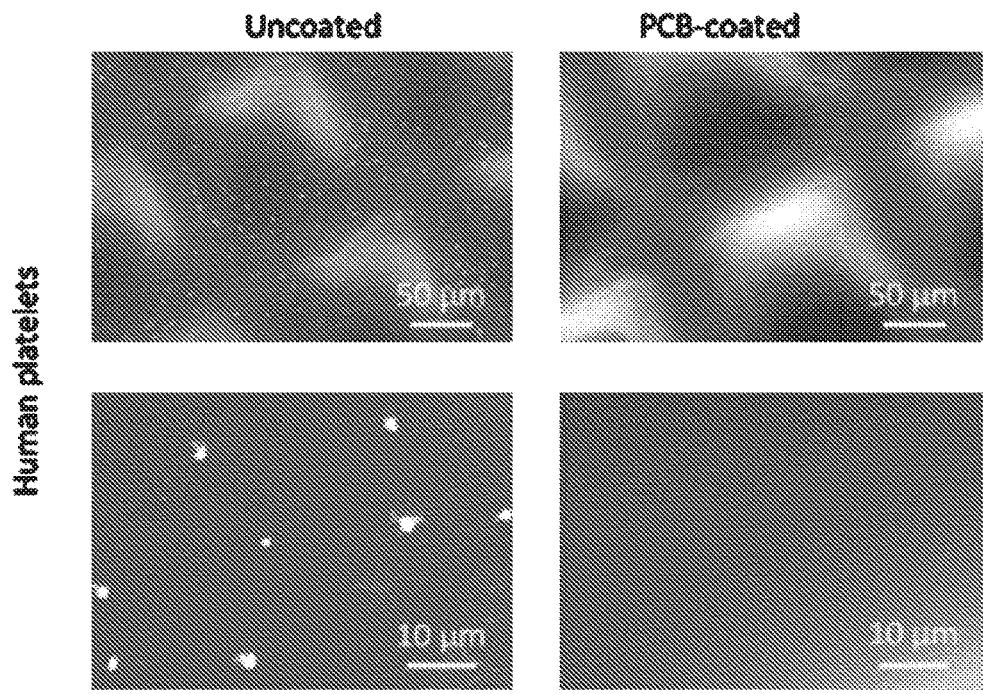
Figure 24E:
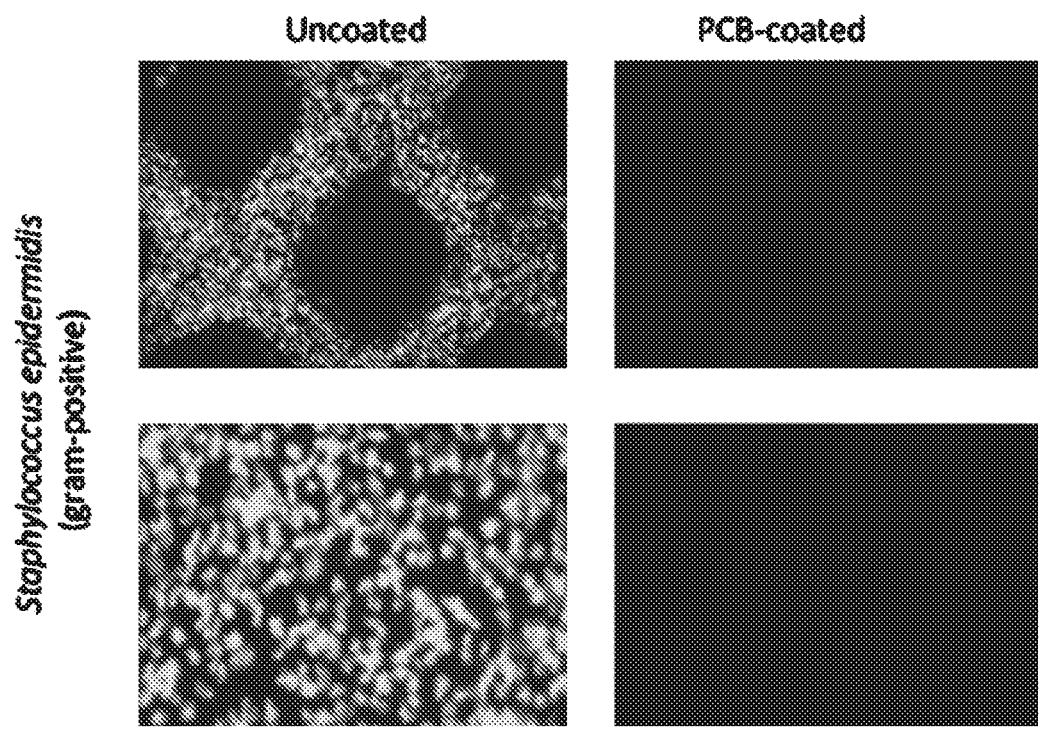
Figure 24F:
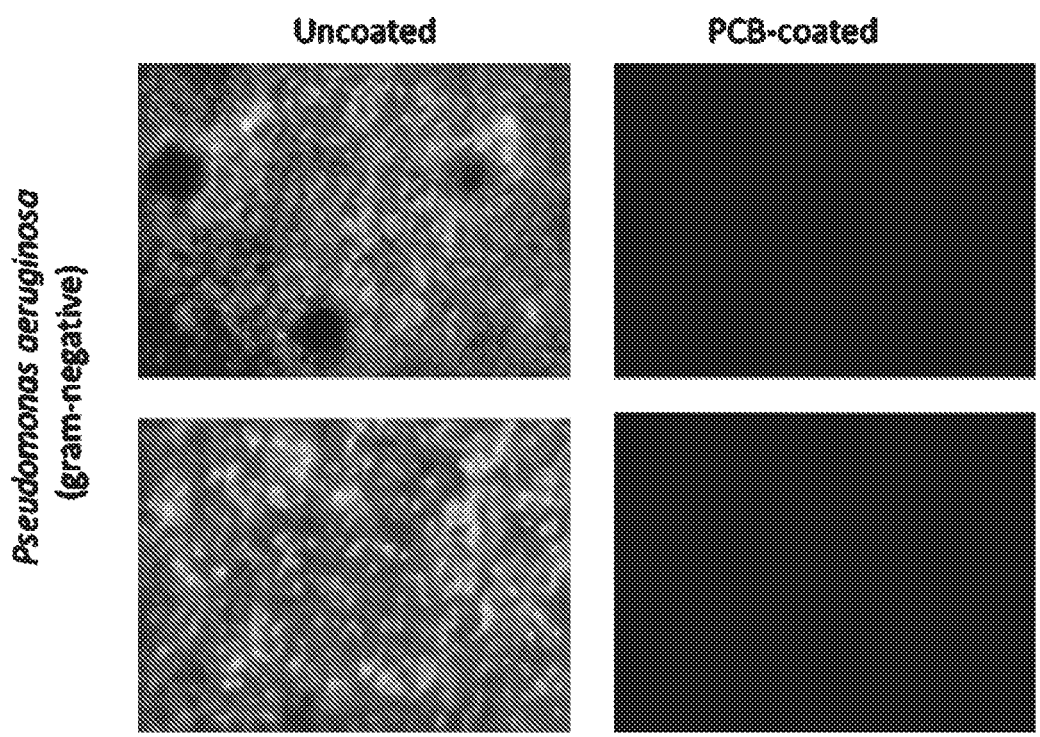

Fibronectin plays a major role in the adhesion of many cell types, including fibroblast cells. Thus, adhesion of NIH3T3 fibroblast cells was completely inhibited on the PCB-coated nonfouling surface (FIG. 24C). The platelets adhesion is strongly depended on the adsorbed fibrinogen/ fibrin, Von Willebrand factor (VWF), fibronectin and others, and a 10 ng/cm$^2$ fibrinogen adsorption can induce a full-scale blood platelet adhesion. A nonfouling surface with PCB hydrophilic hydration layer can effectively protect the surface from fouling and activation of platelets (FIG. 24D). Although PVC-based materials have shown a binding affinity to bacteria to form biofilm and the gram-positive strain of *Staphylococcus epidermidis* shows slow growth rate with missed detection, PCB-coated surfaces inhibited adhesion of bacteria completely (FIGS. 24E and 24F). Interestingly, bacteria preferred to grow and form the biofilm on the concave area of textured surfaces.

Figure 25A:
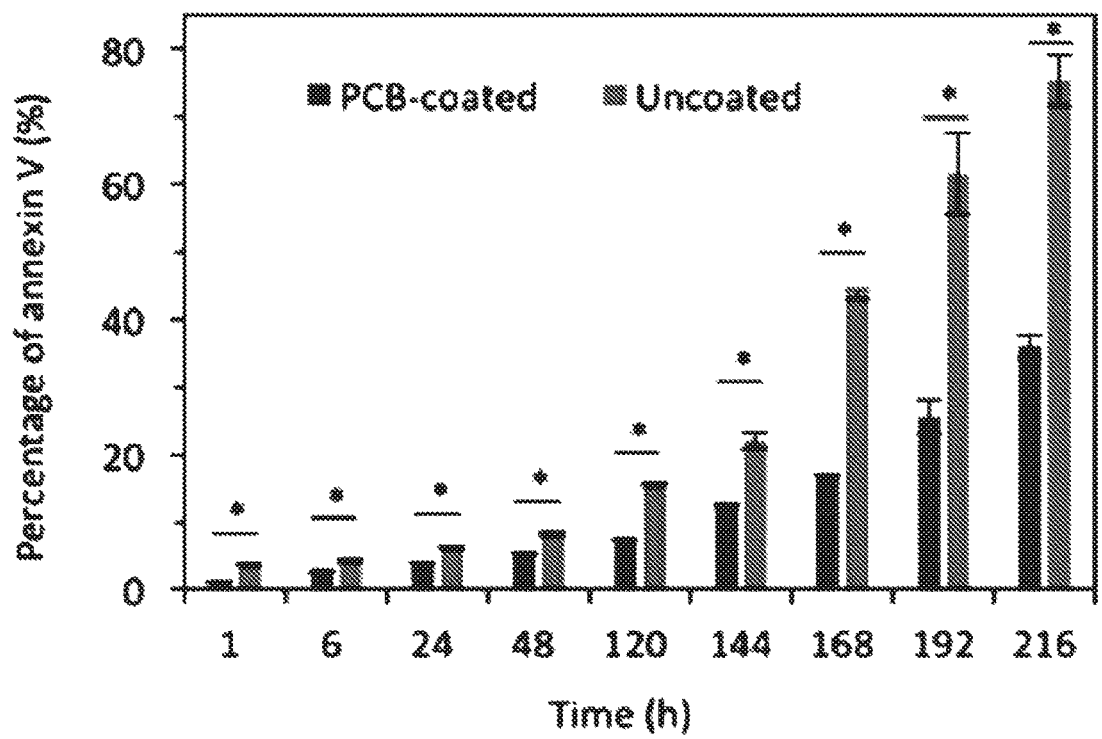
FIGS. 25A-25H provide an evaluation of preserved platelets in accordance with a representative method of the invention: expression level of annexin V on preserved platelets (25A); expression level of p-selectin (CD62) on preserved platelets (25B); morphology score of preserved platelets (25C); von Willebrand Factor (VWF) binding affinity (25D); time to reach 100 nN threshold during plug test (25E); and pH (25F), glucose level (25G), and lactate level (25H) in the platelet preservation solution.
Figure 25B:
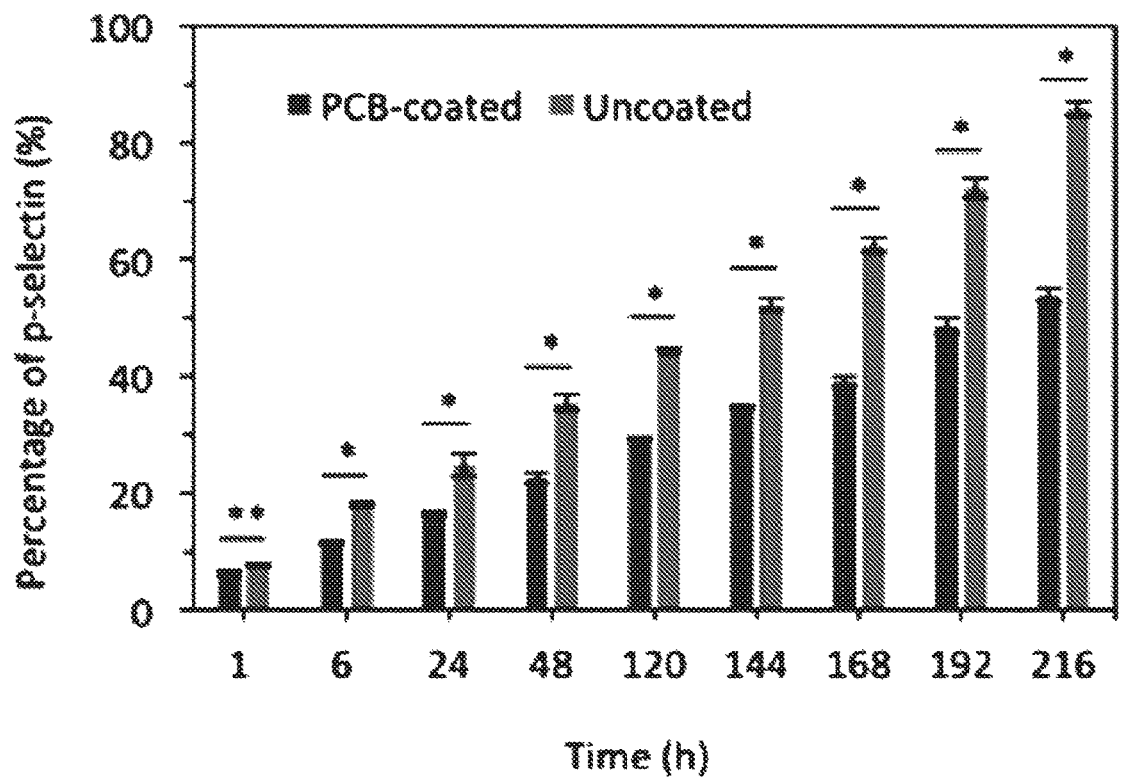
Figure 25C:
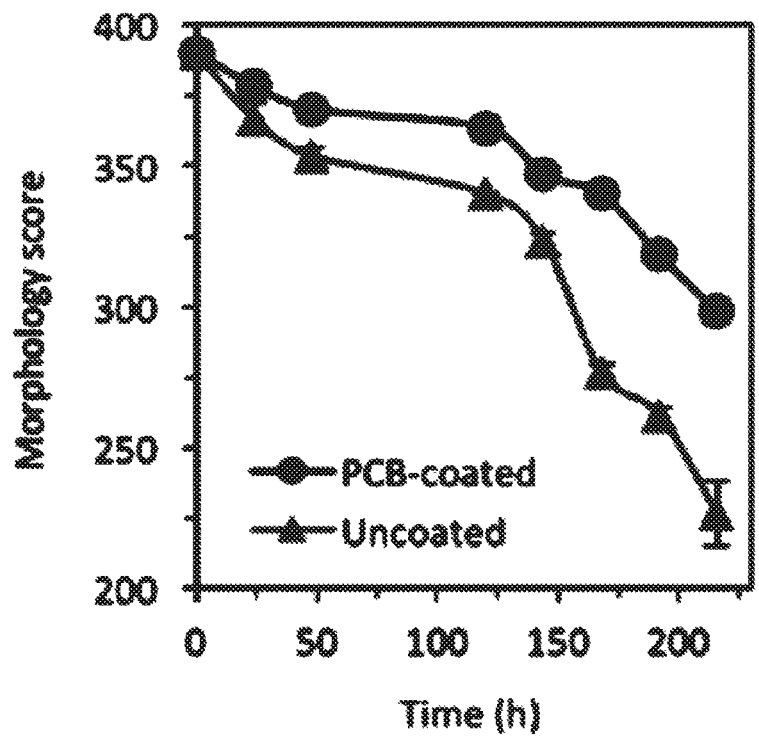
Figure 25D:
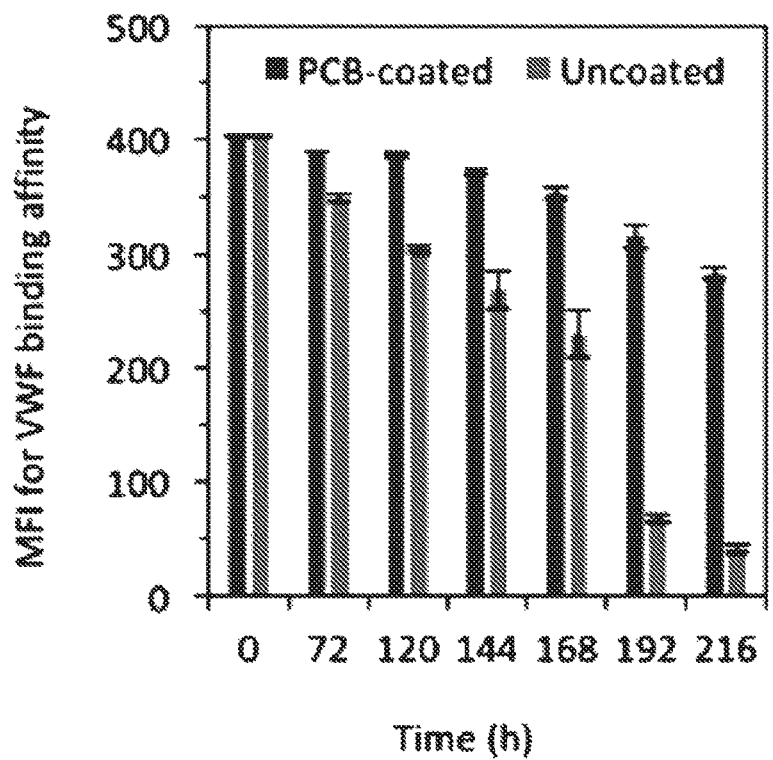
Figure 25E:
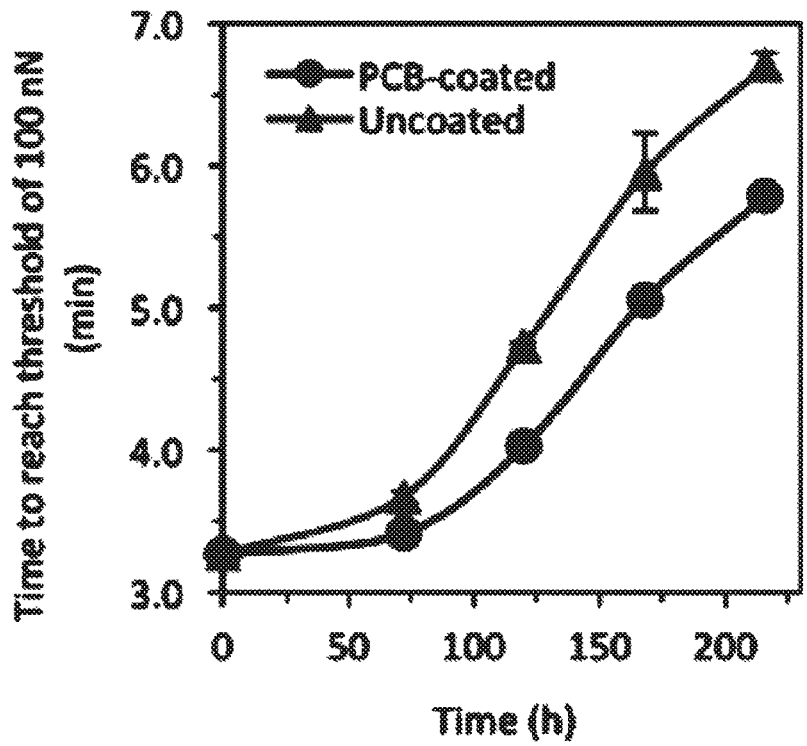
Figure 25F:
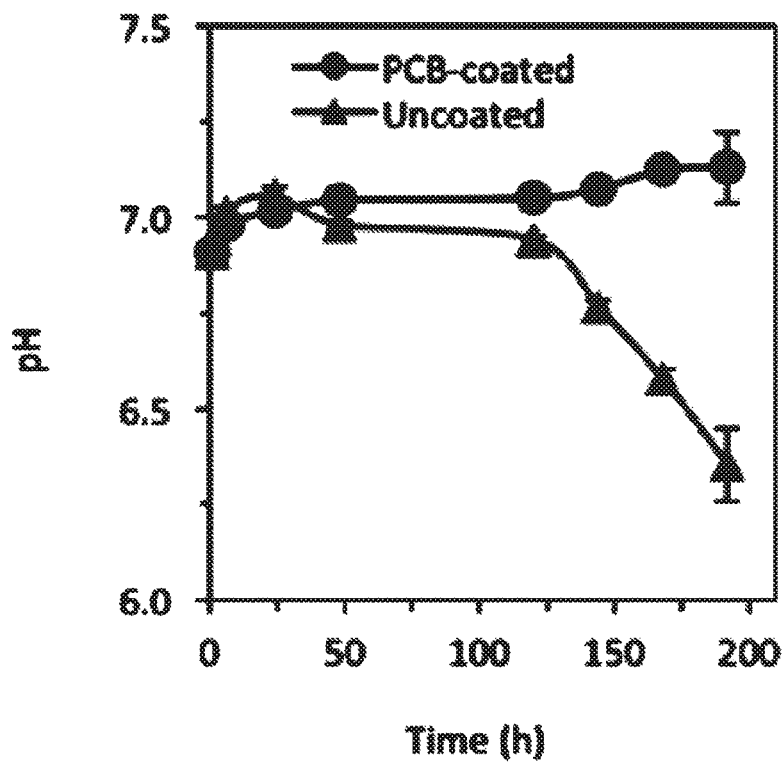
Figure 25G:
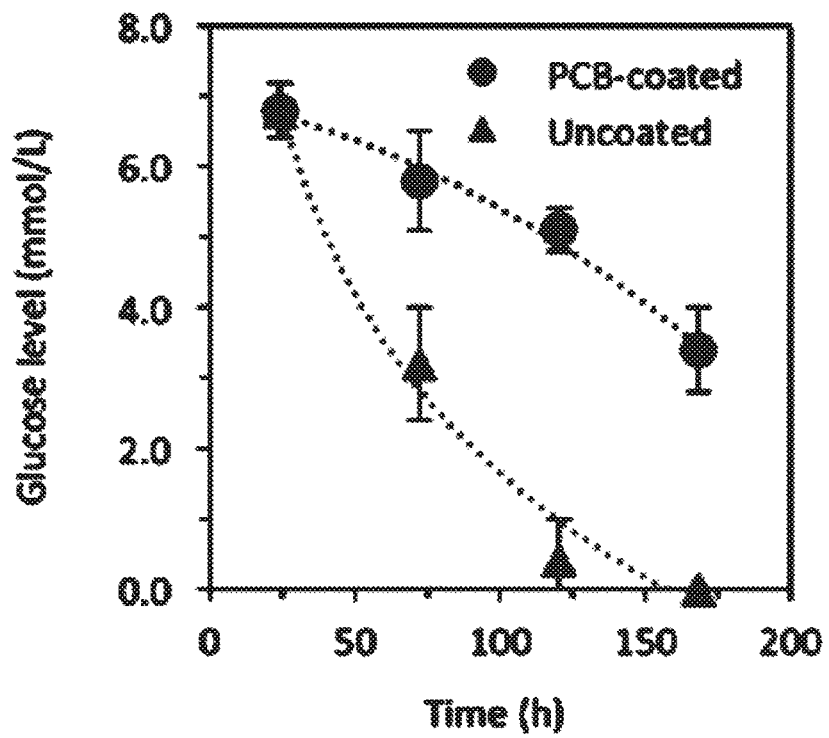
Figure 25H:
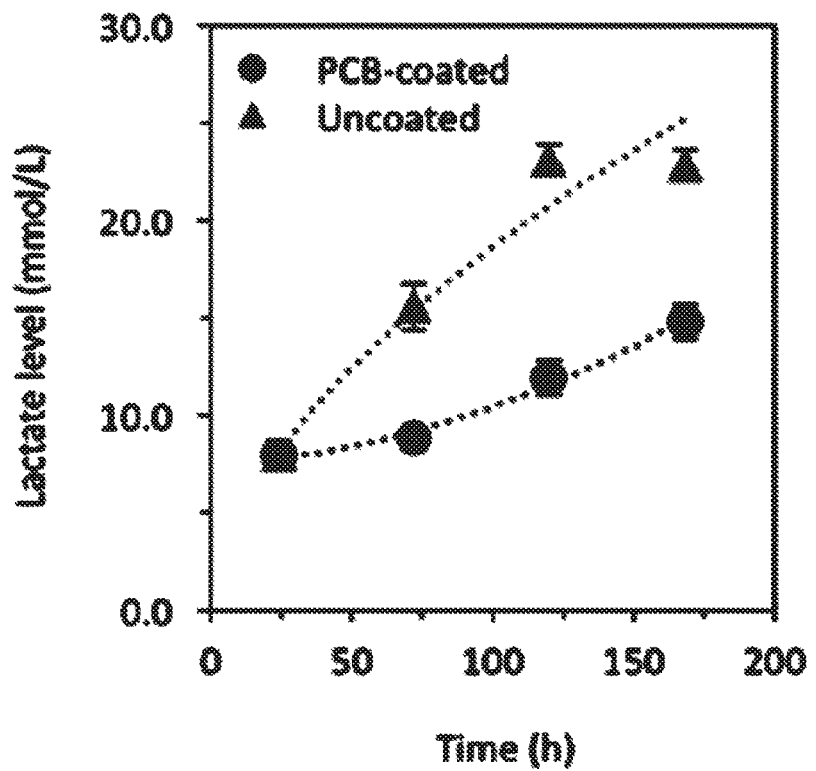

Although activation of platelets has been considered as the subsequent response of adhesion caused by the adsorption of fibrinogen, non-platelet/protein adhesion surface do not prevent platelet activation completely. Annexin V is commonly used to detect apoptotic cells by its capability to bind phosphatidylserine, which is a marker of platelet apoptosis when it is on the outer leaflet of the plasma membrane. Thus, a higher binding level of annexin V stands for a more serious cell apoptosis. Results show that platelets those preserved in the PCB-coated hydrophilic bag has a lower binding level of annexin V compared with those in uncoated bags, indicating that PCB surface can effectively maintain platelets viability (FIG. 25A). Platelets remain in the resting state under normal conditions, however, when suffering vascular injury, shear stress due to changing velocity of the bloodstream, along with subsequent cell signaling events following, cause irreversible platelet activation. p-Selectin (CD62) is a glycoprotein and well-described marker of platelet activation. During platelet activation, p-selectin translocated from intracellular granules to the external membrane. FIG. 25B shows that activation of platelets was effectively inhibited on PCB-coated bag duo to lower non-specific platelet-surface interaction, compared with the controlled surfaces. The activation level of platelets in the PCB-coated bag at 8 days is comparable with control samples at 5 days. Nonetheless, platelets still have very high metabolically activity compared with those stored under refrigeration, so activation level shows a steadily increasing tendency even for PCB-coated ones. At the same time, high metabolically activity and activation of platelets may cause increased glucose consumption (FIG. 25G), lactate accumulation (FIG. 25H), and as a consequence, a fall in pH if exceeded the buffer capacity (FIG. 25F). A pH drop to 6.2 or below will significantly reduce the survival rate of platelet during transfusion. For PCB-coated samples, the glucose consumption and lactate accumulation did not seriously affect the pH value (>6.8) compared to controlled ones. The morphology score (MS) is used as a simple indicator of platelet health and is defined as 4×(disc %)+2×(spheres %)+(dendrite %). A higher percentage of platelet with health disc morphology will cause higher MS value. MS value of platelet storage in PCB-coated bags shows much higher MS even after 8 days (FIG. 25C). The binding of VWF to platelets is dependent on the conformation of the A1 domain which binds to platelet GPIbα, and the higher MFI (mean fluorescence intensity) correlated to higher binding affinity. This is a judgment criterion of platelet function on hemostasis. Results show that higher MFI (320) on PCB-coated sample at 8 days than controlled sample at 5 days (300) (FIG. 25D). All of the platelet evaluation results above indicate that zwitterionic PCB copolymer surface can effectively alleviate nonspecific interaction induced platelet lesion, which makes our polymer and surface modification strategy has more potential for clinical applications.

In summary, in one aspect, the invention provides a multifunctional random-type amphiphilic zwitterionic copolymer consisting of superhydrophilic carboxybetaine (CB) units, hydrophobic n-butyl methacrylate (BMA) units, and photosensitive N-(4-benzoylphenyl) acrylamide (BPAA) units for use as a surface coating material. This polymer can non-invasively impart commercialized hydrophobic platelet storage bag with super-hydrophilicity and non-fouling capability via a simple and effective dip-coating method. The human platelets preserved into this PCB copolymer coated platelet bag shows significantly improved properties (e.g., higher viability, lower activation rate, higher morphology score, and higher binding affinity to VWF) than current standard preservation method. The coating strategy provides a simple yet effective large-scale applications via a dip-coating method. Thus, this technique is promising for a wide range of medical and engineering applications, particularly for extending human platelet shelf-life beyond current standard methods.

Example 4 describes the preparation, characterization, and use of representative zwitterionic/hydrophobic/photoreactive copolymers of the invention.

Zwitterionic Copolymer Coating Compositions and Substrate Coated Surfaces

In another aspect of the invention, coating compositions are provided. The coating compositions include a zwitterionic copolymer as described herein (e.g., a copolymer of formulae (I), (II), (III), or (IV)). In addition to the zwitterionic copolymer, the coating composition optionally includes a carrier or vehicle effective for delivering the zwitterionic copolymer to the surface to be coated. Representative carriers include solvents, such as organic solvents, aqueous solvents, and mixed organic and aqueous solvents, in which the zwitterionic copolymer to be applied is soluble. The coating compositions are effect for providing a coating for a surface of a substrate.

For embodiments that use a zwitterionic copolymer that includes a photoreactive group, the coating is derived from a copolymer as described here. In the process of immobilizing the copolymer to a surface, the copolymer coated on the surface is irradiated to effect copolymer crosslinking and depending on the surface, the copolymer is crosslinked to the surface. Therefore, for these embodiments, the coating comprises a crosslinked zwitterionic copolymer and depending on the surface, crosslinked zwitterionic copolymer that is also crosslinked to the surface.

In a further aspect, the invention provides a substrate having at least a portion or all of its surface (e.g., external or internal) coated with a copolymer of the invention (e.g., a copolymer of formulae (I), (II), (III), or (IV)) or a composition comprising a copolymer of the invention.

Suitable substrates have a surface that is a hydrocarbon-based surface. Suitable surfaces include plastic surfaces and polymeric surfaces. Representative surfaces include polyolefin, polyester, polycarbonate, polyurethane (PU), polysulfone (PSF), poly(ether sulfone) (PES), polyamide, polyacrylic, polyimide, aromatic polyester, polyethylene (PE), polypropylene (PP), polystyrene (PS), poly(ethylene terephthalate) (PET), poly(vinyl chloride) (PVC), poly(dimethyl siloxane) (PMDS), poly(vinylidiene fluoride) (PVDF), poly (lactic acid) (PLA), and poly(methyl methacrylate) (PMMA) surfaces. In certain embodiments, the surface is a polyvinyl chloride surface or a polyurethane surface. In other embodiments, the surface is a cellulose or cellulose acetate surface.

Other suitable surfaces include metal, metal alloy, and ceramic surfaces.

In certain embodiments, the invention provides a medical device having at least a portion or all of its surface coated with a copolymer of the invention or a composition comprising a copolymer of the invention. Suitable medical devices include devices that have a surface that is a hydrocarbon-based surface. Representative surfaces include polyolefin, polyester, polycarbonate, polyurethane (PU), polysulfone (PSF), poly(ether sulfone) (PES), polyamide, polyacrylic, polyimide, aromatic polyester, polyethylene (PE), polypropylene (PP), polystyrene (PS), poly(ethylene terephthalate) (PET), poly(vinyl chloride) (PVC), poly(dimethyl siloxane) (PMDS), poly(vinylidiene fluoride) (PVDF), poly(lactic acid) (PLA), and poly(methyl methacrylate) (PMMA) surfaces. In certain embodiments, the surface is a polyvinyl chloride surface or a polyurethane surface. In other embodiments, the surface is a cellulose or cellulose acetate surface.

Representative devices include devices that are a plate, a dish, a tube, a tip, a catheter, an artificial blood vessel, an artificial heart, or an artificial lung.

In one embodiment, the invention provides polyvinyl chloride tubing at least a portion or all of its internal surface coated with a composition or copolymer of the invention.

In another embodiment, the invention provides polyurethane tubing at least a portion or all of its internal surface coated with a composition or copolymer of the invention.

In a further embodiment, the invention provides a polysulfone dialysis membrane at least a portion or all of its surface coated with a composition or copolymer of the invention.

In another embodiment, the invention provides a hydrocarbon-based membrane container at least a portion or all of its internal surface coated with a composition or copolymer of the invention.

In another embodiment, the invention provides a platelet storage bag having at least a portion or all of its internal surface coated with a composition or copolymer of the invention.

Other representative devices where at least one or more surfaces that are advantageously coated with a copolymer of the invention or a composition comprising a copolymer of the invention include implanted/unimplanted medical devices from Class I, Class II, or Class III.

As noted above, the zwitterionic copolymers described herein are useful for coating blood-contacting surfaces to impart a variety of advantages to those surfaces. Among devices that include blood-contacting surfaces are components of hemodialysis devices. Components of hemodialysis devices that are advantageously treated with the zwitterionic copolymers described herein include dialysis membranes (e.g., blood purification membranes) and dialysis tubing (e.g., polyvinyl chloride and polyurethane tubing). Surfaces of the membranes that are advantageously coated with the zwitterionic copolymers include cellulose, cellulose acetate, poly(sulfone) (PSF), poly(ether sulfone) (PES), poly(dimethyl siloxane) (PMDS), poly(vinylidiene fluoride) (PVDF), poly(lactic acid) (PLA), polyurethane (PU), and polypropylene (PP).

Methods for Using the Zwitterionic Copolymers

In a further aspect, the invention provides methods for using the zwitterionic copolymers (e.g., a copolymer of formulae (I), (II), (III), or (IV)) and copolymer compositions of the invention.

In one embodiment, the invention provides a method for coating a surface of a substrate, comprising contacting the surface of the substrate with a copolymer of the invention (e.g., a copolymer of formulae (I), (II), (III), or (IV)) or a composition comprising a copolymer of the invention.

In a related embodiment, the invention provides a method for coating a surface of a substrate nonfouling, comprising coating at least a portion of the surface of the substrate with a copolymer of the invention (e.g., a copolymer of formulae (I), (III), or (IV)) or a composition comprising a copolymer of the invention, and irradiating the surface of the substrate with light effective to crosslink the copolymer on the surface.

In another embodiment, the invention provides methods for rendering a surface of a substrate nonfouling, comprising coating at least a portion of the surface of the substrate with a copolymer of the invention (e.g., a copolymer of formulae (I), (II), (III), or (IV)) or a composition comprising a copolymer of the invention.

In a related embodiment, the invention provides a method for rendering a surface of a substrate nonfouling, comprising coating at least a portion of the surface of the substrate with a copolymer of the invention (e.g., a copolymer of formulae (I), (III), or (IV)) or a composition comprising a copolymer of the invention, and irradiating the surface of the substrate with light effective to crosslink the copolymer on the surface.

In a further embodiment, the invention provides a method for inhibiting blood protein adsorption on a surface of a substrate, comprising coating at least a portion of the surface of the substrate with a copolymer of the invention (e.g., a copolymer of formulae (I), (II), (III), or (IV)) or a composition comprising a copolymer of the invention.

In a related embodiment, the invention provides a method for inhibiting blood protein adsorption on a surface of a substrate, comprising coating at least a portion of the surface of the substrate with a copolymer of the invention (e.g., a copolymer of formulae (I), (III), or (IV)) or a composition comprising a copolymer of the invention, and irradiating the surface of the substrate with light effective to crosslink the copolymer on the surface.

In another embodiment, the invention provides a method for coating an internal surface of a platelet storage bag, comprising contacting an internal surface of a platelet storage bag with a copolymer of the invention (e.g., a copolymer of formulae (I), (III), or (IV)) or a composition comprising a copolymer of the invention, and irradiating the contacted internal surface of the platelet storage bag with light effective to crosslink the copolymer on the surface.

In a further embodiment, the invention provides a method for coating an internal surface of a polyvinyl chloride tubing, comprising contacting an internal surface of a platelet storage bag with a copolymer of the invention (e.g., a copolymer of formulae (I), (III), or (IV)) or a composition comprising a copolymer of the invention, and irradiating the contacted internal surface of the polyvinyl chloride tubing with light effective to crosslink the copolymer on the surface.

In other embodiments, the invention provides methods for inhibiting or preventing leaching of a plasticizer from a surface of a substrate. In certain of these embodiments, the method comprises:

(a) coating at least a portion of a surface of a substrate with a composition comprising a copolymer to provide a coated surface, the copolymer comprising first repeating units and second repeating units, wherein each of the first repeating units comprises a pendant zwitterionic group, and wherein each of the second repeating units comprises a pendant photoreactive group effective for crosslinking the copolymer on a surface, to provide a coated surface; and (b) irradiating the coated surface with light effective to crosslink the copolymer on the surface, thereby providing a coated surface effective for inhibiting or preventing leaching of a plasticizer from the surface.

In certain embodiments, the copolymer further comprises third repeating units, wherein each of the third repeating units comprises a pendant hydrophobic group effective for adsorbing the copolymer to the surface. Zwitterionic copolymers useful include those of formulae (I), (III), and (IV).

In certain of the above embodiments, contacting the surface with the composition comprises dipping the surface into the copolymer or composition. In other of these embodiments, contacting the surface with the composition comprises spraying, spinning, brushing, or rolling the copolymer or composition onto the surface.

In certain embodiments of the methods of the invention, contacting the surface with the copolymer or copolymer composition, or coating the surface with the copolymer or copolymer composition, comprises dipping the surface into the copolymer or copolymer composition. In other of these embodiments, contacting the surface with the copolymer or copolymer composition, or coating the surface with the copolymer or copolymer composition, comprises spraying, spinning, brushing, or rolling the copolymer or copolymer composition onto the surface.

As used herein, the term "about" refers to ±5% of the specified value.

The following examples are provided for the purpose of illustrating, not limiting the invention.

EXAMPLES

Example 1

Preparation, Characterization, and Use of Representative Zwitterionic/Hydrophobic Copolymers In this example, the preparation, characterization, and use of representative zwitterionic/hydrophobic copolymers of the invention is described.

Materials. Carboxybetaine acrylamide, 1-carboxy-N,N-dimethyl-N-(3'-acrylamidopropyl) ethanaminium inner salt (CB1) and carboxybetaine methacrylate, 2-carboxy-N,N-dimethyl-N-(2'-methacryloyloxyethyl) ethanaminium inner salt (CB2), were synthesized according to a previously reported method, respectively. The following materials and reagents were obtained from Sigma-Aldrich (St. Louis, Mo., USA) and used without any further purification: 2,2'-azobisisobutyronitrile (AIBN), human plasma fibrinogen (Fg), human serum albumin (HSA), human blood γ-globulin, sodium acetate (SA), N-[tris(hydroxymethyl)methyl]-3-aminopropanesulfonic acid (TAPS), 1-decanethiol, sodium n-dodecyl sulfate (SDS), N-hydroxysuccinimide (NHS), N-ethyl-N'-(3-diethylaminopropyl) carbodiimide hydrochloride (EDC). n-Butyl methacrylate (BMA) was purchased from Tokyo Chemical Industry Co., Ltd. (Portland, Oreg., USA). Anti-fibrinogen antibody conjugated with horseradish peroxidase (HRP) was purchased from Novus Biologicals (Littleton, Colo., USA). O-phenylenediamine dihydrochloride (OPD) was obtained from Pierce (Rockford, Ill., USA). Phosphate-buffered saline (10×, solution), hydrogen peroxide ($H_2O_2$, 30% in water) and hydrochloric acid (HCl) were obtained from Fisher Scientific Co. (Fair Lawn, N.J.). Normal human blood serum (pooled mixed gender) was purchased from BioChemed Services (Winchester, Va.). Micro BCA protein assay kit and RBS™ 35 Concentrate were purchased from Thermo Scientific (Waltham, Mass.). The multi-well plate with an ultra-low attachment surface was purchased from Corning Costar Corp. (Corning, N.Y.). Ethanol (200 proof) was purchased from Decon Labs (King of Prussia, Pa.). The water was obtained from a Millipore water purification system with a minimum resistivity of 18.0 MΩcm. Other organic reagents and solvents were commercially available as extra-pure grade reagents and were used as received.

Synthesis of Polymers. Amphiphilic random copolymers, poly(CB1-co-BMA) (PCB1) and poly(CB2-co-BMA) (PCB2) were synthesized by conventional free radical polymerization method using AIBN as an initiator, and similar method was reported previously (Lin, X.; Konno, T.; Ishihara, K., Cell-Membrane-Permeable and Cytocompatible Phospholipid Polymer Nanoprobes Conjugated with Molecular Beacons. *Biomacromolecules* 2014, 15 (1), 150-157; and Lin, X.; Fukazawa, K.; Ishihara, K., Photoinduced inhibition of DNA unwinding in vitro with water-soluble polymers containing both phosphorylcholine and photoreactive groups. *Acta Biomater.* 2016, 40, 226-234). In brief, desired amounts of CB monomer, BMA (various molar ratio of CB/BMA: 2/8, 3/7, 4/6, 5/5, 6/4, 8/2), and AIBN were dissolved in ethanol. The solution was transferred to a Pyrex® Vista™ glass tube reactor and further purged with nitrogen gas for 30 min at room temperature. Polymerization was performed in the sealed glass tube under a protection atmosphere of nitrogen gas. After polymerization, the reaction solution was slightly dropped into a mixed solvent of ether/chloroform to precipitate copolymers. The copolymer was filtered off and collected as a white powder after vacuum desiccation for 24 h at room temperature. The residual CB monomer was removed by washing the collected white polymer powder with a large amount of Millipore water. Then, the copolymer was filtered off again, frozen by liquid nitrogen and treated with a lyophilizer (Labconco Co., Ltd., Kansas City, Mo.) at −80° C. for 48 h to convert them into dried white powder. The chemical structures of purified copolymers were confirmed using $^1$H-NMR (AV-500, Bruker, German) and polymers were cryopreserved under −20° C.

Optimization of Coating Conditions. Polypropylene (PP) substrates (ePlastic, San Diego, Calif., USA) were cut into 0.5 cm×0.5 cm, ultrasonically washed in ethanol for 10 min and dried at room temperature. CB copolymers with varying amphiphilicities were dissolved in ethanol with 0.50 wt % concentration, respectively. Each substrate was immersed in a polymer solution for 10 s, followed by solvent evaporation under atmospheric pressure in an ethanol vapor-protective environment at room temperature. All modified PP substrates were soaked in phosphate-buffered saline (PBS, 1×, pH 7.4) for 1 h at room temperature. Afterwards, the substrate was rinsed with DI water and dried in a vacuum desiccation for 24 h at room temperature. To determine the effect of polymer concentration on coating efficiency, cleaned PP substrates were coated with CB copolymers at different concentrations (0.03, 0.06, 0.13, 0.25, 0.5 and 1.00 wt %) for further testing.

To quickly evaluate nonfouling capability of each coating, adsorbed single protein (fibrinogen) was measured by enzyme-linked immunosorbent assay (ELISA). In brief, polymer-coated PP substrates were pre-wetted in PBS overnight, then were immersed in 1.0 mg/mL fibrinogen in PBS for 1 h at 25° C. After rinsing with fresh PBS, PP substrates were soaked into solution of anti-fibrinogen antibody conjugated with HRP at room temperature for 30 min. Then, substrates were rinsed again and allowed to react with OPD/$H_2O_2$ mixture solution for another 15 min; mixture solution contained 1.0 mg/ml OPD and 1000 times diluted $H_2O_2$ in citrate buffer (1×, pH 5.0). After the reaction was quenched with 1.0 N HCl, absorbance of each solution at 492 nm was measured using a microplate reader (BioTek Instruments Inc., Winooski, Vt.).

Surface Coating on Multi-well Plates and Gold Chip. A 96-well plate made of original polystyrene was simply modified with CB copolymers using dip-coating solvent evaporation method mentioned above. The anti-fouling capability was compared to both commercial 96-well plate with an ultra-low attachment surface and uncoated polystyrene 96-well plate. The gold chips were made of a BK7 glass slide coated with a first titanium film layer (~2 nm) and a second gold layer (~48 nm) using an electron beam evaporator. The chip was ultrasonically washed with acetone, DI water, and ethanol for 5 min in each solvent. Subsequently, they were treated by UV/ozone cleaner for 30 min and immersed into 0.2 mM 1-decanethiol for 24 h to form a hydrophobic self-assembled monolayer. Finally, chips were dip-coated with CB polymers using same procedure above. The thickness of coated polymer layer was measured under dry conditions with a spectroscopic ellipsometer (α-SE; J. A. Woolam Co., Inc., Tokyo, Japan).

Protein Adsorption from Single-protein Solution and 100% Human Serum. The nonfouling capability of CB random copolymer coatings was comprehensively tested against both single proteins and whole human blood serum. Single blood protein at 10% concentration has been frequently used as a standard to assess biofouling on various surfaces. Thus, evaluation of nonfouling capability against 100% single blood protein and 100% human blood serum is attractive and essential for blood contacting devices. The coated 96-well plate was pre-wetted with DI water at room temperature before testing protein adsorption. Micro BCA protein assay kit was used to evaluate protein adsorption against human plasma fibrinogen (Fg), human serum albumin (HSA), human blood γ-globulin, and human serum. The concentration of Fg, HSA and γ-globulin are 3.0, 45, and 16 mg/mL respectively, which is equivalent to the 100% of the concentration found in human plasma. Normal human blood serum (100%, pooled mixed gender) was used as received. In brief, human protein (dissolved in PBS, 1×, pH 7.4) or undiluted human serum were incubated within pre-wetted wells at 37° C. for 2 h, and were rinsed with fresh PBS (1×, pH 7.4). Adsorbed proteins were detached in 1.0 ml of 1.0 wt % sodium n-dodecyl sulfate (SDS) solution. 150 μL of the liquid supernatant were transferred into 96-well plate and gently mixed with another 150 μL of bicinchoninic acid (BCA) reagents. After incubation at 37° C. for 2 h, a purple-colored product is generally formed by the chelation of two molecules of BCA with one cuprous ion ($Cu_{+1}$), which is reduced from $Cu_{+2}$ by protein in an alkaline environment. Finally, a microplate reader was used to determine the absorbance at 562 nm. The absorbance at 562 nm shows a linear with increasing amount of adsorbed proteins.

Cell Adhesion. NIH3T3 mouse embryonic fibroblast cells obtained from American Type Culture Collection (ATCC, Rockville, Md.) were seeded in a polystyrene tissue culture dish ($\Phi$=10 cm, $5.0 \times 10^4$ cells/mL) in Dulbecco's modified eagle medium (DMEM) supplemented with 10% fetal bovine serum (FBS) at 37° C. in a humidified atmosphere containing 5.0% $CO_2$. Sub-confluent cell cultures were passaged using 0.25% trypsin/EDTA. Sterilized CB polymer solution (0.5 wt %, ethanol) was dropped onto the surface of tissue culture plate and evaporated in the cell culture hood. Then, the coated surface was rinsed with PBS (1×, pH 7.4) and pre-wetted with DMEM overnight at room temperature. NIH3T3 cells were seeded into the partially coated dish at a concentration of $5.0 \times 10^4$ cells/mL in DMEM supplemented with 10% FBS at 37° C. in a humidified atmosphere containing 5.0% $CO_2$. After 3 days' incubation, the medium was replaced and morphology of the cells on the partially coated surface was observed using a Nikon Eclipse TE2000-U microscope (Nikon Instruments, Melville, N.Y.).

Surface Functionalization. Surface functionalization was performed on the PCB2-37 coated 96-well polystyrene plate. The surface modification procedure has been described above in detail using a dip-coating and solvent evaporation method. The carboxyl group on the polymer surface can be easily activated by EDC/NHS chemistry, and covalently bond with amino groups of, for example, proteins, enzyme, and aptamer/oligonucleotides. In brief, first, 0.15 mL of a freshly prepared solution containing 0.1 M NHS and 0.4 M EDC in DI water was added into coated 96-well plate for 30 min at 25° C. to activate the carboxylate group. Second, the solution of EDC and NHS was removed and the surface of well was rinsed with 10 mM SA buffer (pH 5.0) three times. Third, 0.15 mL Fg solution (1.0 mg/mL) in 10 mM TAPS (pH 8.2) was added into the activated well and allowed to react for 30 min at 25° C. Subsequently, the functionalized surface was washed three times with BA buffer (10 mM boric acid and 300 mM sodium chloride, pH 9.0) and then phosphate buffered saline (PBS, 1×, pH 7.4) before evaluation of antibody-antigen specific interaction. Along with above protein immobilization process the residual activated carboxyl groups were also de-activated. The Fg-functionalized 96-well plate was gently rinsed with fresh PBS three times. Subsequently 0.15 mL of anti-fibrinogen antibody conjugated with HRP in PBS solution were added into each well for 30 min at 25° C. After that, the wells were rinsed again and allowed to react with 0.15 mL of $OPD/H_2O_2$ solution for another 15 min. The chromogenic reaction was quenched through adding 0.15 mL 1.0 N of hydrochloride acid solution. The absorbance at 492 nm in each solution was measured using a microplate reader mentioned above. For comparison, a non-activated CB polymer coated 96-well plate yet contacted with Fg, and an activated CB polymer surface but functionalized with HSA were utilized as control.

Statistical Analysis. All graphs and bar charts are expressed as the mean±standard deviation (SD) of three or five repeated experiments as described above. Student's t-test was carried out to determine whether the observed differences were statistically significant.

Example 2

Preparation, Characterization, and Use of Representative Zwitterionic/Photoreactive Copolymers In this example, the preparation, characterization, and use of representative zwitterionic/photoreactive copolymers of the invention is described.

Materials. Carboxybetaine acrylamide, 1-carboxy-N,N-dimethyl-N-(3'-acrylamidopropyl) ethanaminium inner salt (CBAA) were synthesized according to a previously reported method (Zhang, Z.; Vaisocherová, H.; Cheng, G.; Yang, W.; Xue, H.; Jiang, S., Nonfouling Behavior of Polycarboxybetaine-Grafted Surfaces: Structural and Environmental Effects. *Biomacromolecules* 2008, 9, 2686-2692). The following materials and reagents were obtained from Sigma-Aldrich (St. Louis, Mo.) and used without any further purification: 2,2'-azobisisobutyronitrile (AIBN), 1-decanethiol, and sodium n-dodecyl sulfate (SDS). Phosphate-buffered saline (10×, solution) was obtained from Fisher Scientific Co. (Fair Lawn, N.J.). Normal human blood serum (pooled mixed gender) was purchased from BioChemed Services (Winchester, Va.). Micro BCA protein assay kit and RBS™ 35 Concentrate were purchased from Thermo Scientific (Waltham, Mass.). Ethanol (200 proof) was purchased from Decon Labs (King of Prussia, Pa.). The water was obtained from a Millipore water purification system with a minimum resistivity of 18.0 MΩcm. Other organic reagents and solvents were commercially available as extra-pure grade reagents and were used as received.

Polymer synthesis and characterization. The photosensitive monomer, N-(4-benzoylphenyl) acrylamide (BPAA), was synthesized through the reaction between methacryloyl chloride and 4-amino benzophenone. The amphiphilic PCB copolymer, poly(CBAA-co-BPAA) was synthesized by a conventional free-radical polymerization method using AIBN as a thermal initiator (a similar method was reported previously: Lin, X.; Fukazawa, K.; Ishihara, K., Photoreactive Polymers Bearing a Zwitterionic Phosphorylcholine Group for Surface Modification of Biomaterials. *ACS Applied Materials & Interfaces* 2015, 7, 17489-17498). In brief, desired amounts of the CB monomers and initiator were dissolved in ethanol. The solution was transferred to a Pyrex Vista glass tube reactor and further purged with nitrogen gas for 30 min at room temperature. Polymerization was performed in the sealed glass tube under a protective atmosphere of nitrogen gas. After polymerization, the reaction solution was slightly dropped into a mixed poor solvent of ether/chloroform to precipitate copolymers. The copolymer was filtered off and collected as a white powder after vacuum desiccation for 24 h at room temperature. The residual water-soluble monomer was removed by dialysis against DI water for 4 days. Then, the copolymer was frozen by liquid nitrogen and treated with a lyophilizer (Labconco Co., Ltd., Kansas City, Mo.) at −80° C. for 48 h. The chemical structures of purified copolymers were confirmed using $^1$H NMR (AV-500, Bruker, Germany), and polymers were cryopreserved at −20° C. A UV light (312 nm, 600 mJ/cm$^2$) was applied to the polymer, and the light sensitivity was evaluated using Varian Cary 5000 UV-Vis-NIR Spectrophotometer.

Surface modification. Medicalgrade PVC tubing obtained from a Streamline Airless System Set (Medisystems Corporation, MA) was cut into 10 cm length. PCB copolymer solution (0.5 wt %, ethanol) was then filled into the tubing, which was subsequently sealed and put onto a rotator for 10 min to ensure the whole internal surface was contacted with the polymer solution. Then, the polymer solution was removed, and the coated tubing was blown with dry air at room temperature. An external UV light (312 nm, 600 mJ/cm$^2$) was applied on the coated tubing to stabilize polymer on the internal surface. Sterilized PBS (1×, pH 7.4) was used to wash away unstable polymer and pre-wet the surface before the addition of human blood serum for fouling test. The solution was sterilized by filtration through a 0.45 μm filter.

Surface characterization. The surface wettability of each sample was characterized by measuring the water contact angle. Distilled water was added into both uncoated and PCB-coated PVC tubing, followed by the observation of water contact angle. X-Ray photoelectron spectroscopy (XPS) was performed using a Kratos AXIS Ultra DLD spectrometer. The survey spectrum and atom were analyzed on four different samples: (a) PCB copolymer, (b) uncoated commercial PVC tubing, (c) PCB-coated commercial PVC tubing storage for 1 week at the dry condition, and (d) PCB-coated commercial PVC tubing storage for 3 weeks at the dry condition.

Biofouling assessment. Human blood protein adsorption on PCB coated commercial PVC tubing against 100% human serum was evaluated using a Micro BCA protein assay kit. Normal human blood serum (100%, pooled mixed gender) was used as received. In brief, both PCB coated and uncoated PVC tubing (10 cm length) were filled with 100% human serum and incubated at 37° C. for 2 h. Then, the tubing was rinsed with fresh PBS (1×, pH 7.4). Adsorbed proteins were detached in 1.0 wt % sodium n-dodecyl sulfate (SDS) solution. 150 μL of the liquid supernatant was transferred into 96-well plate and gently mixed with another 150 μL of bicinchoninic acid (BCA) reagents. After incubation at 37° C. for 2 h, a purple-colored reaction product is generally formed by the chelation of two molecules of BCA with one cuprous ion ($Cu_{+1}$), which is reduced from $Cu_{+2}$ by protein in an alkaline environment. Finally, a microplate reader was used to determine the absorbance at 562 nm. The absorbance at 562 nm shows a linear with increasing amount of adsorbed proteins.

Example 3

Preparation, Characterization, and Use of Representative Zwitterionic/Photoreactive Copolymers to Prevent Plasticizer Leaching from Plastic Surfaces In this example, the preparation, characterization, and use of representative zwitterionic/photoreactive copolymers of the invention to prevent leaching of plasticizers from plastic surfaces is described.

Materials. Carboxybetaine acrylamide, 1-carboxy-N,N-dimethyl-N-(3'-acrylamidopropyl) ethanaminium inner salt (CBAA) was synthesized as described in Example 2. The following materials and reagents were obtained from Sigma-Aldrich (St. Louis, Mo., USA) and used without any further purification: 2,2'-azobisisobutyronitrile (AIBN) and 1-decanethiol, sodium n-dodecyl sulfate (SDS), poly(ethylene glycol) methacrylate (PEGMA) (average Mn 360). Nile blue (NB) acrylamide was purchased from Polysciences, Inc. (Warrington, Pa., USA). Normal human blood serum (100%, pooled mixed gender) was purchased from BioChemed Services (Winchester, Va., USA). The Micro BCA protein assay kit and the RBS 35 concentrate were purchased from Thermo Scientific (Waltham, Mass., USA). Phosphate-buffered saline (10×, solution) was obtained from Fisher Scientific Co. (Fair Lawn, N.J., USA). Normal human blood serum (pooled mixed gender) was purchased from BioChemed Services (Winchester, Va., USA). Micro BCA protein assay kit and RBS™ 35 Concentrate were purchased from Thermo Scientific (Waltham, Mass., USA). Ethanol (200 proof) was purchased from Decon Labs (King of Prussia, Pa., USA). The water was obtained from a Millipore water purification system with minimum resistivity of 18.0 MΩcm. Other organic reagents and solvents were commercially available as extra-pure grade reagents and were used as received.

Polymer synthesis and characterization. The photosensitive monomer, N-(4-benzoylphenyl) acrylamide (BPAA), was synthesized through the reaction between acryloyl chloride and 4-aminobenzophenone. The amphiphilic PCB copolymer, poly(CBAA-co-BPAA) was synthesized by a conventional free-radical polymerization method using AIBN as a thermal initiator and characterized as described in Example 2.

Surface modification. The medical-grade PVC tubing obtained from a Streamline Airless System Set (Medisystems Corporation, MA, USA) was cut into 15 cm length. The PCB copolymer solution (0.5 wt %) was then filled into the tubing, which was subsequently sealed and put onto a rotator for 10 min to ensure the whole internal surface was contacted with the polymer solution. Then, the polymer solution was removed, and the coated tubing was blown with dry air at room temperature. An external UV light (312 nm, 600 mJ/cm$^2$) was applied on the coated tubing to stabilize polymer on the internal surface. Sterilized PBS (1×, pH 7.4) was used to wash away physically adsorbed polymers and pre-wet the surface before the addition of human blood serum for subsequent tests. To evaluate the effect of PCB polymers on platelet quality, a commercial platelet bag (Teruflex, 150 mL, Terumo Corporation, Tokyo, Japan) made of plasticized PVC was coated according to the above methods. The solution was sterilized by filtration through a 0.45 µm filter. To evaluate the coating stability, PCB polymer tagged with Nile blue (PCB-NB) was coated on the PVC tubing according to the method mentioned above. The tubing was filled with sterilized PBS (1×, pH 7.4) and incubated at 37° C. for the desired period. The UV/vis absorption spectrum (250-800 nm) and fluorescent spectrum (exciting: 590 nm, 200-900 nm) of the solution were obtained using a UV-Vis-NIR spectrophotometer and fluorospectrophotometer.

The SPR chips were ultrasonically sequentially washed with acetone, DI water, and ethanol successively for 5 min each. Subsequently, they were cleaned using a UV/ozone cleaner for 30 min and immersed in 0.2 mM 1-decanethiol for 24 h to form a hydrophobic self-assembled monolayer. Commercial PVC tubing and the PCB polymers were dissolved into tetrahydrofuran (THF) and DI water, respectively. The SPR chips were successively spin-coated with these two solutions. A UV light (312 nm, 600 mJ/cm$^2$) was applied on the surface of coated chips. The thickness of the coated polymer layer was measured with a spectroscopic ellipsometer (α-SE; J. A. Woolam Co., Inc., Tokyo, Japan) under dry conditions.

Surface characterization. The surface wettability of each sample was characterized by measuring the water contact angle. Distilled water was added into both uncoated and PCB-coated PVC tubing, followed by the observation of water contact angle within 10 s through the analysis of photographic images. For each sample, five measurements were taken. X-ray photoelectron spectroscopy (XPS) was performed using a Kratos AXIS Ultra DLD spectrometer. The survey spectrum and atom compositions were analyzed on four samples: (1) PCB copolymers, (2) uncoated commercial PVC tubing, (3) PCB-coated commercial PVC tubing storage for 1 week at the dry condition, and (4) PCB-coated commercial PVC tubing storage for 3 weeks at the dry condition. The binding energy (BE) was corrected using the C1s peak at 285 eV as a reference. XPS survey spectrum, high-resolution spectra of C 1s, O 1s and N 1s, and atom composition were obtained for surface analysis.

Biofouling assessments. Human blood protein adsorption on PCB coated commercial PVC tubing against 100% human serum was evaluated under both static conditions and dynamic conditions using a Micro BCA protein assay kit and surface plasmon resonance (SPR), respectively. In brief, both PCB coated and uncoated PVC tubing (10 cm length) were filled with 100% human serum and incubated at 37° C. for 2 h. Then, the tubing was rinsed with fresh PBS (1×, pH 7.4). Adsorbed proteins were detached in 1.0 wt % sodium n-dodecyl sulfate (SDS) solution. The liquid supernatant was gently mixed with bicinchoninic acid (BCA) reagents. A microplate reader (BioTek Instruments Inc., Winooski, Vt., USA) was used to determine the absorbance at 562 nm. Adsorption of human blood protein under dynamic condition was calculated using SPR, which was equipped with a four-individual flow channel, temperature control, an intensity stabilizer, and a peristaltic pump for delivering liquid samples for real-time monitoring interaction between polymer surface and protein solution. The coated SPR chip was pre-wetted in PBS (1×, pH 7.4). The behavior of protein adsorption was monitored on the PCB-coated SPR chip surface by subsequently flowing the following solutions in turn at 25° C.: (a) PBS solution (1×, pH 7.4), 10 min; (b) undiluted normal human blood serum, 10 min; and (c) PBS solution (1×, pH 7.4), 10 min, under four different flow rates (10, 40, 100, and 200 µL/min). Data at 750 nm was collected while flowing different solutions and the amount of fouling was quantitatively assessed by determining the change of wavelength caused by protein adsorption on the surface.

Polymer cytotoxicity. The cytotoxicity of the PCB polymer was checked based on ISO 10993-5 guideline. In brief, a fast-growing cell line, NIH3T3 mouse embryonic fibroblast cells were seeded in a 12-well plate to result in sub-confluent cultures in 24 hours. As elution samples, both the coated and uncoated PVC tubing was cut into 0.2 g with the same shape and put into two separate TCPS wells of a plate containing cell culture medium, followed by incubation at 37° C. for 24 hours. Blank well of a TCPS plate incubated in normal media was used as negative control while a small piece of latex (cut from a pipette bulb and sterilized in 70% ethanol) was used as a positive control. Transfer extract media from a material sample onto one well of sub-confluent cells for each of the triplicate samples of each material being tested. Incubate cultures at 37° C. for an additional 48 h and remove for microscope examination at 24 and 48 h time points. Observe cells for visible signs of toxicity indicated by any change from normal morphology compared to the negative control cells. Rate on a reactivity grade from 0 to 4 using guidelines developed by ISO 10993-5. The PCB polymer was dissolved in cell culture medium at different concentrations (0.00125, 0.0025, 0.01, and 0.1 mg/mL) and transferred into the TCPS well with NIH3T3 cells for an additional 48 h culture at 37° C. The same examination protocols mentioned above were performed. In addition, the release of the cytosolic enzyme lactate dehydrogenase (LDH), which corresponded to the cytotoxicity of the synthetic PCB polymers, was determined using a Lactate Dehydrogenase Activity Assay Kit (Sigma-Aldrich, St. Louis, Mo., USA).

Plasticizer leaching. Both the PCB-coated and uncoated PVC tubing (15 cm length) were filled with PBS solution (1×, pH 7.4) and incubated at 37° C. for 24 h. The solution inside the tubing was taken out at 4, 12 and 24 h time points. The UV/vis absorption spectrum (200-800 nm) was obtained using a UV-Vis-NIR spectrophotometer. The absorption values at 275 nm wavelengths were compared between coated and uncoated PVC tubing.

Platelet quality. The effect of PCB polymer to the blood platelet quality was comprehensively evaluated using a commercial flexible platelet bag (Teruflex, 150 mL, Terumo Corporation, Tokyo, Japan) made of plasticized PVC. The commercial platelet bag was coated with PCB polymer using a simple dip-coating method similar to the above protocol. The same volume (30 mL) of fresh platelet solution was added into the PCB-coated and uncoated commercial bag, respectively. All experiments were performed benchtop and samples were stored on an orbital shaker (15 rpm) in an incubator (5% CO$_2$, 25° C.). The expression of annexin V and p-selectin, platelet morphology score, and platelet binding capability with von Willebrand factor (VWF) were evaluated.

Complement activation. The complement activation was measured based on sC5b-9 using the correspondent human ELISA kit (Quidel, San Diego, USA). The coated PVC tubing (15 cm length) was filled with un-activated human serum and sealed with tape before incubation at 37° C. with slight rotation. After the desired incubation period (90 min), the incubated serum was taken out and diluted with sample buffer provided by the supplier and applied to a 96 well plate precoated with an antibody directed against sC5b-9. The other steps were performed strictly according to the protocol from the supplier. The concentrations of sC5b-9 were measured as absorption (450 nm) of the chromogenic substrate using a microplate reader (BioTek Instruments Inc., Winooski, Vt., USA). An amphiphilic copolymer, poly (PEGMA-co-BPAA) (PPB) was prepared by the same polymerization and purification method as PCB. The commercial PVC tubing coated with PPB was used as a positive control sample.

Statistical Analysis. All graphs and bar charts are expressed as the mean±standard deviation (SD) of three or five repeated experiments as described above. The Student's t-test was carried out to determine whether the observed differences were statistically significant.

Example 4

Preparation, Characterization, and Use of Representative Zwitterionic/Hydrophobic/Photoreactive Copolymers In this example, the preparation, characterization, and use of representative zwitterionic/hydrophobic/photoreactive copolymers of the invention is described.

Polymer synthesis and characterization. As the covalent binding group, the photosensitive monomer, N-(4-benzoylphenyl) acrylamide (BPAA), was synthesized. The amphiphilic PCB copolymer, poly(CBAA-co-BMA-co-BPAA) was synthesized by a conventional free-radical polymerization method using AIBN as an initiator. In brief, desired amounts of the CB monomers and initiator were dissolved in ethanol. The solution was transferred to a Pyrex Vista glass tube reactor and further purged with nitrogen gas for 30 min at room temperature. Polymerization was performed in the sealed glass tube under a protective atmosphere of nitrogen gas. After polymerization, the reaction solution was slightly dropped into a mixed solvent of ether/chloroform to precipitate copolymers. The copolymer was filtered off and collected as a white powder after vacuum desiccation for 24 h at room temperature. The residual water-soluble monomer was removed by dialysis against DI water for 4 days. Then, the copolymer was frozen by liquid nitrogen, and treated with a lyophilizer (Labconco Co., Ltd., Kansas City, Mo.) at −80° C. for 48 h. The chemical structures of purified copolymers were confirmed using $^1$H NMR (AV-500, Bruker, Germany), and polymers were cryopreserved at −20° C. A UV light (312 nm, 600 mJ/cm$^2$) was applied to the polymer, and the light sensitivity was evaluated using Varian Cary 5000 UV-Vis-NIR Spectrophotometer.

Surface modification. The commercialized platelet bag (Teruflex, 150 mL, Terumo Corporation, Tokyo, Japan) was rinsed with 10 mL of ethanol for 10 s and blew with dry air at room temperature. 20 mL of PCB polymer aqueous solution (0.5 wt %, DI water) was then injected into the bag, and the bag was put onto a platelet storage shaker for 10 min to ensure the whole internal surface was contacted with the polymer solution. Subsequently, the polymer solution was removed using a syringe, and the coated bag was blown with dry air overnight at room temperature. A UV light (312 nm, 600 mJ/cm$^2$) was applied on each side of the coated bag to stabilize polymer on the surface. Sterilized PBS (1×, pH 7.4) was used to wash away unstable polymer and pre-wet the surface before the addition of human platelet solution. The solution was sterilized by filtration through a 0.45 µm filter. A similar dip-coating method was used to coat the small pieces (1 cm×1 cm) of commercialized platelet bag. The SPR chips were made of a BK7 glass slide coated with a first titanium film layer (about 2 nm) and a second gold layer (about 48 nm) using an electron beam evaporator. The chip was ultrasonically washed with acetone, DI water, and ethanol for 5 min in each solvent. Subsequently, they were treated by UV/ozone cleaner for 30 min and immersed into 0.2 mM 1-decanethiol for 24 h to form a hydrophobic self-assembled monolayer. The commercialized platelet bag was cut and dissolved into the THF solution at 0.5 wt %. The chips were successively spin-coated with commercialized platelet bag/THF solution and PCB copolymer/DI water solution. A UV light (312 nm, 600 mJ/cm$^2$) was applied on the surface of coated chips. The thickness of the coated polymer layer was measured under dry conditions with a spectroscopic ellipsometer (α-SE; J. A. Woolam Co., Inc., Tokyo, Japan).

Surface characterization. The surface wettability of each sample was characterized by measuring the water and air contact angle with a static contact angle goniometer. Distilled water droplets were deposited onto substrate surfaces, and the water contact angles were measured within 10 s through the analysis of photographic images. For the measurement of the air contact angle, all the samples were immersed into distilled water for 1.0 h before measurement. Samples were fixed onto a custom holder and were subsequently immersed into distilled water in a glass vessel. Air bubbles were introduced underneath each sample in contact with the measurement surface through a U-shaped needle. For each sample, five different points were measured. XPS analysis was performed using a Kratos AXIS Ultra DLD spectrometer on five different samples: (1) PCB copolymer, (2) commercialized platelet bag, (3) commercialized platelet bag rinse with ethanol, (4) PCB-coated commercialized platelet bag, and (5) PCB-coated commercialized platelet bag soaked in buffer. XPS survey spectrum, high-resolution spectra of C 1s, O 1s and N 1s, and atom composition was recorded for surface analysis. The $O_2$ permeability of coated bag was tested using a portable oxygen meter.

Human blood protein adsorption. Human blood protein adsorption on PCB coated commercialized platelet bag against 100% human serum were evaluated under both static condition and dynamic condition using a Micro BCA protein assay kit and surface plasmon resonance (SPR), respectively. Normal human blood serum (100%, pooled mixed gender) was used as received. In brief, PCB coated small pieces (1 cm×1 cm) of commercialized platelet bags were incubated with serum at 37° C. for 2 h, and subsequently were rinsed with fresh PBS (1×, pH 7.4). Adsorbed proteins were detached in 1.0 ml of 1.0 wt % sodium n-dodecyl sulfate (SDS) solution. 150 µL of the liquid supernatant was transferred into 96-well plate and gently mixed with another 150 µL of bicinchoninic acid (BCA) reagents. After incubation at 37° C. for 2 h, a purple-colored reaction product is generally formed by the chelation of two molecules of BCA with one cuprous ion ($Cu^{+1}$), which is reduced from $Cu^{+2}$ by protein in an alkaline environment. Finally, a microplate reader was used to determine the absorbance at 562 nm. The absorbance at 562 nm shows a linear with increasing amount of adsorbed proteins. Adsorption of human blood protein under dynamic condition was recorded using SPR, which was equipped with a four-individual flow channel, temperature control, intensity stabilizer, and a peristaltic pump for delivering liquid samples for real-time monitoring interaction between polymer surface and proteins. The coated SPR chip was pre-wetted in PBS (1×, pH 7.4). The places that liquid flows through was sufficiently rinsed with PBS (1×), $H_2O$, HCl (0.1 N) and PBS (1×, pH 7.4) solution before measurement. The protein adsorption behavior was monitored on the PCB-coated SPR chip surface by subsequently flowing the following solutions at 25° C.: (a) PBS solution (1×, pH 7.4), 10 min, 40 μL/min; (b) undiluted normal human blood serum, 10 min, 40 μL/min; and (c) PBS solution (1×, pH 7.4), 10 min, 40 μL/min. The wavelength at 750 nm was recorded along with the flowing of different solutions. The fouling amount was quantified by measuring the change in wavelength at 750 nm before and after protein adsorption.

Cell adhesion. NIH3T3 mouse embryonic fibroblast cells obtained from American Type Culture Collection (ATCC, Rockville, Md., USA) were seeded in a polystyrene tissue culture dish (Φ=10 cm, $5.0 \times 10^4$ cells/ml) in Dulbecco's modified eagle medium (DMEM) supplemented with 10% FBS at 37° C. in a humidified atmosphere containing 5.0% $CO_2$. Sub-confluent cell cultures were passaged using 0.25% trypsin/EDTA. Sterilized CB polymer solution (0.5 wt %, ethanol) was dropped onto the surface of tissue culture plate and evaporated in the cell culture hood. Then, the coated surface was stabilized under a UV irradiation (312 nm, 600 mJ/cm$^2$) and rinsed with PBS (1×, pH 7.4). NIH3T3 cells were seeded at a concentration of $5.0 \times 10^4$ cells/mL in DMEM supplemented with 10% FBS at 37° C. in a humidified atmosphere containing 5.0% $CO_2$. After 3 days' incubation, the medium was replaced and morphology of the cells on the partially coated surface was observed using a Nikon Eclipse TE2000-U microscope (Nikon Instruments, Melville, N.Y.).

Human platelet adhesion. Fresh human platelets were received from Bloodworks Northwest (Seattle, Wash.) on the day of donation. 500 μL of platelet-rich plasma (PRP) were seeded on the top of samples in a 24-well plate and incubated for 45 min at 37° C. Then, the samples were rinsed with sterilized normal saline (NS) and fixed using 2.5% glutaraldehyde solution at 25° C. for 4 h. After that, the samples were rinsed with sterilized normal saline (NS) again and dried at 25° C. The surfaces of the samples were observed using both Nikon Eclipse TE2000-U microscope and Scanning Electron Microscope (SEM; SNE-3200M, SEC, Korea).

Bacteria adhesion test. A gram-positive strain of *Staphylococcus epidermidis* and a gram-negative strain of *Pseudomonas aeruginosa* were grown separately in trypticase soy broth (TSB) for 12 h at 37° C. with shaking at 200 rpm. The suspended culture was diluted and then additionally grown in TSB for 2 h to reach exponential growth phase. When the second suspended culture reached an optical density of 1.0 at 600 nm, bacteria were centrifuged at 8000 rpm and resuspended in sterile PBS (1×, pH 7.4) to a concentration of about $1 \times 10^8$ CFU/mL. Exponentially grown bacteria were then placed on the samples in the 24-well plate and cultured for 24 h at 37° C. Afterward, the samples were gently washed with sterile PBS to remove non-adherent bacteria and then stained with 50 nM SYTO9 (green fluorescent nucleic acid stain). The results were directly observed using Nikon Eclipse TE2000-U microscopes.

Platelets property assessment. Fresh human platelets were received from Bloodworks Northwest (Seattle, Wash.) on the day of donation. Custom ficoll program was used to dilute leukapheresis product and remove platelets to a designated bag (Teruflex, Terumo Corporation, Tokyo, Japan) at a concentration between $(2.0-4.3) \times 10^8$ cells/mL.

All stored platelet collections met the manufacturers' guidelines for platelet concentration, total platelet count and storage volume as reported by Bloodworks NW. Platelet counts were performed using a Hematology Analyzer (ABX Diagnostics, Irvine, Calif.). All experiments were performed benchtop and samples stored on an orbital shaker (15 rpm) in an incubator (5% $CO_2$, 25° C.). Same volume (30 mL) of fresh platelet solution was added into the PCB-coated and uncoated commercialized bag (Teruflex, 150 mL, Terumo Corporation, Tokyo, Japan) with agitation at room temperature. Here, the expression of annexin V and p-selectin; pH, glucose and lactate level of platelet solution; platelet morphology score and platelet binding capability with von Willebrand Factor (VWF) were evaluated, respectively.

Annexin V. Platelets were harvested after the different incubation period (1, 6, 24, 48, 120, 144, 168, 192, and 216 hr) and were washed in PBS (1×, pH 7.4) solution at a concentration of $5.0 \times 10^6$ cells/mL at 300 g for 8 minutes. After discarding the supernatant, platelets were reconstituted with 2.0 mL of binding buffer (Annexin V Binding Buffer, 10× concentrate, BD Pharmingen™ Becton, Dickinson and Company, NJ) and gently mixed. Then, 100 μL was transferred to a 5.0 mL culture polystyrene flow cytometry tube (Falcon™, Thermo Fischer Scientific), stained with 1.0 μL of FITC Annexin V Apoptosis Detection Kit I (BD Biosciences, Excitation/Emission: 496/578 nm). Cells were incubated at room temperature in the dark for 20 minutes. Samples were analyzed after incubation in the FACScan flow cytometer (Becton-Dickinson, San Jose, Calif.) to detect Annexin V binding levels. Platelets preserved in the uncoated bag were used as a control sample.

p-Selectin (CD62). Platelets were harvested after the same incubation period as shown above, and they were re-suspended in an aqueous buffered solution containing PBS (1×, pH 7.2), 0.2% fetal bovine serum and 0.09% sodium azide at $5.0 \times 10^6$ cells/mL. This was followed by centrifugation at 300 g for 8 minutes. After discarding the supernatant, platelets were stained with 1.0 μL of a monoclonal mouse anti-human antibody at a final concentration of 1:100 (FITC Mouse Anti-Human CD62P, Excitation/Emission: 494/520 m) gently homogenized with a vortex mixer. Cells were then incubated at room temperature for 30 minutes in the dark. After incubation, samples were analyzed in FACSCAN. Platelets preserved in the uncoated bag were used as a control sample.

Morphology score. The healthiest platelets exhibit a disc shape, and the maximum score possible is 400 (meaning 100%-disc morphology), but scores around 380 are common for fresh donor platelets. Morphology scoring is commonly used to predict platelet health defined on shape and is defined as:

$$M = 4 \times (\text{disc \%}) + 2 \times (\text{spheres \%}) + 1 \times (\text{dendrite \%})$$

MFI for VWF binding affinity. Expression of glycoprotein Ib-alpha (BPIb-alpha) (anti-CD42b fluorescein; Life Technologies, Carlsbad, Calif.) was used. Binding of VWF to platelets was determined using Alexa Fluor 488 labeled polyclonal anti-VWF antibody. Platelets were incubated for 15 minutes at room temperature in 10 mM HEPES buffer, pH 7.4 with 0.9% NaCl, supplemented with 1.0 mM $MgSO_4$. Medium fluorescence intensities (MFI) of the anti-VWF signal were collected where the condition of fresh platelets is set to 100%.

Glucose and Lactate Levels. Using a blood-gas analyzer (ABL 800, Radiometer, Copenhagen, Denmark), glucose (mmol/L) and lactate (mmol/L) were measured via the electrochemical signal at Day 1, 3, 5, and 7. The glucose measurements measure the concentration of glucose in the plasma solution; this serves as a marker of energy supply. The lactate measurements measure the concentration of lactate in the plasma solution; this serves as a marker of imbalance between tissue oxygen demand and supply. Here, the potential of an electrode chain is recorded using a voltmeter and related to the concentration of the sample using the Nernst equation. Electrode signals are registered with a 0.982-second interval during measurement and calibration. An amperometric method utilizing a membrane selective to respective species, glucose or lactate, is used.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for inhibiting or preventing leaching of a plasticizer from a surface of a substrate, comprising:
   (a) coating at least a portion of a surface of a substrate with a composition comprising a copolymer to provide a coated surface, the copolymer comprising first repeating units and second repeating units, wherein each of the first repeating units comprises a pendant zwitterionic group, and wherein each of the second repeating units comprises a pendant photoreactive group effective for crosslinking the copolymer on a surface, to provide a coated surface; and
   (b) irradiating the coated surface with ultraviolet light effective to crosslink the copolymer on the surface, thereby providing a coated surface effective for inhibiting or preventing leaching of a plasticizer from the surface;
wherein the copolymer has formula (III):

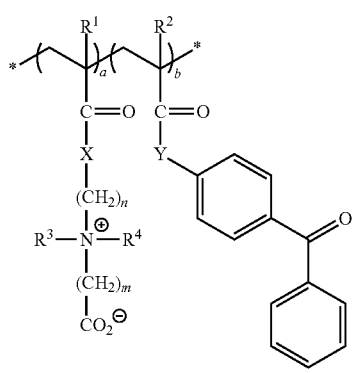

(III)

wherein
$R_1$ and $R_2$ are independently $-(CH_2)_xH$, where x is an integer from 0 to 20;
$R_3$ and $R_4$ are independently $(CH_2)_xH$, where x is an integer from 0 to 20;
X is O or NH;
Y is O or NH;
n is an integer from 1 to 20;
m is an integer from 1 to 20;
a is from about 0.10 to about 0.90 mole percent;
b is about 0.10 to about 0.90 mole percent;
a+b is 1.0; and
* represents the copolymer terminal groups.

2. The method of claim 1, wherein the surface is a blood-contacting surface.

3. The method of claim 1, wherein the substrate is polyurethane tubing, polysulfone dialysis membrane, or hydrocarbon-based membrane container.

4. The method of claim 1, wherein coating the surface with the composition comprises dipping the surface into the composition.

5. The method of claim 1, wherein coating at least a portion of the surface comprises spraying, spinning, brushing, or rolling the composition onto the surface.

6. The method of claim 1, wherein the surface is a hydrocarbon-based surface.

7. The method of claim 1, wherein the surface is a cellulose, cellulose acetate, polyolefin, polyester, polycarbonate, polyurethane (PU), polysulfone (PSF), poly(ether sulfone) (PES), polyamide, polyacrylic, polyimide, aromatic polyester, polyethylene (PE), polypropylene (PP), polystyrene (PS), poly(ethylene terephthalate) (PET), polyvinyl chloride (PVC), poly(dimethyl siloxane) (PMDS), poly(vinylidiene fluoride) (PVDF), poly(lactic acid) (PLA), or poly(methyl methacrylate) (PMMA) surface.

8. The method of claim 1, wherein the surface is a polyvinyl chloride surface or a polyurethane surface.

9. The method of claim 1, wherein the surface is the surface of polyvinyl chloride tubing or polyurethane tubing.

10. The method of claim 1, wherein the copolymer further comprises third repeating units, wherein each of the third repeating units comprises a pendant hydrophobic group effective for adsorbing the copolymer to the plastic surface.

11. The method of claim 1, wherein m is 1 or 2.

12. The method of claim 1, wherein a is from about 0.70 to about 0.90 mole percent.

13. The method of claim 1, wherein a is about 0.80 mole percent.

14. The method of claim 1, wherein b is about 0.10 to about 0.30 mole percent.

15. The method of claim 1, wherein b is about 0.20 mole percent.

* * * * *